United States Patent
Hamp et al.

(10) Patent No.: US 12,217,829 B2
(45) Date of Patent: *Feb. 4, 2025

(54) ARTIFICIAL INTELLIGENCE-BASED ANALYSIS OF PROTEIN THREE-DIMENSIONAL (3D) STRUCTURES

(71) Applicant: Illumina, Inc., San Diego, CA (US)

(72) Inventors: Tobias Hamp, Essex (GB); Hong Gao, Palo Alto, CA (US); Kai-How Farh, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 17/232,056

(22) Filed: Apr. 15, 2021

(65) Prior Publication Data

US 2022/0336054 A1 Oct. 20, 2022

(51) Int. Cl.
*G16B 40/20* (2019.01)
*G06N 3/04* (2023.01)
(Continued)

(52) U.S. Cl.
CPC ........... *G16B 40/20* (2019.02); *G06N 3/04* (2013.01); *G06N 20/00* (2019.01); *G16B 20/20* (2019.02); *G16B 30/00* (2019.02)

(58) Field of Classification Search
None
See application file for complete search history.

(56) References Cited

U.S. PATENT DOCUMENTS

| 5,641,658 A | 6/1997 | Adams et al. |
| 6,090,592 A | 7/2000 | Adams et al. |

(Continued)

FOREIGN PATENT DOCUMENTS

| CA | 2894317 A1 | 12/2016 |
| CA | 3104851 A1 | 11/2020 |

(Continued)

OTHER PUBLICATIONS

Torng, W., & Altman, R. B. (2017). 3D deep convolutional neural networks for amino acid environment similarity analysis. BMC bioinformatics, 18(1), 1-23. (Year: 2017).*

(Continued)

*Primary Examiner* — Olivia M. Wise
*Assistant Examiner* — Mary C Leverett
(74) *Attorney, Agent, or Firm* — Keller Preece PLLC

(57) ABSTRACT

The technology disclosed relates to determining pathogenicity of variants. In particular, the technology disclosed relates to generating amino acid-wise distance channels for a plurality of amino acids in a protein. Each of the amino acid-wise distance channels has voxel-wise distance values for voxels in a plurality of voxels. A tensor includes the amino acid-wise distance channels and at least an alternative allele of the protein expressed by a variant. A deep convolutional neural network determines a pathogenicity of the variant based at least in part on processing the tensor. The technology disclosed further augments the tensor with supplemental information like a reference allele of the protein, evolutionary conservation data about the protein, annotation data about the protein, and structure confidence data about the protein.

30 Claims, 36 Drawing Sheets

(51) Int. Cl.
    *G06N 20/00*    (2019.01)
    *G16B 20/20*    (2019.01)
    *G16B 30/00*    (2019.01)

(56)            References Cited

U.S. PATENT DOCUMENTS

| | | | |
|---|---|---|---|
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,427,673 | B2 | 9/2008 | Balasubramanian et al. |
| 7,541,444 | B2 | 6/2009 | Milton et al. |
| 7,566,537 | B2 | 7/2009 | Balasubramanian et al. |
| 7,592,435 | B2 | 9/2009 | Milton et al. |
| 8,182,993 | B2 | 5/2012 | Tomaney et al. |
| 8,241,573 | B2 | 8/2012 | Banerjee et al. |
| 8,392,126 | B2 | 3/2013 | Mann |
| 8,401,258 | B2 | 3/2013 | Hargrove et al. |
| 8,407,012 | B2 | 3/2013 | Erlich et al. |
| 8,594,439 | B2 | 11/2013 | Staelin et al. |
| 8,725,425 | B2 | 5/2014 | Heiner et al. |
| 8,795,971 | B2 | 8/2014 | Kersey et al. |
| 8,965,076 | B2 | 2/2015 | Garcia et al. |
| 9,279,154 | B2 | 3/2016 | Previte et al. |
| 9,453,258 | B2 | 9/2016 | Kain et al. |
| 9,708,656 | B2 | 7/2017 | Turner et al. |
| 10,023,911 | B2 | 7/2018 | Tomaney et al. |
| 10,068,054 | B2 | 9/2018 | Van Rooyen et al. |
| 10,152,776 | B2 | 12/2018 | Langlois et al. |
| 10,168,438 | B2 | 1/2019 | Dennis et al. |
| 10,241,075 | B2 | 3/2019 | Davey et al. |
| 10,354,747 | B1 | 7/2019 | DePristo et al. |
| 10,423,861 | B2 | 9/2019 | Gao et al. |
| 10,491,239 | B1 | 11/2019 | Hubara |
| 10,527,549 | B2 | 1/2020 | Rebetez et al. |
| 10,540,591 | B2 | 1/2020 | Gao et al. |
| 10,619,195 | B2 | 4/2020 | Lamb et al. |
| 10,648,027 | B2 | 5/2020 | Mannion et al. |
| 10,711,299 | B2 | 7/2020 | Rothberg et al. |
| 10,713,794 | B1 | 7/2020 | He et al. |
| 10,740,880 | B2 | 8/2020 | Paik et al. |
| 10,740,883 | B2 | 8/2020 | Zerfass et al. |
| 10,755,810 | B2 | 8/2020 | Buckler et al. |
| 10,963,673 | B2 | 3/2021 | Schaumberg et al. |
| 11,138,496 | B2 | 10/2021 | Seth |
| 2002/0055100 | A1 | 5/2002 | Kawashima et al. |
| 2003/0062485 | A1 | 4/2003 | Fernandez et al. |
| 2004/0002090 | A1 | 1/2004 | Mayer et al. |
| 2004/0096853 | A1 | 5/2004 | Mayer |
| 2006/0014151 | A1 | 1/2006 | Ogura et al. |
| 2006/0040297 | A1 | 2/2006 | Leamon et al. |
| 2006/0064248 | A1 | 3/2006 | Saidi et al. |
| 2006/0188901 | A1 | 8/2006 | Barnes et al. |
| 2006/0240439 | A1 | 10/2006 | Smith et al. |
| 2006/0269130 | A1 | 11/2006 | Maroy et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0234136 | A1 | 9/2008 | Drmanac et al. |
| 2008/0242560 | A1 | 10/2008 | Gunderson et al. |
| 2009/0081775 | A1 | 3/2009 | Hodneland et al. |
| 2010/0046830 | A1 | 2/2010 | Wang et al. |
| 2010/0111370 | A1 | 5/2010 | Black et al. |
| 2010/0157086 | A1 | 6/2010 | Segale et al. |
| 2011/0059865 | A1 | 3/2011 | Smith et al. |
| 2011/0065607 | A1 | 3/2011 | Kersey et al. |
| 2011/0281736 | A1 | 11/2011 | Drmanac et al. |
| 2011/0286628 | A1 | 11/2011 | Goncalves et al. |
| 2011/0295902 | A1 | 12/2011 | Mande et al. |
| 2012/0015825 | A1 | 1/2012 | Zhong et al. |
| 2012/0020537 | A1 | 1/2012 | Garcia et al. |
| 2013/0059740 | A1 | 3/2013 | Drmanac et al. |
| 2013/0079232 | A1 | 3/2013 | Kain et al. |
| 2013/0124100 | A1 | 5/2013 | Drmanac et al. |
| 2013/0188866 | A1 | 7/2013 | Obrador et al. |
| 2013/0250407 | A1 | 9/2013 | Schaffer et al. |
| 2014/0051588 | A9 | 2/2014 | Drmanac et al. |
| 2014/0152801 | A1 | 6/2014 | Fine et al. |
| 2015/0079596 | A1 | 3/2015 | Eltoukhy et al. |
| 2015/0117784 | A1 | 4/2015 | Lin et al. |
| 2015/0169824 | A1 | 6/2015 | Kermani et al. |
| 2016/0042511 | A1 | 2/2016 | Chukka et al. |
| 2016/0078272 | A1 | 3/2016 | Hammoud |
| 2016/0110498 | A1 | 4/2016 | Bruand et al. |
| 2016/0196479 | A1 | 7/2016 | Chertok et al. |
| 2016/0350914 | A1 | 12/2016 | Champlin et al. |
| 2016/0356715 | A1 | 12/2016 | Zhong et al. |
| 2016/0357903 | A1 | 12/2016 | Shendure et al. |
| 2016/0371431 | A1 | 12/2016 | Haque et al. |
| 2017/0044601 | A1 | 2/2017 | Crnogorac et al. |
| 2017/0098032 | A1 | 4/2017 | Desai et al. |
| 2017/0116520 | A1 | 4/2017 | Min et al. |
| 2017/0161545 | A1 | 6/2017 | Champlin et al. |
| 2017/0169313 | A1 | 6/2017 | Choi et al. |
| 2017/0249421 | A1 | 8/2017 | Eberle et al. |
| 2017/0249744 | A1 | 8/2017 | Wang et al. |
| 2017/0362634 | A1 | 12/2017 | Ota et al. |
| 2018/0075279 | A1 | 3/2018 | Gertych et al. |
| 2018/0107927 | A1 | 4/2018 | Frey |
| 2018/0114337 | A1 | 4/2018 | Li et al. |
| 2018/0189613 | A1 | 7/2018 | Wolf et al. |
| 2018/0195953 | A1 | 7/2018 | Langlois et al. |
| 2018/0201992 | A1 | 7/2018 | Wu et al. |
| 2018/0211001 | A1 | 7/2018 | Gopalan et al. |
| 2018/0274023 | A1 | 9/2018 | Belitz et al. |
| 2018/0305751 | A1 | 10/2018 | Vermaas et al. |
| 2018/0322327 | A1 | 11/2018 | Smith et al. |
| 2018/0330824 | A1 | 11/2018 | Athey |
| 2018/0334711 | A1 | 11/2018 | Kelley et al. |
| 2018/0334712 | A1 | 11/2018 | Singer et al. |
| 2018/0340234 | A1 | 11/2018 | Scafe et al. |
| 2019/0034586 | A1 | 1/2019 | Pirrotte et al. |
| 2019/0080450 | A1 | 3/2019 | Arar et al. |
| 2019/0107642 | A1 | 4/2019 | Farhadi Nia et al. |
| 2019/0114544 | A1 | 4/2019 | Sundaram et al. |
| 2019/0156915 | A1 | 5/2019 | Zhang et al. |
| 2019/0164010 | A1 | 5/2019 | Ma et al. |
| 2019/0164021 | A1* | 5/2019 | Heifets .......... G16B 40/00 |
| 2019/0170680 | A1 | 6/2019 | Sikora et al. |
| 2019/0180153 | A1 | 6/2019 | Buckler et al. |
| 2019/0213473 | A1 | 7/2019 | Dutta et al. |
| 2019/0237160 | A1 | 8/2019 | Rothberg et al. |
| 2019/0237163 | A1 | 8/2019 | Wang et al. |
| 2019/0244348 | A1 | 8/2019 | Buckler et al. |
| 2019/0266491 | A1 | 8/2019 | Gao et al. |
| 2019/0272638 | A1 | 9/2019 | Mouton et al. |
| 2019/0332118 | A1 | 10/2019 | Wang et al. |
| 2019/0392578 | A1 | 12/2019 | Chukka et al. |
| 2020/0027002 | A1 | 1/2020 | Hickson et al. |
| 2020/0054306 | A1 | 2/2020 | Mehanian et al. |
| 2020/0057838 | A1 | 2/2020 | Yekhanin et al. |
| 2020/0065675 | A1 | 2/2020 | Sundaram et al. |
| 2020/0125947 | A1 | 4/2020 | Park et al. |
| 2020/0176082 | A1 | 6/2020 | Massingham |
| 2020/0193597 | A1 | 6/2020 | Fan et al. |
| 2020/0226368 | A1 | 7/2020 | Bakalo et al. |
| 2020/0256856 | A1 | 8/2020 | Chou et al. |
| 2020/0302223 | A1 | 9/2020 | Dutta et al. |
| 2020/0302224 | A1 | 9/2020 | Jaganathan et al. |
| 2020/0302297 | A1 | 9/2020 | Jaganathan et al. |
| 2020/0302603 | A1 | 9/2020 | Barnes et al. |
| 2020/0320294 | A1 | 10/2020 | Mangal et al. |
| 2020/0342955 | A1 | 10/2020 | Guo et al. |
| 2020/0364565 | A1 | 11/2020 | Kostem |
| 2020/0388029 | A1 | 12/2020 | Saltz et al. |
| 2021/0027462 | A1 | 1/2021 | Bredno et al. |
| 2021/0027860 | A1* | 1/2021 | Zhang .......... G16B 15/20 |
| 2021/0056287 | A1 | 2/2021 | Schaumburg et al. |
| 2021/0072391 | A1 | 3/2021 | Li et al. |
| 2021/0089827 | A1 | 3/2021 | Kumagai et al. |

(56) References Cited

U.S. PATENT DOCUMENTS

| | | | |
|---|---|---|---|
| 2021/0104331 A1* | 4/2021 | Mysore | G16H 70/40 |
| 2021/0115490 A1 | 4/2021 | Embree et al. | |
| 2021/0390278 A1 | 12/2021 | Van Leeuwen et al. | |

FOREIGN PATENT DOCUMENTS

| | | |
|---|---|---|
| CN | 110245685 A | 9/2019 |
| EP | 3130681 A1 | 2/2017 |
| EP | 3373238 A1 | 9/2018 |
| JP | 2007199397 A | 8/2007 |
| WO | 9106678 A1 | 5/1991 |
| WO | 2004018497 A2 | 3/2004 |
| WO | 2005065814 A1 | 7/2005 |
| WO | 2006064199 A1 | 6/2006 |
| WO | 2007010251 A2 | 1/2007 |
| WO | 2007123744 A2 | 11/2007 |
| WO | 2008154317 A1 | 12/2008 |
| WO | 2012058096 A1 | 5/2012 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Sundaram, L., Gao, H., Padigepati, S. R., McRae, J. F., Li, Y., Kosmicki, J. A., . . . & Farh, K. K. H. (2018). Predicting the clinical impact of human mutation with deep neural networks. Nature genetics, 50(8), 1161-1170. (Year: 2018).*

Townshend, R., Bedi, R., Suriana, P., & Dror, R. (2019). End-to-end learning on 3d protein structure for interface prediction. Advances in Neural Information Processing Systems, 32. (Year: 2019).*

Li, B., Yang, Y. T., Capra, J. A., & Gerstein, M. B. (2020). Predicting changes in protein thermodynamic stability upon point mutation with deep 3D convolutional neural networks. PLoS computational biology, 16(11), e1008291. (Year: 2020).*

Zhang, Y., Chen, Y., Wang, C., Lo, C. C., Liu, X., Wu, W., & Zhang, J. (2020). ProDCoNN: Protein design using a convolutional neural network. Proteins: Structure, Function, and Bioinformatics, 88(7), 819-829. (Year: 2020).*

Golkov, V., Skwark, M. J., Mirchev, A., Dikov, G., Geanes, A. R., Mendenhall, J., . . . & Cremers, D. (Nov. 2020). 3D deep learning for biological function prediction from physical fields. In 2020 International Conference on 3D Vision (3DV) (pp. 928-937). IEEE. (Year: 2020).*

Payandeh, J., Scheuer, T., Zheng, N. & Catterall, W. A. The crystal structure of a voltage-gated sodium channel. Nature 475, 353-358 (2011).

Shen, H. et al. Structure of a eukaryotic voltage-gated sodium channel at near-atomic resolution. Science 355, eaal4326 (2017), 19 pages.

Nakamura, K. et al. Clinical spectrum of SCN2A mutations expanding to Ohtahara syndrome. Neurology 81, 992-998 (2013).

Angermueller, Christof, et. al., "Deep learning for computational biology", Jun. 6, 2016, 16 pages.

Ioannidis, Nilah M., et al., "REVEL: An Ensemble Method for Predicting the Pathogenicity of Rare Missense Variants", Oct. 5, 2016, 9 pages.

He, Kaiming, et. al., "Deep Residual Learning for Image Recognition", Dec. 10, 2015, 12 pages.

Wolterink, Jelmer M., et. al., "Dilated Convolutional Neural Networks for Cardiovascular MR Segmentation in congenital Heart Disease", Apr. 12, 2017, 9 pages.

Van den Oord, Aaron, et. al., "Wavenet: A Generative Model for Raw Audio", Sep. 9, 2016, 15 pages.

Quang Daniel, et. al., "DANN: a deep learning approach for annotating the pathogenicity of genetic variants", Oct. 22, 2014, 3 pages.

PIQUERAS Autoregressive model based on a deep CNN for audio generation, Mar. 2017, 58pgs.

Srivastava, et al., "Highway Networks", Nov. 3, 2015 6pgs.

Sundaram, et al., "Predicting the clinical impact of human mutation with deep neural networks", Aug. 2018, 15pgs.

Szegedy, et. al., "Going deeper with convolutions", Sep. 17, 2014, 12pgs.

Wu "Intro to CNN", May 1, 2017, 31pgs.

Xiong, et. al., "The human splicing code reveals new insights into the genetic determinants of disease", Jan. 9, 2015, 20pgs.

Yue, et. al., "Deep Learning for Genomics:A Concise Overview from internet", May 8, 2018, 40pgs.

Yuen, et. al., "Genome wide characteristics of de novo mutations in autism", Jun. 1, 2016, 10pgs.

Yu, et. al., "Multi Scale Context Aggregation by Dilated Convolutions", Apr. 30, 2016, 13pgs.

Libbrecht, et. al., "Machine learning in genetics and genomics", Jan. 2, 2017, 30pgs.

Min, et. al., "Deep Learning in Bioinformatics", Jul. 25, 2016, 19 pgs.

Torng, Wen, et al., "3D deep convolutional neural networks for amino acid environment similarity analysis", 2017, 23pages.

Chen, Kathleen M., et al., "Selene: a PyTorch based deep learning library for sequence level data", Oct. 10, 2018, 15pages.

Grob, C., et. al., "Predicting variant deleteriousness in non human species Applying the CADD approach in mouse", 2018, 11 pages.

Li, et. al., "FoldingZero: Protein Folding from Scratch in Hydrophobic Polar Model", Dec. 3, 2018, 10 pages.

Rentzsch, et. al., "CADD: predicting the deleteriousness of variants throughout the human genome", Oct. 11, 2018, 9 pages.

Zou, etal, "A primer on deep learning in genomics", Nov. 26, 2018, 7pages.

Alberts, Bruce, et al., "Molecular biology of the cell", Sixth Edition, 2015, 3 pages.

PCT/US2018/055840—International Search Report and Written Opinion dated Jan. 25, 2019, 18 pages.

Wei etal_The Role of Balanced Training and Testing Data Sets for Binary Classifiers in Bioinformatics dated Jul. 9, 2013 12 pages.

PCT/US2018/055878—International Search Report and Written Opinion dated Jan. 22, 2019, 20 pages.

PCT/US2018/055881—International Search Report and Written Opinion dated Jan. 25, 2019, 17 pages.

Duggirala, Ravindranath, et.al., "Genome Mapping and Genomics in Human and Non Human Primate", 2015, 306pgs.

Brookes, Anthony J., "The essence of SNPs", 1999, pp. 177-186.

UniProtKB P04217 A1BG Human [retrieved on Mar. 13, 2019]. Retrieved from the Internet <https://www.uniprot.org/uniprot/P04217>, 12pages.

Bahar, Protein Actions Principles and Modeling, Chapter 7, 2017 pp. 165-166.

Dunbrack, Roland L., Re: Question about your Paper titled "The Role of Balanced Training and Testing Data Sets for Binary Classifiers in Bioinformatics", Message to Sikander Mohammed Khan, Feb. 3, 2019, E-mailm, 3pgs.

DbSNP rs2241788 [Retrieved on Mar. 13, 2019], Retrieved from the Internet<https://www.ncbi.nlm.nih.gov/snp/s2241788>, 5 pages.

Wei, et. al., "Prediction of phenotypes of missense mutations in human proteins from biological assemblies", Feb. 2013, 28 pages.

(56) References Cited

OTHER PUBLICATIONS

Zhang, Jun, and Bin Liu. "PSFM-DBT: identifying DNA-binding proteins by combing position specific frequency matrix and distance-bigram transformation." International journal of molecular sciences 18.9 (2017): 1856. (Year: 2017).
Gao, Tingting, et al. "Identifying translation initiation sites in prokaryotes using support vector machine." Journal of theoretical biology 262.4 (2010): 644-649. (Year: 2010).
Bi, Yingtao, et al. "Tree-based position weight matrix approach to model transcription factor binding site profiles." PloS one6.9 (2011): e24210. (Year: 2011).
Korhonen, Janne H., et al. "Fast motif matching revisited: high-order PWMs, SNPs and indels." Bioinformatics 33.4 (2016): 514-521. (Year: 2016).
Wong, Sebastien C., et al. "Understanding data augmentation for classification: when to warp?." 2016 international conference on digital image computing: techniques and applications (DICTA). IEEE, 2016. (Year: 2016).
Chang, Chia-Yun, et al. "Oversampling to overcome overfitting: exploring the relationship between data set composition, molecular descriptors, and predictive modeling methods." Journal of chemical information and modeling 53.4 (2013): 958-971.(Year: 2013).
Li, Gangmin, and Bei Yao. "Classification of Genetic Mutations for Cancer Treatment with Machine Learning Approaches." International Journal of Design, Analysis and Tools for Integrated Circuits and Systems 7.1 (2018): 63-67. (Year: 2018).
Martin-Navarro, Antonio, et al. "Machine learning classifier for identification of damaging missense mutations exclusive to human mitochondrial DNA-encoded polypeptides." BMC bioinformatics 18.1 (2017): 158. (Year: 2017).
Krizhevsky, Alex, et al, ImageNet Classification with Deep Convolutional Neural Networks, 2012, 9 Pages.
Geeks for Geeks, "Underfitting and Overfilling in Machine Learning", [retrieved on Aug. 26, 2019]. Retrieved from the Internet <https://www.geeksforgeeks.org/underfitting-and-overfitting-in-machine- -learning/>, 2 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
PCT/US2019031621—International Search Report and Written Opinion dated Aug. 7, 2019, 17 pages.
Carter et al., "Cancer-specific high-throughput annotation of somatic mutations: computational prediction of driver missense mutations," Cancer research 69, No. 16 (2009): pp. 6660-6667.
Min, et al., "Deep Learning in Bioinformatics", Jun. 19, 2016, 46pgs.
Jiminez et al., DeepSite: protein binding site predictor using 3D CNNs, dated Oct. 1, 2017, 7 pages.
U.S. Appl. No. 16/825,987, filed Mar. 20, 2020, U.S. Pat. No. 11,347,965, May 31, 2022, Issued.
U.S. Appl. No. 16/825,991, filed Mar. 20, 2020, U.S. Pat. No. 11,210,554, Dec. 28, 2021, Issued.
U.S. Appl. No. 16/826,126, filed Mar. 20, 2020, US-2020-0302297-A1, Sep. 24, 2020, Pending.
U.S. Appl. No. 16/826,134, filed Mar. 20, 2020, US-2020-0327377-A1, Oct. 15, 2020, Pending.
U.S. Appl. No. 16/826,168, filed Mar. 21, 2020, US-2020-0302224-A1, Sep. 24, 2020, Allowed.
U.S. Appl. No. 17/529,222, filed Nov. 17, 2021, US-2022-0147760-A1, May 12, 2022, Pending.
U.S. Appl. No. 17/827,612, filed May 27, 2022, Pending.
U.S. Appl. No. 16/874,633, filed May 14, 2020, US-2020-0364565-A1, Nov. 19, 2020, Allowed.
U.S. Appl. No. 17/703,975, filed Mar. 24, 2022, Pending.
U.S. Appl. No. 17/175,546, filed Feb. 12, 2021, US-2021-0265009-A1, Aug. 26, 2021, Pending.
U.S. Appl. No. 17/180,542, filed Feb. 19, 2021, US-2021-0265017-A1, Aug. 26, 2021, Pending.
U.S. Appl. No. 17/176,151, filed Feb. 15, 2021, US-2021-0265018-A1, Aug. 26, 2021, Pending.
U.S. Appl. No. 17/411,980, filed Aug. 25, 2021, US-2022-0067489-A1, Mar. 3, 2022, Pending.
U.S. Appl. No. 17/687,551, filed Mar. 4, 2022, Pending.
U.S. Appl. No. 17/687,583, filed Mar. 4, 2022, Pending.
U.S. Appl. No. 17/176,147, filed Feb. 15, 2021, US-2021-0265015-A1, Aug. 26, 2021, Pending.
U.S. Appl. No. 17/179,395, filed Feb. 18, 2021, US-2021-0265016-A1, Aug. 26, 2021, Pending.
U.S. Appl. No. 17/180,480, filed Feb. 19, 2021, US-2021-0264266-A1, Aug. 26, 2021, Pending.
U.S. Appl. No. 17/180,513, filed Feb. 19, 2021, US-2021-0264267-A1, Aug. 26, 2021, Pending.
U.S. Appl. No. 17/687,586, filed Mar. 4, 2022, Pending.
U.S. Appl. No. 17/468,411, filed Sep. 7, 2021, Allowed.
U.S. Appl. No. 17/830,287, filed Jun. 1, 2022, Pending.
U.S. Appl. No. 17/830,316, filed Jun. 1, 2022, Pending.
U.S. Appl. No. 17/839,331, filed Jun. 13, 2022, Pending.
U.S. Appl. No. 17/703,935, filed Mar. 24, 2022, Pending.
U.S. Appl. No. 17/703,958, filed Mar. 24, 2022, Pending.
PCT/US2022/24911, Apr. 14, 2022, Pending.
PCT/US2022/24913, Apr. 14, 2022, Pending.
PCT/US2020/024090, Mar. 21, 2020, WO 2020/191389, Sep. 24, 2020, Nationalized.
PCT/US2020/024087, Mar. 21, 2020, WO 2020/205296, Oct. 8, 2020, Nationalized.
PCT/US2020/024088, Mar. 21, 2020, WO 2020/191387, Sep. 24, 2020, Nationalized.
PCT/US2020/024091, Mar. 21, 2020, WO 2020/191390, Sep. 24, 2020, Nationalized.
PCT/US2020/024092, Mar. 22, 2020, WO 2020/191391, Sep. 24, 2020, Nationalized.
PCT/US2020/033280, May 15, 2020, WO 2020/232409, Nov. 19, 2020, Nationalized.
PCT/US2020/033281, May 15, 2020, WO 2020/232410, Nov. 19, 2020, Nationalized.
PCT/US2021/018258, Feb. 16, 2021, Pending.
PCT/US2021/018910, Feb. 19, 2021, Pending.
PCT/US2021/018422, Feb. 17, 2021, Pending.
PCT/US2021/047763, Aug. 26, 2021, Pending.
PCT/US2022/020460, Mar. 15, 2022, Pending.
PCT/US2022/020462, Mar. 15, 2022, Pending.
PCT/US2021/018427, Feb. 17, 2021, Pending.
PCT/US2021/018913, Feb. 19, 2021, Pending.
PCT/US2021/018915, Feb. 19, 2021, Pending.
PCT/US2021/018917, Feb. 19, 2021, Pending.
PCT/US2022/021814, Mar. 24, 2022, Pending.
PCT/US2022/035564, Jun. 29, 2022, Pending.
PCT/US2022/035567, Jun. 29, 2022, Pending.
PCT/US2022/035847, Jun. 30, 2022, Pending.
PCT/US2022/24916, Apr. 14, 2022, Pending.
PCT/US2022/24918, Apr. 14, 2022, Pending.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020] , Retrieved from <URL: https://support.illumina.com/training.html >, 13 pages.
MiSEQ: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/external_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.

(56) References Cited

OTHER PUBLICATIONS

Zhao et al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
PCT/US2020/24088 PCT Direct Letter, filed Mar. 21, 2020, 4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.
PCT/US2020/024088 Partial Search Report and Invitation to Pay Fees, dated Jul. 8, 2020, 22 pages.
Misiunas et. al., QuipuNet: convolutional neural network for single-molecule nanopore sensing, dated May 30, 2018, 7 pages.
Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.
PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
MiSEQ: Imaging and Base Calling: Illumina, Inc. Online Training Course, colored version, [retrieved on Oct. 11, 2020], Retrieved from <URL: https://support.illumina.com/training.html >, 9 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et al., Improved base-calling for the Illumina Genome Analyzer using Machine Learning Strategies, Genome Biology, published Aug. 14, 2009, 9 pages.
PCT/US2020/033281 Second Written Opinion, dated May 10, 2021, 8 pages.
PCT/US2021/018258 International Search Report and Written Opinion, dated May 26, 2021, 17 pages.
Smith et al., Barcoding and demultiplexing Oxford nanopore native RNA sequencing reads with deep residual learning, bioRxiv, dated Dec. 5, 2019, 18 pages.
PCT/US2021/018910 Partial Search Report and Invitation to pay fee, dated May 31, 2021, 14 pages.
PCT/US2021/018422 International Search Report and Written Opinion, dated Jun. 10, 2021, 12 pages.
Sundaram, L. et. al., "Predicitng the clinical impact of human mutation with deep neural networks", Nat. Genet. 50, 1161-1170 (2018).
Jaganathan, K. et. al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonic de novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates: why primates matter. Sci. Adv. 3, e1600946 (2017), 17 pages.

(56) References Cited

OTHER PUBLICATIONS

Kent, W. J. et al. The human genome browser at UCSC. Genome Res. 12, 996-1006 (2002).
Tyner, C. et al. The UCSC Genome Browser database: 2017 update. Nucleic Acids Res. 45, D626-D634 (2017).
Kabsch, W., & Sander, C. Dictionary of protein secondary structure: pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks. in 14th European Conference on Computer Vision—ECCV 2016. ECCV 2016. Lecture Notes in Computer Science, vol. 9908; 630 6, 15 (Springer, Cham, Switzerland; 2016).
Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0: a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability: an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB/Swiss-Prot: the ins and outs of expert manual curation. Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).
Stenson, P. D. et al. The Human Gene Mutation Database: building a comprehensive mutation repository for clinical and molecular genetics, diagnostic testing and personalized genomic medicine. Hum. Genet. 133, 1-9 (2014).

Alipanahi, et. al., "Predicting the Sequence Specificities of DNA and RNA Binding Proteins by Deep Learning", Aug. 2015, 9pgs.
Angermueller, et al., "Accurate Prediction of Single Cell DNA Methylation States Using Deep Learning", Apr. 11, 2017, 13pgs.
Arik, et al., "Deep Voice: Real time Neural Text to Speech", Mar. 7, 2017, 17pgs.
Ching, et al., "Opportunities and Obstacles for Deep Learning in Biology and Medicine", Jan. 19, 2018, 123pgs.
Ching, et al., "Opportunities and Obstacles for Deep Learning in Biology and Medicine", May 26, 2017, 47pgs.
Goodfellow, et. al., "Deep Learing Chapter 9 Convolutional Networks", 2016, 41 pgs.
Gu, et. al., "Recent Advances in Convolutional Neural Networks", Jan. 5, 2017, 37pgs.
Huang, et. al., "Densely Connected Convolutional Networks", Aug. 27, 2017, 9pgs.
Ioffe, et. al., "Batch Normalization: Accelerating Deep Network Training", Mar. 2, 2015, 11pgs.
Leung, et. al., "Deep learning of the tissue regulated splicing code", 2014, 9pgs.
Wang et. al., DeepDNA: a hybrid convolutional and recurrent neural network for compressing human mitochondrial genomes, IEEE International Conference on Bioinformatics and Biomedicine, 2018, 5 pages.
PCT/US2020/024092, International Preliminary Report on Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
PCT/US2020/033281, Second Article 34 Amendment Letter in response to Second Written Opinion, dated Jul. 10, 2021, 4 pages.
NL 2023311 NL Search Report, dated Mar. 24, 2020, 15 pages.
NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
MX/a/2020/014288 Response to First Office Action, dated May 5, 2021, 390 pages.
U.S. Appl. No. 16/825,991—Notice of Allowance dated Aug. 5, 2021, 10 pages.
Krishnakumar et. al., Systematic and stochastic influences on the performance of the MinION nanopore sequencer across a range of nucleotide bias, Scientific Reports, published Feb. 16, 2018, 13 pages.
Tegfalk, Application of Machine Learning techniques to perform base-calling in next-generation DNA sequencing, KTH Royal Institue of Technology, dated 2020, 53 pages.
U.S. Appl. No. 16/826,168—Office Action dated Aug. 31, 2021, 55 pages.
Kircher-etal_Improved-base-calling-for-the-Illumina-Genome-Analyzer-using-machine-learning-strategies_14August2009_10pages.
Albrecht et al., Deep learning for single molecule science, Nanotechnology, dated Sep. 18, 2017, 11 pages.
U.S. Appl. No. 16/825,987—Office Action (Quayle) dated Oct. 19, 2021, 85 pages.
PCT/US2021047763—International Search Report and Written Opinion, dated Dec. 20, 2021, 11 pages.
PCT/US2021/018422 Second Written Opinion, dated Feb. 4, 2022, 8 pages.
Adriana Romero et. al., FitNets: Hints for Thin Deep Nets, published Mar. 27, 2015, 13 pages.

(56) References Cited

OTHER PUBLICATIONS

U.S. Appl. No. 16/874,599—Notice of Allowance dated Dec. 3, 2021, 12 pages.
U.S. Appl. No. 16/825,987—Response to Office Action (Quayle) dated Oct. 19, 2021, filed Jan. 13, 2022, 11 pages.
U.S. Appl. No. 16/825,987—Notice of Allowance, dated Jan. 28, 2022, 12 pages.
U.S. Appl. No. 16/825,987—Supplemental Notice of Allowance, dated Feb. 7, 2022, 8 pages.
U.S. Appl. No. 16/826,168—Response to Office Action dated Aug. 31, 2021, filed Jan. 31, 2022, 15 pages.
CN 2020800036223—Voluntary Amendments, filed May 20, 2021, 26 pages.
EP 20719053.9—Rules 161(2) and 162 Communication, dated Oct. 28, 2021, 3 pages.
IL 279522—Notice Before Acceptance (in Hebrew), dated Aug. 1, 2021, 2 pages.
IL 279522—Response to Notice Before Acceptance dated Aug. 1, 2021, filed Nov. 28, 2021, 3 pages.
KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Notice Before Acceptance (in Hebrew), dated Aug. 1, 2021, 2 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Notice Before Examination (in Hebrew), dated Aug. 1, 2021, 2 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
Lutteropp, Error-Profile-Aware Correction of Next Generation Sequencing Reads, Karlsruhe Institute of Technology, dated Mar. 31, 2017, 96 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Bentley et. al., Accurate Whole Human Genome Sequencing using Reversible Terminator Chemistry, Nature, Nov. 2008, 21 pages.
Illumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et. al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et al., Chiron: translating nanopore raw signal directly into nucleotide sequence using deep learning, dated Aug. 23, 2017, 10 pages.
Stoiber et al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, bp 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.

(56) References Cited

OTHER PUBLICATIONS

Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Bentley et. al., Accurate Whole Human Genome Sequencing using Reversible Terminator Chemistry, Supplemental Information, Nature, dated Nov. 6, 2008, 55 pages, [retrieved on Jul. 21, 2021], retrieved from the internet [URL: https://media.nature.com/original/nature-assets/nature/journal/v456/n7218/extref/nature07517-s 1.pdf ].
Eraslan et. al., "Deep Learning: New computational modelling techniques for genomics", dated Jul. 2019, 15 pages.
Grange, NGS: the basics, Institut Jacques Monod, dated Jun. 26, 2000, 59 pages.
Illumina CMOS Chip and One-Channel SBS Chemistry, Illumina Inc, 2018, 4 pages.
Illumina, GA Bootcamp, Sequencing Module 3: Overview, Broad Institute, 73 pages, [retrieved on Jul. 22, 2021], Retrieved from [ URL: https://www.google.com/search?q=broad+institute+sequencing+module+3+overview&client=firefox-b1e&sxsrf=ALeKk02079LD_qrHqvhfFGRnNCUw8ZbQJA%3A1628296030482&ei=XtMNYYnpHMPi-gS61onoCQ&oq=broad+institute+sequencing+module+3+overview&gslcp=Cgdnd3Mtd216EAM6BwgjELADEC dKBQg6EgExSgQIQRgBUPn9AVj5QFg1ZQCaAFwAHgAgA~-.
Massingham et. al., All Your Base: a fast and accurate probabilistic approach to base calling, European Bioinformatics Institute, 22 pages, [retrieved on Jul. 22, 2021], Retrieved from the internet [URL: https://www.ebi.ac.uk/goldman-srv/AYB/references/ayb.pdf].
Python Implementation of the color map function for the PASCAL VOC data set, Github, 4 pages, retrieved on Jul. 23, 2021. Retrieved from [URL: https://gist.github.com/wllhf/a4533e0adebe57e3ed06d4b50c8419ae].
Semantic Segmentation Examples—MATLAB and Simulink, 22 pages, [retrieved on Jul. 21, 2021], Retrieved from the internet [URL: https://www.mathworks.com/help/vision/ug/semantic-segmentation-examples.html].
Hacteria Wiki, HiSeq2000—Next Level Hacking—Hackteria Wiki, retrieved on Apr. 12, 2021, retrieved from the internet [URL: https://www.hackteria.org/wiki/HiSeq2000_-_Next_Level_Hacking ], 42 pages.
Pei et al., A Topological Measurement for Weighted Protein Interaction Network, IEEE Computational Systems Bioinformatics Conference dated 2005, 11 pages.
Assfalg et. al., "3DString, A Feature String Kernel for 3D Object Classification on Voxelized Data", dated Nov. 6, 2006, 10 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.
Wang et. al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Report on Patentability, dated Jul. 23, 2021, 11 pages.
Pfeiffer et. al., Systematic evaluation of error rates and causes in short samples in next-generation sequencing, Scientific Reports, published Jul. 19, 2018, 14 pages.
PCT/US2020/033281—International Preliminary Report on Patentability, dated Aug. 31, 2021, 10 pages.
PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2021/018917—Second Written Opinion, dated Feb. 4, 2022, 7 pages.

(56) References Cited

OTHER PUBLICATIONS

PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silico Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Aggarwal, Neural Networks and Deep Learning: A Textbook, Springer, dated Aug. 26, 2018, 512 pages.
Wang et. al., Deep Neural Network Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.
PCT/US2021/018913 International Search Report and Written Opinion, dated Jun. 10, 2021, 11 pages.
Zeng et. al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et al., Efficient Processing of Deep Neural Networks: A Tutorial and Survey, Cornell University Library, dated Mar. 27, 2017, 21 pages.
Pu et. al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et al., "Predicting changes in protein thermostability upon mutation with deep 3D convolutional neural networks", dated Feb. 28, 2020, 21 pages.
Raschka et al., "Machine Learning and AI-based approaches for bioactive ligand discovery and GPCR-ligand recognition", dated Jun. 6, 2020, 33 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.

(56) References Cited

OTHER PUBLICATIONS

Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 14 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et al., FPGA-Accelerated 3rd Generation DNA Sequencing, in IEEE Transactions on Biomedical Circuits and Systems, vol. 14, Issue 1, Feb. 2020, pp. 65-74.
Prabhakar et al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et al., ShuffleNet: An Extremely Efficient Convolutional Neural Network for Mobile Devices, 2017.
He et. al., Deep Residual Learning for Image Recognition, in Proc. of CVPR, 2016.
Xie et al., Aggregated Residual Transformations for Deep Neural Networks, in Proc. of CVPR, 2017.
Howard et al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., WAVENET: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
Scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et. al., Image Segmentation with Watershed Algorithm, Revision 43532856, 2013, 6 pages. [retrieved on Jun. 8, 2021] Retrieved from the Internet <URL: https://opencv-python-tutroals.readthedocs.io/en/latest/py_tutorials/by_imgproc/py_watershed/py_watershed.html>.
Mzur, Watershed.py, Github, 3 pages. [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network, International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b>, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
PCT/US2020/024090 Article 34 Amendment, dated Dec. 4, 2020, 6 pages.
PCT/US2020/024090 Article 34 Amendment, dated Mar. 18, 2021, 3 pages.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).

(56) References Cited

OTHER PUBLICATIONS

Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants: a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project: 300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP: a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158 (2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP: the NCBI database of genetic variation. Nucleic Acids Res. 29, 308-311 (2001).
Schrago, C. G., & Russo, C. A. Timing the origin of New World monkeys. Mol. Biol. Evol. 20, 1620-1625 (2003).
Andrum, M. J. et al. ClinVar: public archive of interpretations of clinically relevant variants. Nucleic Acids Res. 44, D862-868 (2016).
Brandon, E. P., Idzerda, R. L. & McKnight, G. S. Targeting the mouse genome: a compendium of knockouts (Part II). Curr. Biol. 5, 758-765 (1995).
Lieschke, J. G. & Currie, P. D. Animal models of human disease: zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations: application to cancer genomics. Nucleic Acids Res. 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels. PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Peresini et. al., Nanopore Base Calling on the Edge, Bioinformatics, vol. 37, Issue 24, Dec. 2021, pp. 4661-4667, Published Jul. 27, 2021.

\* cited by examiner

Amino Acid-Wise Distance Channels—600

| Voxels | 1. A | 2. R | 3. N | 4. D | 5. C | 6. Q | 7. E | 8. G | 9. H | 10. I | 11. M | 12. L | 13. K | 14. F | 15. P | 16. S | 17. T | 18. W | 19. Y | 20. V | 21. * |
|---|---|---|---|---|---|---|---|---|---|---|---|---|---|---|---|---|---|---|---|---|---|
| (1, 1) | 1.55 | 0.34 | 3.49 | 0.71 | 2.8 | 4.9 | 0.25 | 0.15 | 0.59 | 1.8 | 2.5 | 3.2 | 4.7 | 0.61 | 2.72 | 5.4 | 1.5 | 2.4 | 0.36 | 2.9 | 4.2 |
| (1, 2) | 2.38 | 4.57 | 0.22 | 1.4 | 3.6 | 2.7 | 0.45 | 0.31 | 0.68 | 4.5 | 1.7 | 5.3 | 0.78 | 0.46 | 4.1 | 7.3 | 5.2 | 4.9 | 1.6 | 2.9 | 4.1 |
| (1, 3) | 5.16 | 1.77 | 0.38 | 0.84 | 1.22 | 2.3 | 0.56 | 0.28 | 0.41 | 3.7 | 1.85 | 4.52 | 0.92 | 3.12 | 1.98 | 5.21 | 3.53 | 1.34 | 0.47 | 8.9 | 3.3 |
| (2, 1) | 1.42 | 2.21 | 3.5 | 0.94 | 3.67 | 5.8 | 0.37 | 0.24 | 3.55 | 0.59 | 3.16 | 0.27 | 2.41 | 3.30 | 5.58 | 4.43 | 1.17 | 2.41 | 2.15 | 1.3 | 1.4 |
| (2, 2) | 4.27 | 0.36 | 1.38 | 4.54 | 3.15 | 4.92 | 1.25 | 2.33 | 0.60 | 1.82 | 2.66 | 3.25 | 2.72 | 5.99 | 4.21 | 1.26 | 1.35 | 3.15 | 3.36 | 2.7 | 1.1 |
| (2, 3) | 5.82 | 3.22 | 2.35 | 5.12 | 2.10 | 3.17 | 0.16 | 5.71 | 5.19 | 0.19 | 5.28 | 4.13 | 1.27 | 0.65 | 0.22 | 2.18 | 2.89 | 1.44 | 1.15 | 1.4 | 0.28 |
| (3, 1) | 2.19 | 4.34 | 1.19 | 3.15 | 1.56 | 2.16 | 1.25 | 3.25 | 4.22 | 1.86 | 5.52 | 3.14 | 0.42 | 4.29 | 1.34 | 3.36 | 3.81 | 0.44 | 0.28 | 4.9 | 1.22 |
| (3, 2) | 3.45 | 5.35 | 2.15 | 4.70 | 5.18 | 4.12 | 2.34 | 2.11 | 3.79 | 4.19 | 3.43 | 5.51 | 0.44 | 1.65 | 0.15 | 4.42 | 2.76 | 5.1 | 0.64 | 1.1 | 2.45 |
| (3, 3) | 1.35 | 2.98 | 1.17 | 0.70 | 3.2 | 3.16 | 3.27 | 6.56 | 1.16 | 5.25 | 2.75 | 2.12 | 1.24 | 0.27 | 1.72 | 5.41 | 1.53 | 1.15 | 0.71 | 0.77 | 3.90 |

Figure 6

| Amino Acids | One-Hot Encoded Variant-Experiencing Reference Amino Acid | One-Hot Encoded Variant/Alternative Amino Acid |
|---|---|---|
| | G | A |
| 1. Alanine (A) | 0 | 1 |
| 2. Arginine (R) | 0 | 0 |
| 3. Asparagine (N) | 0 | 0 |
| 4. Aspartic acid (D) | 0 | 0 |
| 5. Cysteine (C) | 0 | 0 |
| 6. Glutamine (Q) | 0 | 0 |
| 7. Glutamic acid (E) | 0 | 0 |
| 8. Glycine (G) | 1 | 0 |
| 9. Histidine (H) | 0 | 0 |
| 10. Isolucine (I) | 0 | 0 |
| 11. Methionine (M) | 0 | 0 |
| 12. Leucine (L) | 0 | 0 |
| 13. Lysine (K) | 0 | 0 |
| 14. Phenylalanine (F) | 0 | 0 |
| 15. Proline (P) | 0 | 0 |
| 16. Serine (S) | 0 | 0 |
| 17. Threonine (T) | 0 | 0 |
| 18. Tryptophan (W) | 0 | 0 |
| 19. Tyrosine (Y) | 0 | 0 |
| 20. Valine (V) | 0 | 0 |
| 21. GAP (*) | 0 | 0 |

Figure 8

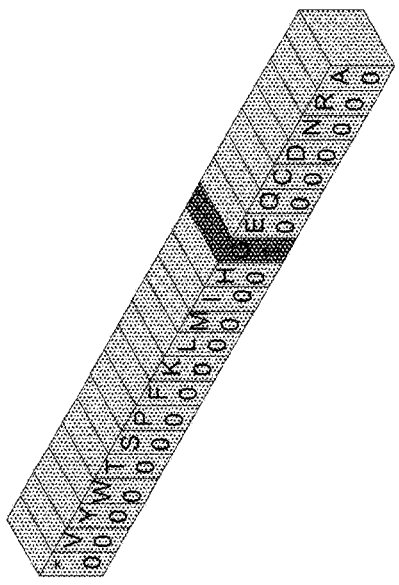
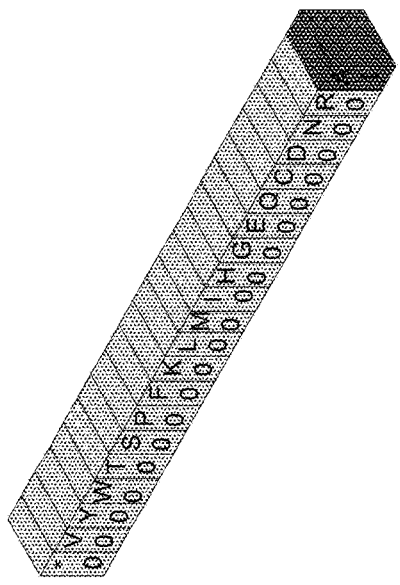
Figure 9

Voxels-to-Nearest Amino Acids Mapping — 1300

| Voxels 514 | Nearest Atoms 1302 | Nearest Reference Amino Acids 1312 |
|---|---|---|
| (1, 1) | Carbon$_\alpha^{15}$ | Aspartic acid (D)$^{15}$ |
| (1, 2) | Oxygen$^{27}$ | Arginine (R)$^{27}$ |
| (1, 3) | Hydrogen$^{14}$ | Isolucine (I)$^{14}$ |
| (2, 1) | Carbon$_\beta^{45}$ | Threonine (T)$^{45}$ |
| (2, 2) | Oxygen$^{22}$ | Tyrosine (Y)$^{22}$ |
| (2, 3) | Nitrogen$^{63}$ | Glycine (G)$^{63}$ |
| (3, 1) | Carbon$_\alpha^{38}$ | Tryptophan (W)$^{38}$ |
| (3, 2) | Carbon$_\beta^{5}$ | Valine (V)$^{5}$ |
| (3, 3) | Carbon$_\alpha^{23}$ | Proline (P)$^{23}$ |

Figure 13

Per-Voxel Evolutionary Profile Determination 1500

202

15th Position

| REF | ○ ○ ○ | Aspartic acid (D) | ○ ○ ○ |

| Primate Sequence 1 | ○ ○ ○ | Aspartic acid (D) | ○ ○ ○ |
| Primate Sequence 11 | ○ ○ ○ | Aspartic acid (D) | ○ ○ ○ |
| Mammal Sequence 1 | ○ ○ ○ | Aspartic acid (D) | ○ ○ ○ |
| Mammal Sequence 48 | ○ ○ ○ | Aspartic acid (D) | ○ ○ ○ |
| Vertebrate Sequence 1 | ○ ○ ○ | Aspartic acid (D) | ○ ○ ○ |
| Vertebrate Sequence 44 | ○ ○ ○ | Aspartic acid (D) | ○ ○ ○ |
| Vertebrate Sequence 45 | ○ ○ ○ | Valine (V) | ○ ○ ○ |
| Vertebrate Sequence 46 | ○ ○ ○ | Valine (V) | ○ ○ ○ |
| Vertebrate Sequence 47 | ○ ○ ○ | Valine (V) | ○ ○ ○ |
| Vertebrate Sequence 48 | ○ ○ ○ | Valine (V) | ○ ○ ○ |

Pan-Amino Acid Conservation Frequencies Sequence 1502

| | |
|---|---|
| A | 0 |
| R | 0 |
| N | 0 |
| D | .96 |
| C | 0 |
| Q | 0 |
| E | 0 |
| G | 0 |
| H | 0 |
| I | 0 |
| M | 0 |
| L | 0 |
| K | 0 |
| F | 0 |
| P | 0 |
| S | 0 |
| T | 0 |
| W | 0 |
| Y | 0 |
| V | .04 |
| * | 0 |

1504 → D row
1514 → * row

Figure 15

Voxels-to-Evolutionary Profiles Mapping — 1600

| Voxels (514) | Nearest Atoms (1302) | Nearest Reference Amino Acids (1312) | Per-Voxel Evolutionary Profiles (1602) | | | | | | | | | | | | | | | | | | | |
|---|---|---|---|---|---|---|---|---|---|---|---|---|---|---|---|---|---|---|---|---|---|---|
| | | | A | R | N | D | C | Q | E | G | H | I | M | L | K | F | P | S | T | W | Y | V | * |
| (1, 1) | Carbon$_\alpha$ 15 | Aspartic acid (D) 15 | 0 | 0 | 0 | .96 | 0 | 0 | 0 | 0 | 0 | 0 | 0 | 0 | 0 | 0 | 0 | 0 | 0 | 0 | 0 | .04 | 0 | — 1612 |
| (1, 2) | Oxygen 27 | Arginine (R) 27 | 0 | .88 | 0 | 0 | 0 | 0 | 0 | 0 | 0 | 0 | 0 | 0 | 0 | 0 | 0 | 0 | 0 | 0 | 0 | 0 | 0 | — 1622 |
| (1, 3) | Hydrogen 14 | Isolucine (I) 14 | 0 | 0 | 0 | 0 | 0 | 0 | 0 | 0 | 0 | .92 | 0 | 0 | 0 | 0 | 0 | 0 | 0 | 0 | 0 | 0 | 0 | — 1632 |
| (2, 1) | Carbon$_\beta$ 45 | Threonine (T) 45 | 0 | 0 | 0 | .16 | 0 | 0 | .08 | 0 | 0 | 0 | 0 | 0 | 0 | 0 | 0 | 0 | .84 | 0 | 0 | 0 | 0 | — 1642 |
| (2, 2) | Oxygen 22 | Tyrosine (Y) 22 | 0 | 0 | 0 | 0 | 0 | 0 | 0 | 0 | 0 | 0 | 0 | 0 | 0 | 0 | 0 | 0 | 0 | 0 | .97 | 0 | 0 | — 1652 |
| (2, 3) | Nitrogen 63 | Glycine (G) 63 | 0 | 0 | 0 | 0 | 0 | 0 | 0 | .77 | 0 | 0 | 0 | 0 | 0 | 0 | .23 | 0 | 0 | 0 | 0 | 0 | 0 | — 1662 |
| (3, 1) | Carbon$_\alpha$ 38 | Tryptophan (W) 38 | 0 | 0 | 0 | 0 | 0 | 0 | 0 | .15 | 0 | 0 | 0 | 0 | 0 | .05 | 0 | 0 | 0 | .95 | 0 | 0 | 0 | — 1672 |
| (3, 2) | Carbon$_\beta$ 5 | Valine (V) 5 | 0 | 0 | 0 | 0 | 0 | 0 | 0 | 0 | 0 | 0 | .25 | 0 | 0 | 0 | 0 | 0 | 0 | 0 | 0 | .85 | 0 | — 1682 |
| (3, 3) | Carbon$_\alpha$ 23 | Proline (P) 23 | 0 | 0 | 0 | 0 | 0 | 0 | 0 | 0 | 0 | 0 | 0 | 0 | 0 | 0 | .75 | 0 | 0 | 0 | 0 | 0 | 0 | — 1692 |

Figure 16

Efficient Voxelization 3200
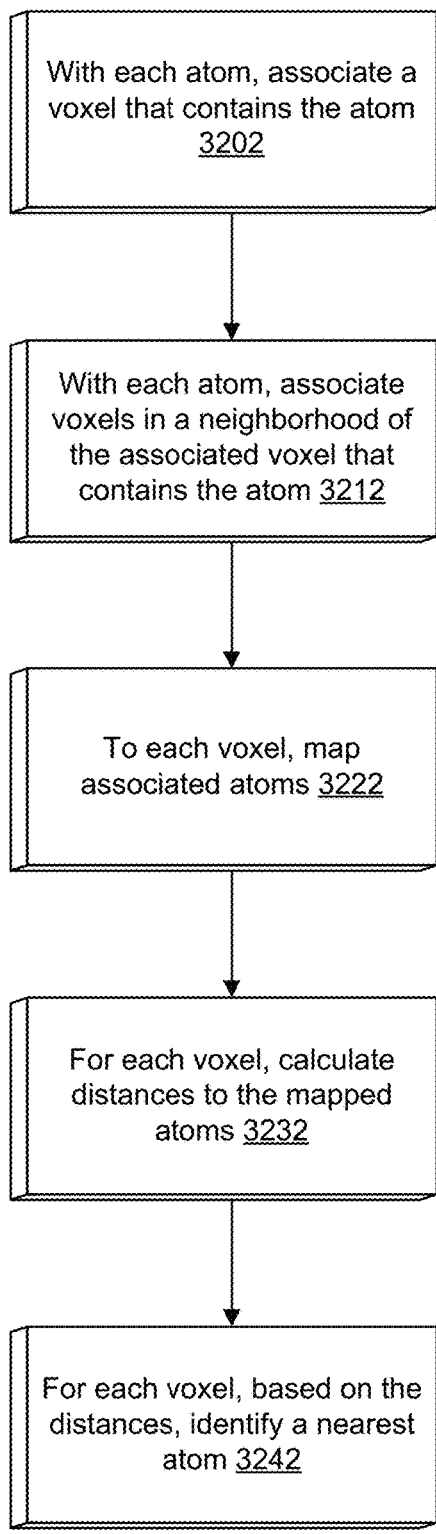
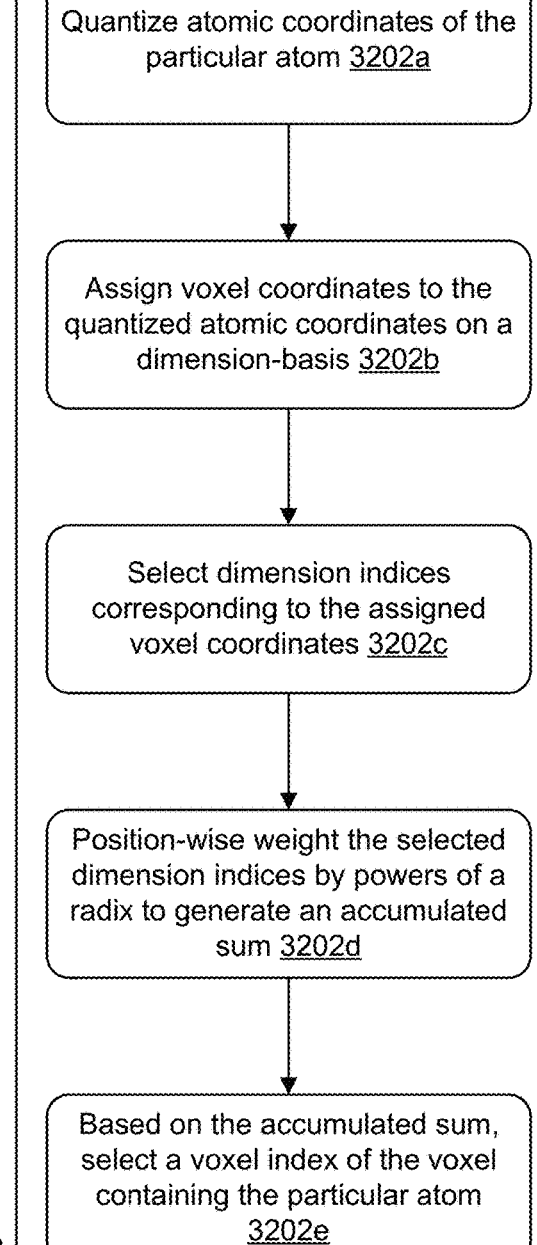
Figure 32A
Figure 32B

Atomic coordinates = (1.7456, 2.14323)

Step 1
Quantized atomic coordinates = (1.7, 2.1)

Step 2
Assign voxel coordinates = (1.5, 2.5)

Step 3
Select corresponding dimension indices = (1, 2)

Step 4
Generate accumulated sum = $1 \times 3^1 + 2 \times 3^0 = 5$

Step 5
Select voxel index = Voxel 5

| | 0 | 1 | 2 |
|---|---|---|---|
| 0 | Voxel 0 ⊕ (1,1) 0.5 | Voxel 1 0.5 ⊕ (1,2) 1.5 | Voxel 2 ⊕ (1,3) 2.5 |
| 1 | Voxel 3 ○ (2,1) | Voxel 4 1.5 ⊕ (2,2) | Voxel 5 ○ (2,3) |
| 2 | Voxel 6 ○ (3,1) | Voxel 7 2.5 ⊕ (3,2) | Voxel 8 ○ (3,3) |

Voxel Grid 522

First Dimension Indices   Second Dimension Indices
First Dimension Voxel Coordinates   Second Dimension Voxel Coordinates
Voxel Indices

Figure 33

ARTIFICIAL INTELLIGENCE-BASED ANALYSIS OF PROTEIN THREE-DIMENSIONAL (3D) STRUCTURES

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep convolutional neural networks to analyze multi-channel voxelized data.

INCORPORATIONS

The following are incorporated by reference for all purposes as if fully set forth herein:

Sundaram, L. et al. Predicting the clinical impact of human mutation with deep neural networks. Nat. Genet. 50, 1161-1170 (2018);

Jaganathan, K. et al. Predicting splicing from primary sequence with deep learning. Cell 176, 535-548 (2019);

U.S. Patent Application No. 62/573,144, titled "TRAINING A DEEP PATHOGENICITY CLASSIFIER USING LARGE-SCALE BENIGN TRAINING DATA," filed Oct. 16, 2017;

U.S. Patent Application No. 62/573,149, titled "PATHOGENICITY CLASSIFIER BASED ON DEEP CONVOLUTIONAL NEURAL NETWORKS (CNNs)," filed Oct. 16, 2017;

U.S. Patent Application No. 62/573,153, titled "DEEP SEMI-SUPERVISED LEARNING THAT GENERATES LARGE-SCALE PATHOGENIC TRAINING DATA," filed Oct. 16, 2017;

U.S. Patent Application No. 62/582,898, titled "PATHOGENICITY CLASSIFICATION OF GENOMIC DATA USING DEEP CONVOLUTIONAL NEURAL NETWORKS (CNNs)," filed Nov. 7, 2017;

U.S. patent application Ser. No. 16/160,903, titled "DEEP LEARNING-BASED TECHNIQUES FOR TRAINING DEEP CONVOLUTIONAL NEURAL NETWORKS," filed on Oct. 15, 2018;

U.S. patent application Ser. No. 16/160,986, titled "DEEP CONVOLUTIONAL NEURAL NETWORKS FOR VARIANT CLASSIFICATION," filed on Oct. 15, 2018;

U.S. patent application Ser. No. 16/160,968, titled "SEMI-SUPERVISED LEARNING FOR TRAINING AN ENSEMBLE OF DEEP CONVOLUTIONAL NEURAL NETWORKS," filed on Oct. 15, 2018; and U.S. patent application Ser. No. 16/407,149, titled "DEEP LEARNING-BASED TECHNIQUES FOR PRE-TRAINING DEEP CONVOLUTIONAL NEURAL NETWORKS," filed May 8, 2019.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genomics, in the broad sense, also referred to as functional genomics, aims to characterize the function of every genomic element of an organism by using genome-scale assays such as genome sequencing, transcriptome profiling and proteomics. Genomics arose as a data-driven science— it operates by discovering novel properties from explorations of genome-scale data rather than by testing preconceived models and hypotheses. Applications of genomics include finding associations between genotype and phenotype, discovering biomarkers for patient stratification, predicting the function of genes, and charting biochemically active genomic regions such as transcriptional enhancers.

Genomics data are too large and too complex to be mined solely by visual investigation of pairwise correlations. Instead, analytical tools are required to support the discovery of unanticipated relationships, to derive novel hypotheses and models and to make predictions. Unlike some algorithms, in which assumptions and domain expertise are hard coded, machine learning algorithms are designed to automatically detect patterns in data. Hence, machine learning algorithms are suited to data-driven sciences and, in particular, to genomics. However, the performance of machine learning algorithms can strongly depend on how the data are represented, that is, on how each variable (also called a feature) is computed. For instance, to classify a tumor as malign or benign from a fluorescent microscopy image, a preprocessing algorithm could detect cells, identify the cell type, and generate a list of cell counts for each cell type.

A machine learning model can take the estimated cell counts, which are examples of handcrafted features, as input features to classify the tumor. A central issue is that classification performance depends heavily on the quality and the relevance of these features. For example, relevant visual features such as cell morphology, distances between cells or localization within an organ are not captured in cell counts, and this incomplete representation of the data may reduce classification accuracy.

Deep learning, a subdiscipline of machine learning, addresses this issue by embedding the computation of features into the machine learning model itself to yield end-to-end models. This outcome has been realized through the development of deep neural networks, machine learning models that comprise successive elementary operations, which compute increasingly more complex features by taking the results of preceding operations as input. Deep neural networks are able to improve prediction accuracy by discovering relevant features of high complexity, such as the cell morphology and spatial organization of cells in the above example. The construction and training of deep neural networks have been enabled by the explosion of data, algorithmic advances, and substantial increases in computational capacity, particularly through the use of graphical processing units (GPUs).

The goal of supervised learning is to obtain a model that takes features as input and returns a prediction for a so-called target variable. An example of a supervised learning problem is one that predicts whether an intron is spliced out or not (the target) given features on the RNA such as the presence or absence of the canonical splice site sequence, the location of the splicing branchpoint or intron length. Training a machine learning model refers to learning its parameters, which commonly involves minimizing a loss function on training data with the aim of making accurate predictions on unseen data.

For many supervised learning problems in computational biology, the input data can be represented as a table with multiple columns, or features, each of which contains numerical or categorical data that are potentially useful for making predictions. Some input data are naturally represented as features in a table (such as temperature or time), whereas other input data need to be first transformed (such as deoxyribonucleic acid (DNA) sequence into k-mer counts) using a process called feature extraction to fit a tabular representation. For the intron-splicing prediction problem, the presence or absence of the canonical splice site sequence, the location of the splicing branchpoint and the intron length can be preprocessed features collected in a tabular format. Tabular data are standard for a wide range of supervised machine learning models, ranging from simple linear models, such as logistic regression, to more flexible nonlinear models, such as neural networks and many others.

Logistic regression is a binary classifier, that is, a supervised learning model that predicts a binary target variable. Specifically, logistic regression predicts the probability of the positive class by computing a weighted sum of the input features mapped to the [0,1] interval using the sigmoid function, a type of activation function. The parameters of logistic regression, or other linear classifiers that use different activation functions, are the weights in the weighted sum. Linear classifiers fail when the classes, for instance, that of an intron spliced out or not, cannot be well discriminated with a weighted sum of input features. To improve predictive performance, new input features can be manually added by transforming or combining existing features in new ways, for example, by taking powers or pairwise products.

Neural networks use hidden layers to learn these nonlinear feature transformations automatically. Each hidden layer can be thought of as multiple linear models with their output transformed by a nonlinear activation function, such as the sigmoid function or the more popular rectified-linear unit (ReLU). Together, these layers compose the input features into relevant complex patterns, which facilitates the task of distinguishing two classes.

Deep neural networks use many hidden layers, and a layer is said to be fully-connected when each neuron receives inputs from all neurons of the preceding layer. Neural networks are commonly trained using stochastic gradient descent, an algorithm suited to training models on very large data sets. Implementation of neural networks using modern deep learning frameworks enables rapid prototyping with different architectures and data sets. Fully-connected neural networks can be used for a number of genomics applications, which include predicting the percentage of exons spliced in for a given sequence from sequence features such as the presence of binding motifs of splice factors or sequence conservation; prioritizing potential disease-causing genetic variants; and predicting cis-regulatory elements in a given genomic region using features such as chromatin marks, gene expression and evolutionary conservation.

Local dependencies in spatial and longitudinal data must be considered for effective predictions. For example, shuffling a DNA sequence or the pixels of an image severely disrupts informative patterns. These local dependencies set spatial or longitudinal data apart from tabular data, for which the ordering of the features is arbitrary. Consider the problem of classifying genomic regions as bound versus unbound by a particular transcription factor, in which bound regions are defined as high-confidence binding events in chromatin immunoprecipitation following by sequencing (ChIP-seq) data. Transcription factors bind to DNA by recognizing sequence motifs. A fully-connected layer based on sequence-derived features, such as the number of k-mer instances or the position weight matrix (PWM) matches in the sequence, can be used for this task. As k-mer or PWM instance frequencies are robust to shifting motifs within the sequence, such models could generalize well to sequences with the same motifs located at different positions. However, they would fail to recognize patterns in which transcription factor binding depends on a combination of multiple motifs with well-defined spacing. Furthermore, the number of possible k-mers increases exponentially with k-mer length, which poses both storage and overfitting challenges.

A convolutional layer is a special form of fully-connected layer in which the same fully-connected layer is applied locally, for example, in a 6 bp window, to all sequence positions. This approach can also be viewed as scanning the sequence using multiple PWMs, for example, for transcription factors GATA1 and TAL1. By using the same model parameters across positions, the total number of parameters is drastically reduced, and the network is able to detect a motif at positions not seen during training. Each convolutional layer scans the sequence with several filters by producing a scalar value at every position, which quantifies the match between the filter and the sequence. As in fully-connected neural networks, a nonlinear activation function (commonly ReLU) is applied at each layer. Next, a pooling operation is applied, which aggregates the activations in contiguous bins across the positional axis, commonly taking the maximal or average activation for each channel. Pooling reduces the effective sequence length and coarsens the signal. The subsequent convolutional layer composes the output of the previous layer and is able to detect whether a GATA1 motif and TAL1 motif were present at some distance range. Finally, the output of the convolutional layers can be used as input to a fully-connected neural network to perform the final prediction task. Hence, different types of neural network layers (e.g., fully-connected layers and convolutional layers) can be combined within a single neural network.

Convolutional neural networks (CNNs) can predict various molecular phenotypes on the basis of DNA sequence alone. Applications include classifying transcription factor binding sites and predicting molecular phenotypes such as chromatin features, DNA contact maps, DNA methylation, gene expression, translation efficiency, RBP binding, and microRNA (miRNA) targets. In addition to predicting molecular phenotypes from the sequence, convolutional neural networks can be applied to more technical tasks traditionally addressed by handcrafted bioinformatics pipelines. For example, convolutional neural networks can predict the specificity of guide RNA, denoise ChIP-seq, enhance Hi-C data resolution, predict the laboratory of origin from DNA sequences and call genetic variants. Convolutional neural networks have also been employed to model long-range dependencies in the genome. Although interacting regulatory elements may be distantly located on the unfolded linear DNA sequence, these elements are often proximal in the actual 3D chromatin conformation. Hence, modelling molecular phenotypes from the linear DNA sequence, albeit a crude approximation of the chromatin, can be improved by allowing for long-range dependencies and allowing the model to implicitly learn aspects of the 3D organization, such as promoter-enhancer looping. This is achieved by using dilated convolutions, which have a receptive field of up to 32 kb. Dilated convolutions also allow splice sites to be predicted from sequence using a receptive field of 10 kb, thereby enabling the integration of genetic sequence across distances as long as typical human introns (See Jaganathan, K. et al. Predicting splicing from primary sequence with deep learning. Cell 176, 535-548 (2019)).

Different types of neural network can be characterized by their parameter-sharing schemes. For example, fully-connected layers have no parameter sharing, whereas convolutional layers impose translational invariance by applying the same filters at every position of their input. Recurrent neural networks (RNNs) are an alternative to convolutional neural networks for processing sequential data, such as DNA sequences or time series, that implement a different parameter-sharing scheme. Recurrent neural networks apply the same operation to each sequence element. The operation takes as input the memory of the previous sequence element and the new input. It updates the memory and optionally emits an output, which is either passed on to subsequent layers or is directly used as model predictions. By applying the same model at each sequence element, recurrent neural networks are invariant to the position index in the processed sequence. For example, a recurrent neural network can detect an open reading frame in a DNA sequence regardless of the position in the sequence. This task requires the recognition of a certain series of inputs, such as the start codon followed by an in-frame stop codon.

The main advantage of recurrent neural networks over convolutional neural networks is that they are, in theory, able to carry over information through infinitely long sequences via memory. Furthermore, recurrent neural networks can naturally process sequences of widely varying length, such as mRNA sequences. However, convolutional neural networks combined with various tricks (such as dilated convolutions) can reach comparable or even better performances than recurrent neural networks on sequence-modelling tasks, such as audio synthesis and machine translation. Recurrent neural networks can aggregate the outputs of convolutional neural networks for predicting single-cell DNA methylation states, RBP binding, transcription factor binding, and DNA accessibility. Moreover, because recurrent neural networks apply a sequential operation, they cannot be easily parallelized and are hence much slower to compute than convolutional neural networks.

Each human has a unique genetic code, though a large portion of the human genetic code is common for all humans. In some cases, a human genetic code may include an outlier, called a genetic variant, that may be common among individuals of a relatively small group of the human population. For example, a particular human protein may comprise a specific sequence of amino acids, whereas a variant of that protein may differ by one amino acid in the otherwise same specific sequence.

Genetic variants may be pathogenetic, leading to diseases. Though most of such genetic variants have been depleted from genomes by natural selection, an ability to identify which genetic variants are likely to be pathogenic can help researchers focus on these genetic variants to gain an understanding of the corresponding diseases and their diagnostics, treatments, or cures. The clinical interpretation of millions of human genetic variants remains unclear. Some of the most frequent pathogenic variants are single nucleotide missense mutations that change the amino acid of a protein. However, not all missense mutations are pathogenic.

Models that can predict molecular phenotypes directly from biological sequences can be used as in silico perturbation tools to probe the associations between genetic variation and phenotypic variation and have emerged as new methods for quantitative trait loci identification and variant prioritization. These approaches are of major importance given that the majority of variants identified by genome-wide association studies of complex phenotypes are non-coding, which makes it challenging to estimate their effects and contribution to phenotypes. Moreover, linkage disequilibrium results in blocks of variants being co-inherited, which creates difficulties in pinpointing individual causal variants. Thus, sequence-based deep learning models that can be used as interrogation tools for assessing the impact of such variants offer a promising approach to find potential drivers of complex phenotypes. One example includes predicting the effect of non-coding single-nucleotide variants and short insertions or deletions (indels) indirectly from the difference between two variants in terms of transcription factor binding, chromatin accessibility or gene expression predictions. Another example includes predicting novel splice site creation from sequence or quantitative effects of genetic variants on splicing.

End-to-end deep learning approaches for variant effect predictions are applied to predict the pathogenicity of missense variants from protein sequence and sequence conservation data (See Sundaram. L. et al. Predicting the clinical impact of human mutation with deep neural networks. Nat. Genet. 50, 1161-1170 (2018), referred to herein as "PrimateAI"). PrimateAI uses deep neural networks trained on variants of known pathogenicity with data augmentation using cross-species information. In particular, PrimateAI uses sequences of wild-type and mutant proteins to compare the difference and decide the pathogenicity of mutations using the trained deep neural networks. Such an approach which utilizes the protein sequences for pathogenicity prediction is promising because it can avoid the circularity problem and overfitting to previous knowledge. However, compared to the adequate number of data to train the deep neural networks effectively, the number of clinical data available in ClinVar is relatively small. To overcome this data scarcity, PrimateAI uses common human variants and variants from primates as benign data while simulated variants based on trinucleotide context were used as unlabeled data.

PrimateAI outperforms prior methods when trained directly upon sequence alignments. PrimateAI learns important protein domains, conserved amino acid positions, and sequence dependencies directly from the training data consisting of about 120,000 human samples. PrimateAI substantially exceeds the performance of other variant pathogenicity prediction tools in differentiating benign and pathogenic de-novo mutations in candidate developmental disorder genes, and in reproducing prior knowledge in ClinVar. These results suggest that PrimateAI is an important step forward for variant classification tools that may lessen the reliance of clinical reporting on prior knowledge.

Central to protein biology is the understanding of how structural elements give rise to observed function. The surfeit of protein structural data enables development of computational methods to systematically derive rules governing structural-functional relationships. However, performance of these methods depends critically on the choice of protein structural representation.

Protein sites are microenvironments within a protein structure, distinguished by their structural or functional role. A site can be defined by a three-dimensional (3D) location and a local neighborhood around this location in which the structure or function exists. Central to rational protein engineering is the understanding of how the structural arrangement of amino acids creates functional characteristics within protein sites. Determination of the structural and functional roles of individual amino acids within a protein provides information to help engineer and alter protein functions. Identifying functionally or structurally important amino acids allows focused engineering efforts such as site-directed mutagenesis for altering targeted protein functional properties. Alternatively, this knowledge can help avoid engineering designs that would abolish a desired function.

Since it has been established that structure is far more conserved than sequence, the increase in protein structural data provides an opportunity to systematically study the underlying pattern governing the structural-functional relationships using data-driven approaches. A fundamental aspect of any computational protein analysis is how protein structural information is represented. The performance of machine learning methods often depends more on the choice of data representation than the machine learning algorithm employed. Good representations efficiently capture the most critical information while poor representations create a noisy distribution with no underlying patterns.

The surfeit of protein structures and the recent success of deep learning algorithms provide an opportunity to develop tools for automatically extracting task specific representations of protein structures. Therefore, an opportunity arises to predict variant pathogenicity using multi-channel voxelized representations of 3D protein structures as input to deep neural networks.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 6 shows an example of twenty-one amino acid-wise distance channels, in accordance with one implementation of the technology disclosed.

FIG. 8 shows one-hot encodings of the reference amino acid and the alternative amino acid from FIG. 2, in accordance with one implementation of the technology disclosed.

FIG. 9 is a schematic diagram of a voxelized one-hot encoded reference amino acid and a voxelized one-hot encoded variant/alternative amino acid, in accordance with one implementation of the technology disclosed.

FIG. 13 illustrates voxels-to-nearest amino acids, in accordance with one implementation of the technology disclosed.

FIG. 15 shows an example of determining a pan-amino acid conservation frequencies sequence for a particular voxel, in accordance with one implementation of the technology disclosed.

FIG. 16 shows respective pan-amino acid conservation frequencies determined for respective voxels using the position frequency logic described in FIG. 15, in accordance with one implementation of the technology disclosed.

FIGS. 32A and 32B show the disclosed efficient voxelization process, in accordance with various implementations of the technology disclosed.

FIG. 33 depicts how atoms are associated with voxels that contain the atoms, in accordance with one implementation of the technology disclosed.

DETAILED DESCRIPTION

Figure 1:
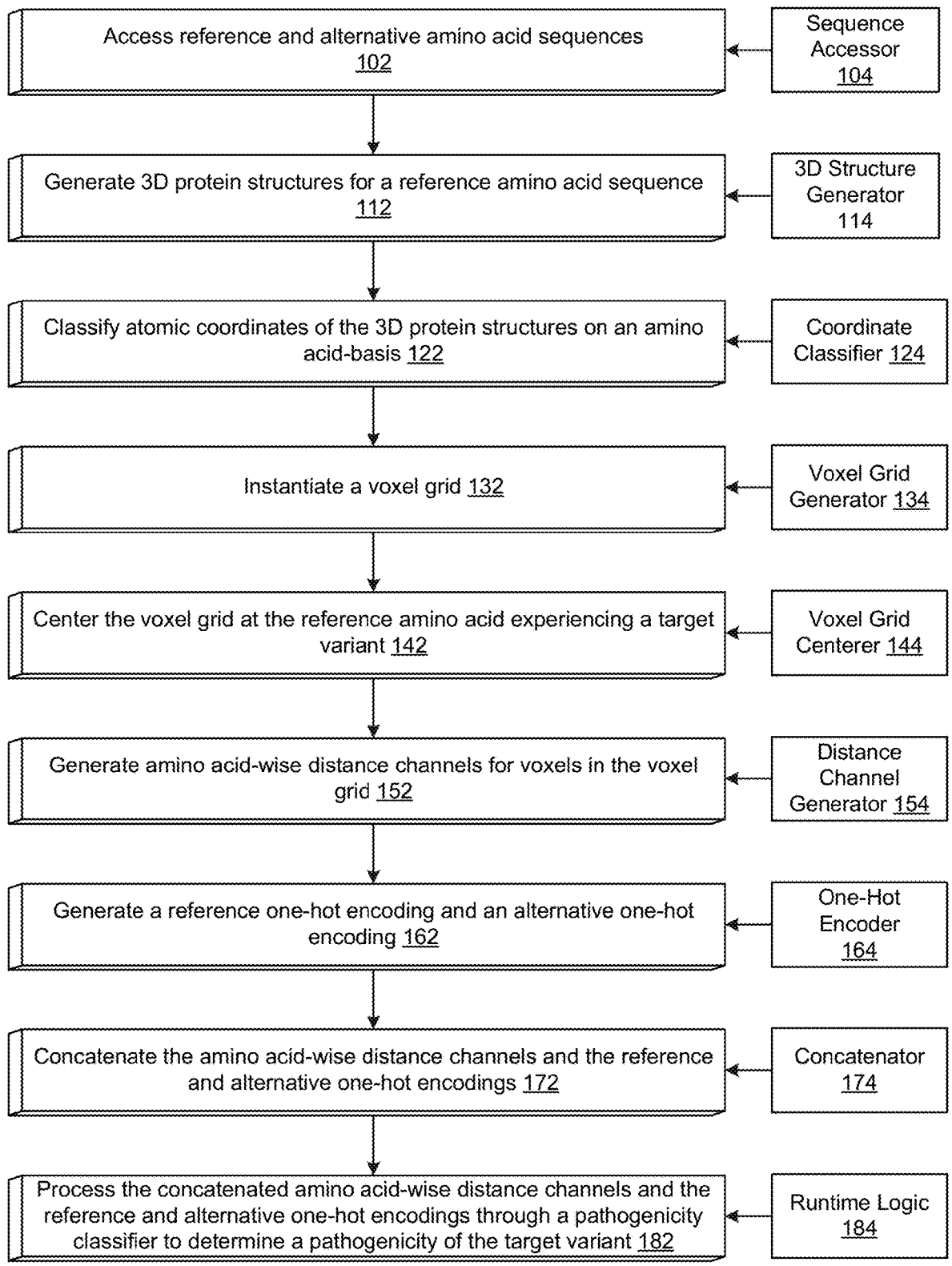
FIG. 1 is a flow diagram that illustrates a process of a system for determining pathogenicity of variants, according to various implementations of the technology disclosed.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

The detailed description of various implementations will be better understood when read in conjunction with the appended drawings. To the extent that the figures illustrate diagrams of the functional blocks of the various implementations, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various implementations are not limited to the arrangements and instrumentality shown in the drawings.

The processing engines and databases of the figures, designated as modules, can be implemented in hardware or software, and need not be divided up in precisely the same blocks as shown in the figures. Some of the modules can also be implemented on different processors, computers, or servers, or spread among a number of different processors, computers, or servers. In addition, it will be appreciated that some of the modules can be combined, operated in parallel or in a different sequence than that shown in the figures without affecting the functions achieved. The modules in the figures can also be thought of as flowchart steps in a method. A module also need not necessarily have all its code disposed contiguously in memory; some parts of the code can be separated from other parts of the code with code from other modules or other functions disposed in between.

Protein Structure-Based Pathogenicity Determination

FIG. 1 is a flow diagram that illustrates a process 100 of a system for determining pathogenicity of variants. At step 102, a sequence accessor 104 of the system accesses reference and alternative amino acid sequences. At 112, a 3D structure generator 114 of the system generates 3D protein structures for a reference amino acid sequence. In some implementations, the 3D protein structures are homology models of human proteins. In one implementation, a so-called SwissModel homology modelling pipeline provides a public repository of predicted human protein structures. In another implementation, a so-called HHpred homology modelling uses a tool called Modeller to predict the structure of a target protein from template structures.

Proteins are represented by a collection of atoms and their coordinates in 3D space. An amino acid can have a variety of atoms, such as carbon atoms, oxygen (O) atoms, nitrogen (N) atoms, and hydrogen (H) atoms. The atoms can be further classified as side chain atoms and backbone atoms. The backbone carbon atoms can include alpha-carbon ($C_\alpha$) atoms and beta-carbon ($C_\beta$) atoms.

At step 122, a coordinate classifier 124 of the system classifies 3D atomic coordinates of the 3D protein structures on an amino acid-basis. In one implementation, the amino acid-wise classification involves attributing the 3D atomic coordinates to the twenty-one amino acid categories (including stop or gap amino acid category). In one example, an amino acid-wise classification of alpha-carbon atoms can respectively list alpha-carbon atoms under each of the twenty-one amino acid categories. In another example, an amino acid-wise classification of beta-carbon atoms can respectively list beta-carbon atoms under each of the twenty-one amino acid categories.

In yet another example, an amino acid-wise classification of oxygen atoms can respectively list oxygen atoms under each of the twenty-one amino acid categories. In yet another example, an amino acid-wise classification of nitrogen atoms can respectively list nitrogen atoms under each of the twenty-one amino acid categories. In yet another example, an amino acid-wise classification of hydrogen atoms can respectively list hydrogen atoms under each of the twenty-one amino acid categories.

A person skilled in the art will appreciate that, in various implementations, the amino acid-wise classification can include a subset of the twenty-one amino acid categories and a subset of the different atomic elements.

At step 132, a voxel grid generator 134 of the system instantiates a voxel grid. The voxel grid can have any resolution, for example, 3×3×3, 5×5×5, 7×7×7, and so on. Voxels in the voxel grid can be of any size, for example, one angstrom (Å) on each side, two Å on each side, three Å on each side, and so on. One skilled in the art will appreciate that these example dimensions refer to cubic dimensions because voxels are cubes. Also, one skilled in the art will appreciate that these example dimensions are non-limiting, and the voxels can have any cubic dimensions.

At step 142, a voxel grid centerer 144 of the system centers the voxel grid at the reference amino acid experiencing a target variant at the amino acid level. In one implementation, the voxel grid is centered at an atomic coordinate of a particular atom of the reference amino acid experiencing the target variant, for example, the 3D atomic coordinate of the alpha-carbon atom of the reference amino acid experiencing the target variant.

Distance Channels

The voxels in the voxel grid can have a plurality of channels (or features). In one implementation, the voxels in the voxel grid have a plurality of distance channels (e.g., twenty-one distance channels for the twenty-one amino acid categories, respectively (including stop or gap amino acid category)). At step 152, a distance channel generator 154 of the system generates amino acid-wise distance channels for the voxels in the voxel grid. The distance channels are independently generated for each of the twenty-one amino acid categories.

Consider, for example, the Alanine (A) amino acid category. Further consider, for example, that the voxel grid is of size 3×3×3 and has twenty-seven voxels. Then, in one implementation, an Alanine distance channel includes twenty-seven distance values for the twenty-seven voxels in the voxel grid, respectively. The twenty-seven distance values in the Alanine distance channel are measured from respective centers of the twenty-seven voxels in the voxel grid to respective nearest atoms in the Alanine amino acid category.

In one example, the Alanine amino acid category includes only alpha-carbon atoms and therefore the nearest atoms are those Alanine alpha-carbon atoms that are most proximate to the twenty-seven voxels in the voxel grid, respectively. In another example, the Alanine amino acid category includes only beta-carbon atoms and therefore the nearest atoms are those Alanine beta-carbon atoms that are most proximate to the twenty-seven voxels in the voxel grid, respectively.

In yet another example, the Alanine amino acid category includes only oxygen atoms and therefore the nearest atoms are those Alanine oxygen atoms that are most proximate to the twenty-seven voxels in the voxel grid, respectively. In yet another example, the Alanine amino acid category includes only nitrogen atoms and therefore the nearest atoms are those Alanine nitrogen atoms that are most proximate to the twenty-seven voxels in the voxel grid, respectively. In yet another example, the Alanine amino acid category includes only hydrogen atoms and therefore the nearest atoms are those Alanine hydrogen atoms that are most proximate to the twenty-seven voxels in the voxel grid, respectively.

Like the Alanine distance channel, the distance channel generator 154 generates a distance channel (i.e., a set of voxel-wise distance values) for each of the remaining amino acid categories. In other implementations, the distance channel generator 154 generates distance channels only for a subset of the twenty-one amino acid categories.

In other implementations, the selection of the nearest atoms is not confined to a particular atom type. That is, within a subject amino acid category, the nearest atom to a particular voxel is selected, irrespective of the atomic element of the nearest atom, and the distance value for the particular voxel calculated for inclusion in the distance channel for the subject amino acid category.

In yet other implementations, the distance channels are generated on an atomic element-basis. Instead of or in addition to having the distance channels for the amino acid categories, distance values can be generated for atom element categories, irrespective of the amino acids to which the atoms belong. Consider, for example, that the atoms of amino acids in the reference amino acid sequence span seven atomic elements: carbon, oxygen, nitrogen, hydrogen, calcium, iodine, and sulfur. Then, the voxels in the voxel grid are configured to have seven distance channels, such that each of the seven distance channels have twenty-seven voxel wise distance values that specify distances to nearest atoms only within a corresponding atomic element category. In other implementations, distance channels for only a subset of the seven atomic elements can be generated. In yet other implementations, the atomic element categories and the distance channel generation can be further stratified into variations of a same atomic element, for example, alpha-carbon ($C_\alpha$) atoms and beta-carbon ($C_\beta$) atoms.

In yet other implementations, the distance channels can be generated on an atom type-basis, for example, distance channels only for side chain atoms and distance channels only for backbone atoms.

The nearest atoms can be searched within a predefined maximum scan radius from the voxel centers (e.g., six angstrom (Å)). Also, multiple atoms can be nearest to a same voxel in the voxel grid.

The distances are calculated between 3D coordinates of the voxel centers and 3D atomic coordinates of the atoms. Also, the distance channels are generated with the voxel grid centered at a same location (e.g., centered at the 3D atomic coordinate of the alpha-carbon atom of the reference amino acid experiencing the target variant).

The distances can be Euclidean distances. Also, the distances can be parameterized by atom size (or atom influence) (e.g., by using Lennard-Jones potential and/or Van der Waals atom radius of the atom in question). Also, the distance values can be normalized by the maximum scan radius, or by a maximum observed distance value of the furthest nearest atom within a subject amino acid category or a subject atomic element category or a subject atom type category. In some implementations, the distances between the voxels and the atoms are calculated based on polar coordinates of the voxels and the atoms. The polar coordinates are parameterized by angles between the voxels and the atoms. In one implementation, this angel information is used to generate an angle channel for the voxels (i.e., independent of the distance channels). In some implementations, angles between a nearest atom and neighboring atoms (e.g., backbone atoms) can be used as features that are encoded with the voxels.

Reference Allele and Alternative Allele Channels

The voxels in the voxel grid can also have reference allele and alternative allele channels. At step 162, a one-hot encoder 164 of the system generates a reference one-hot encoding of a reference amino acid in the reference amino acid sequence and an alternative one-hot encoding of an alternative amino acid in an alternative amino acid sequence. The reference amino acid experiences the target variant. The alternative amino acid is the target variant. The reference amino acid and the alternative amino acid are located at a same position respectively in the reference amino acid sequence and the alternative amino acid sequence. The reference amino acid sequence and the alternative amino acid sequence have the same position-wise amino acid composition with one exception. The exception is the position that has the reference amino acid in the reference amino acid sequence and the alternative amino acid in the alternative amino acid sequence.

At step 172, a concatenator 174 of the system concatenates the amino acid-wise distance channels and the reference and alternative one-hot encodings. In another implementation, the concatenator 174 concatenates the atomic element-wise distance channels and the reference and alternative one-hot encodings. In yet another implementation, the concatenator 174 concatenates the atomic type-wise distance channels and the reference and alternative one-hot encodings.

At step 182, runtime logic 184 of the system processes the concatenated amino acid-wise/atomic element-wise/atomic type-wise distance channels and the reference and alternative one-hot encodings through a pathogenicity classifier (pathogenicity determination engine) to determine a pathogenicity of the target variant, which is in turn inferred as a pathogenicity determination of the underlying nucleotide variant that creates the target variant at the amino acid level. The pathogenicity classifier is trained using labelled datasets of benign and pathogenic variants, for example, using the backpropagation algorithm. Additional details about the labelled datasets of benign and pathogenic variants and example architectures and training of the pathogenicity classifier can be found in commonly owned U.S. patent application Ser. Nos. 16/160,903; 16/160,986; 16/160,968; and Ser. No. 16/407,149.

Figure 2:
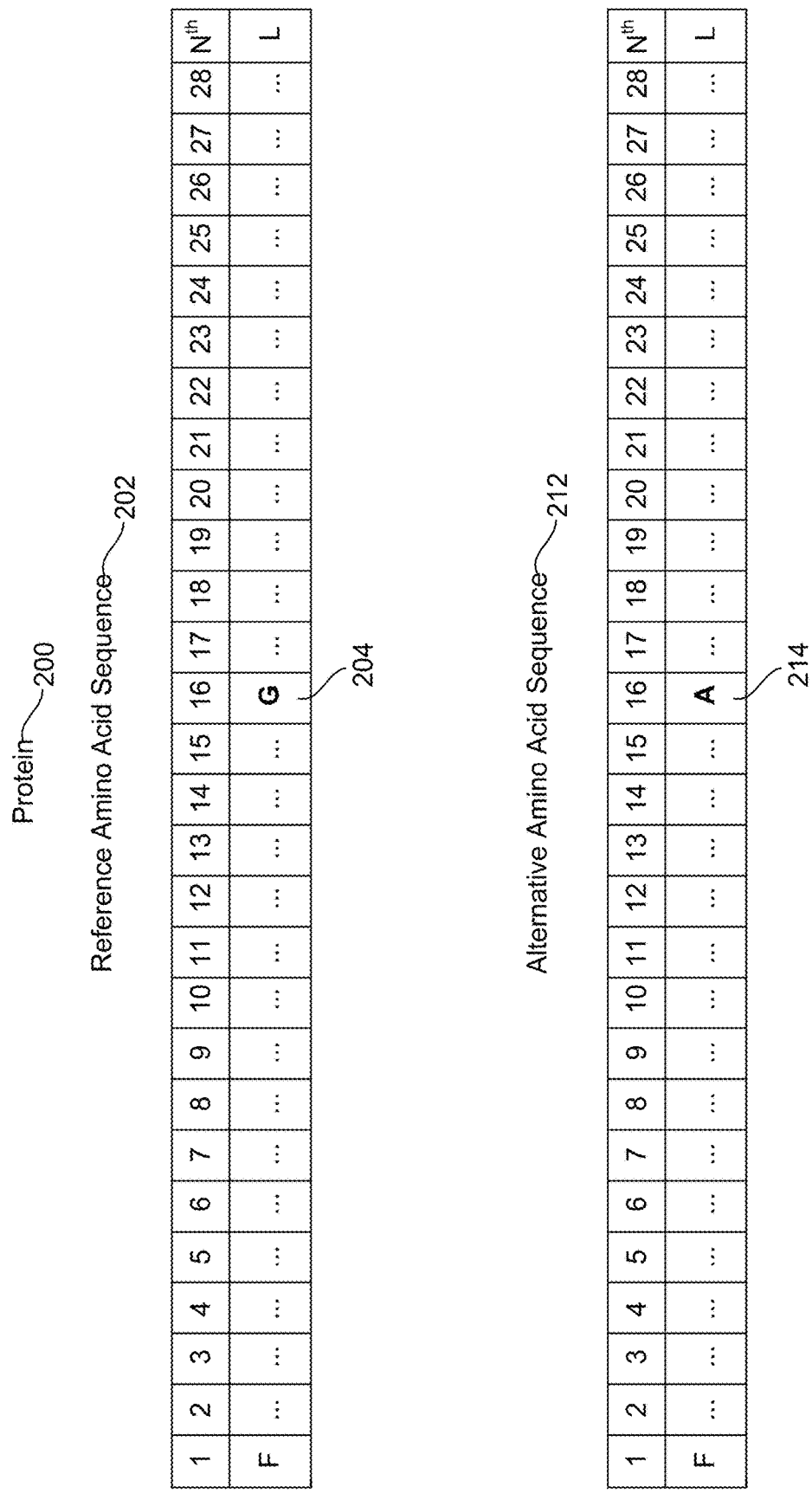
FIG. 2 schematically illustrates an example reference amino acid sequence of a protein and an alternative amino acid sequence of the protein, in accordance with one implementation of the technology disclosed.

FIG. 2 schematically illustrates a reference amino acid sequence 202 of a protein 200 and an alternative amino acid sequence 212 of the protein 200. The protein 200 comprises N amino acids. Positions of the amino acids in the protein 200 are labelled 1, 2, 3 . . . N. In the illustrated example, position 16 is the location that experiences an amino acid variant 214 (mutation) caused by an underlying nucleotide variant. For example, for the reference amino acid sequence 202, position 1 has reference amino acid Phenylalanine (F), position 16 has reference amino acid Glycine (G) 204, and position N (e.g., the last amino acid of the sequence 202) has reference amino acid Leucine (L). Though not illustrated for clarity, remaining positions in the reference amino acid sequence 202 contain various amino acids in an order that is specific to the protein 200. The alternative amino acid sequence 212 is the same as the reference amino acid sequence 202 except for the variant 214 at position 16, which contains the alternative amino acid Alanine (A) 214 instead of the reference amino acid Glycine (G) 204.

Figure 3:
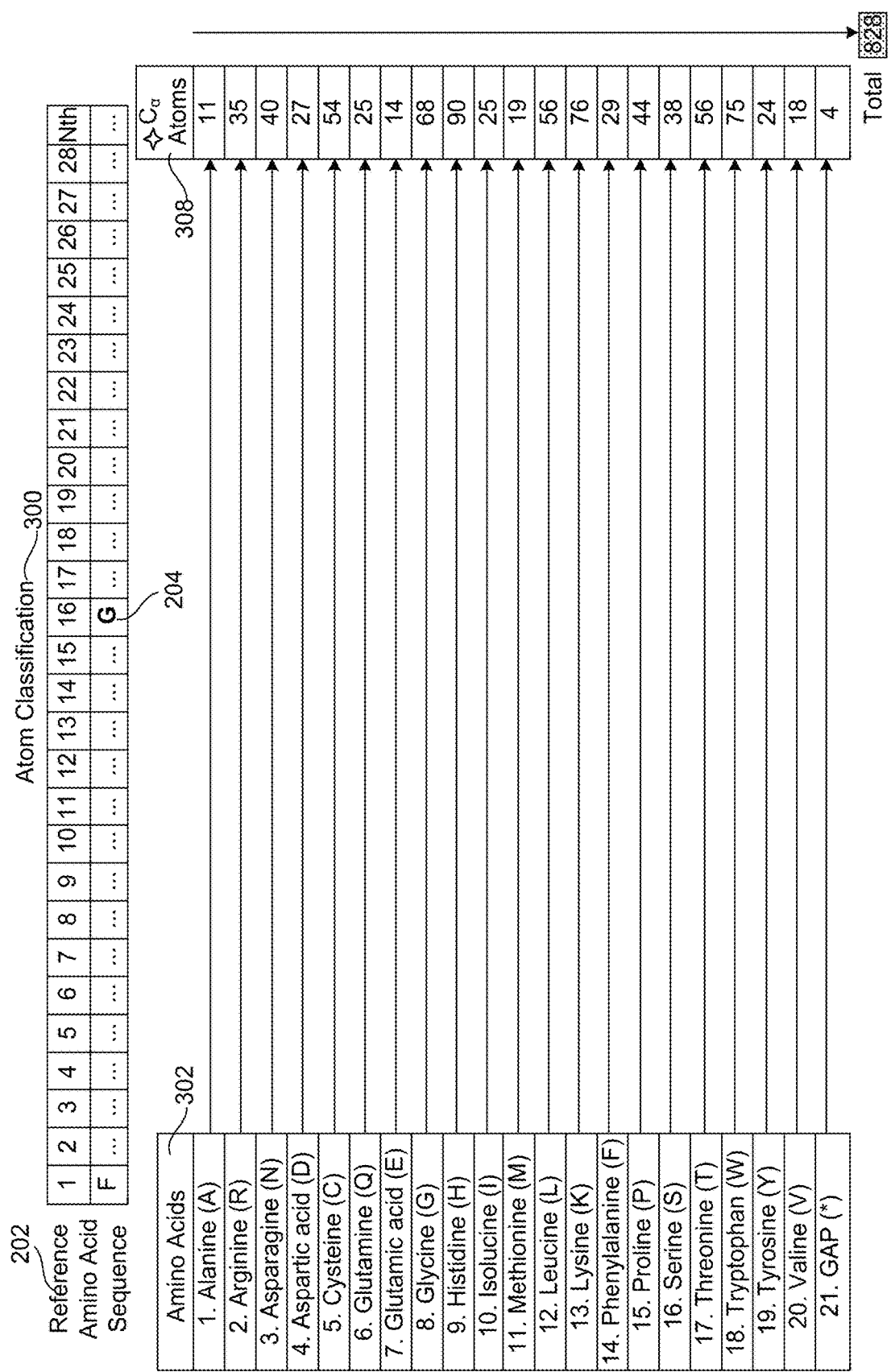
FIG. 3 illustrates amino acid-wise classification of atoms of amino acids in the reference amino acid sequence of FIG. 2, in accordance with one implementation of the technology disclosed.

FIG. 3 illustrates amino acid-wise classification of atoms of amino acids in the reference amino acid sequence 202, also referred to herein as "atom classification 300." Specific types of amino acids, among the twenty natural amino acids listed in column 302, may repeat in a protein. That is, a particular type of amino acid may occur more than once in a protein. Proteins may also have some undetermined amino acids that are categorized by a twenty-first stop or gap amino acid category. The right column in FIG. 3 contains counts of alpha-carbon ($C_\alpha$) atoms from different amino acids.

Specifically. FIG. 3 shows amino acid-wise classification of alpha-carbon ($C_\alpha$) atoms of the amino acids in the reference amino acid sequence 202. Column 308 of FIG. 3 lists the total number of alpha-carbon atoms observed for the reference amino acid sequence 202 in each of the twenty-one amino acid categories. For example, column 308 lists eleven alpha-carbon atoms observed for the Alanine (A) amino acid category. Since each amino acid has only one alpha-carbon atom, this means that Alanine occurs 11 times in the reference amino acid sequence 202. In another example, Arginine (R) occurs thirty-five times in the reference amino acid sequence 202. The total number of alpha-carbon atoms across the twenty-one amino acid categories is eight hundred and twenty-eight.

Figure 4:
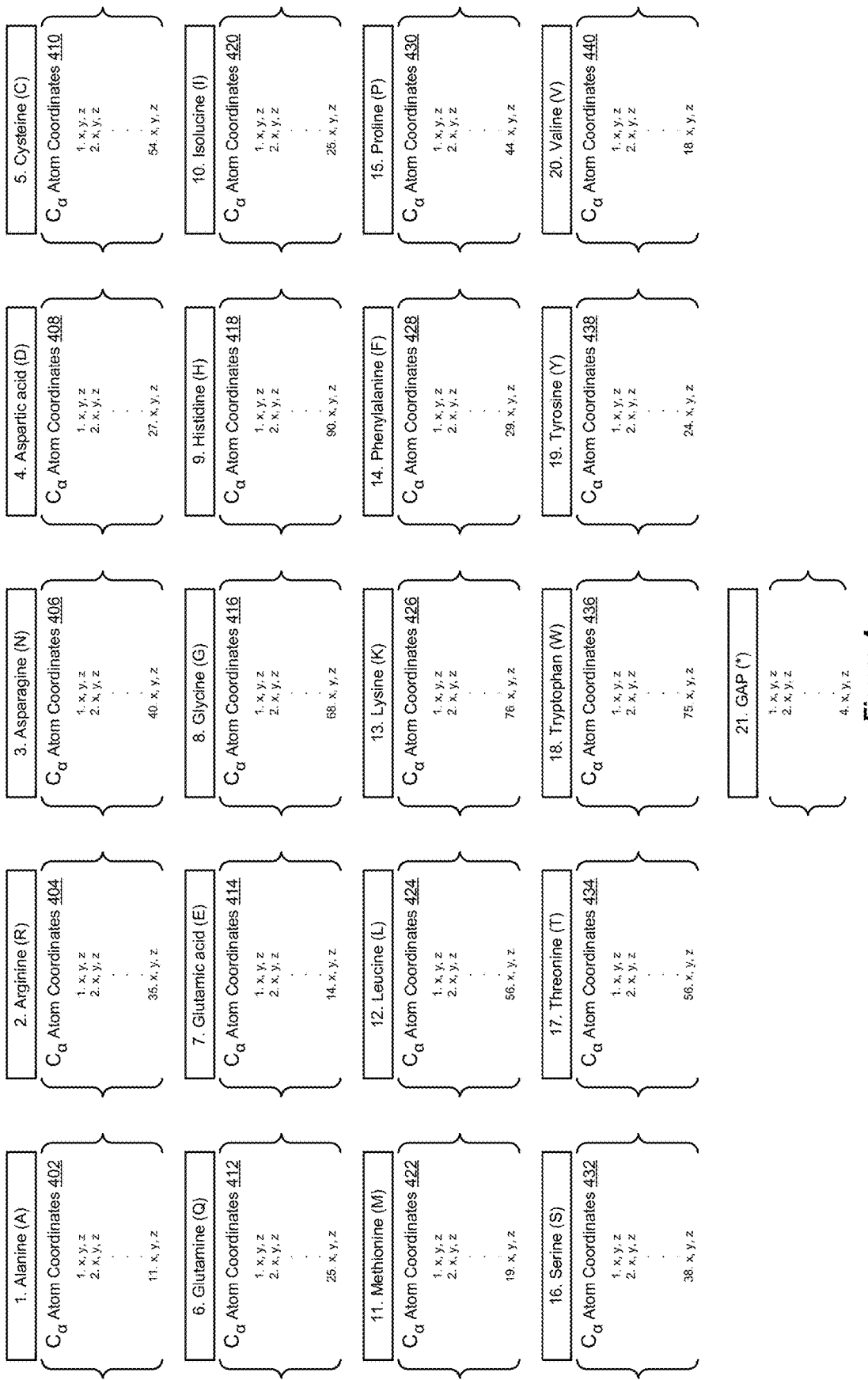
FIG. 4 illustrates amino acid-wise attribution of 3D atomic coordinates of the alpha-carbon atoms classified in FIG. 3 on an amino acid-basis, in accordance with one implementation of the technology disclosed.

FIG. 4 illustrates amino acid-wise attribution of 3D atomic coordinates of the alpha-carbon atoms of the reference amino acid sequence 202 based on the atom classification 300 in FIG. 3. This is referred to herein as "atomic coordinates bucketing 400." In FIG. 4, lists 404-440 tabulate the 3D atomic coordinates of the alpha-carbon atoms bucketed to each of the twenty-one amino acid categories.

In the illustrated implementation, the bucketing 400 in FIG. 4 follows the classification 300 of FIG. 3. For example, in FIG. 3, the Alanine amino acid category has eleven alpha-carbon atoms, and therefore, in FIG. 4, the Alanine amino acid category has eleven 3D atomic coordinates of the corresponding eleven alpha-carbon atoms from FIG. 3. This classification-to-bucketing logic flows from FIG. 3 to FIG. 4 for other amino acid categories too. However, this classification-to-bucketing logic is only for representational purposes, and, in other implementations, the technology disclosed need not perform the classification 300 and the bucketing 400 to locate the voxel-wise nearest atoms, and may perform fewer, additional, or different steps. For example, in some implementations, the technology disclosed can locate the voxel-wise nearest atoms by using a sort and search algorithm that returns the voxel-wise nearest atoms from one or more databases in response to a search query configured to accept query parameters like sort criteria (e.g., amino acid-wise, atomic element-wise, atom type-wise), the predefined maximum scan radius, and the type of distances (e.g., Euclidean, Mahalanobis, normalized, unnormalized). In various implementations of the technology disclosed, a plurality of sort and search algorithms from the current or future technical field can be analogous used by a person skilled in the art to locate the voxel-wise nearest atoms.

In FIG. 4, the 3D atomic coordinates are represented by cartesian coordinates x, y, z, but any type of coordinate system may be used, such as spherical or cylindrical coordinates, and claimed subject matter is not limited in this respect. In some implementations, one or more databases may include information regarding the 3D atomic coordinates of the alpha-carbon atoms and other atoms of amino acids in proteins. Such databases may be searchable by specific proteins.

As discussed above, the voxels and the voxel grid are 3D entities. However, for clarity's sake, the drawings depict, and the description discusses the voxels and the voxel grid in a two-dimensional (2D) format. For example, a 3×3×3 voxel grid of twenty-seven voxels is depicted and described herein as a 3×3 2D pixel grid with nine 2D pixels. A person skilled in the art will appreciate that the 2D format is used only for representational purposes and is intended to cover the 3D counterparts (i.e., 2D pixels represent 3D voxels and 2D pixel grid represents 3D voxel grid). Also, the drawings are also not scale. For example, voxels of size two angstrom (Å) are depicted using a single pixel.

Voxel-Wise Distance Calculation

Figure 5:
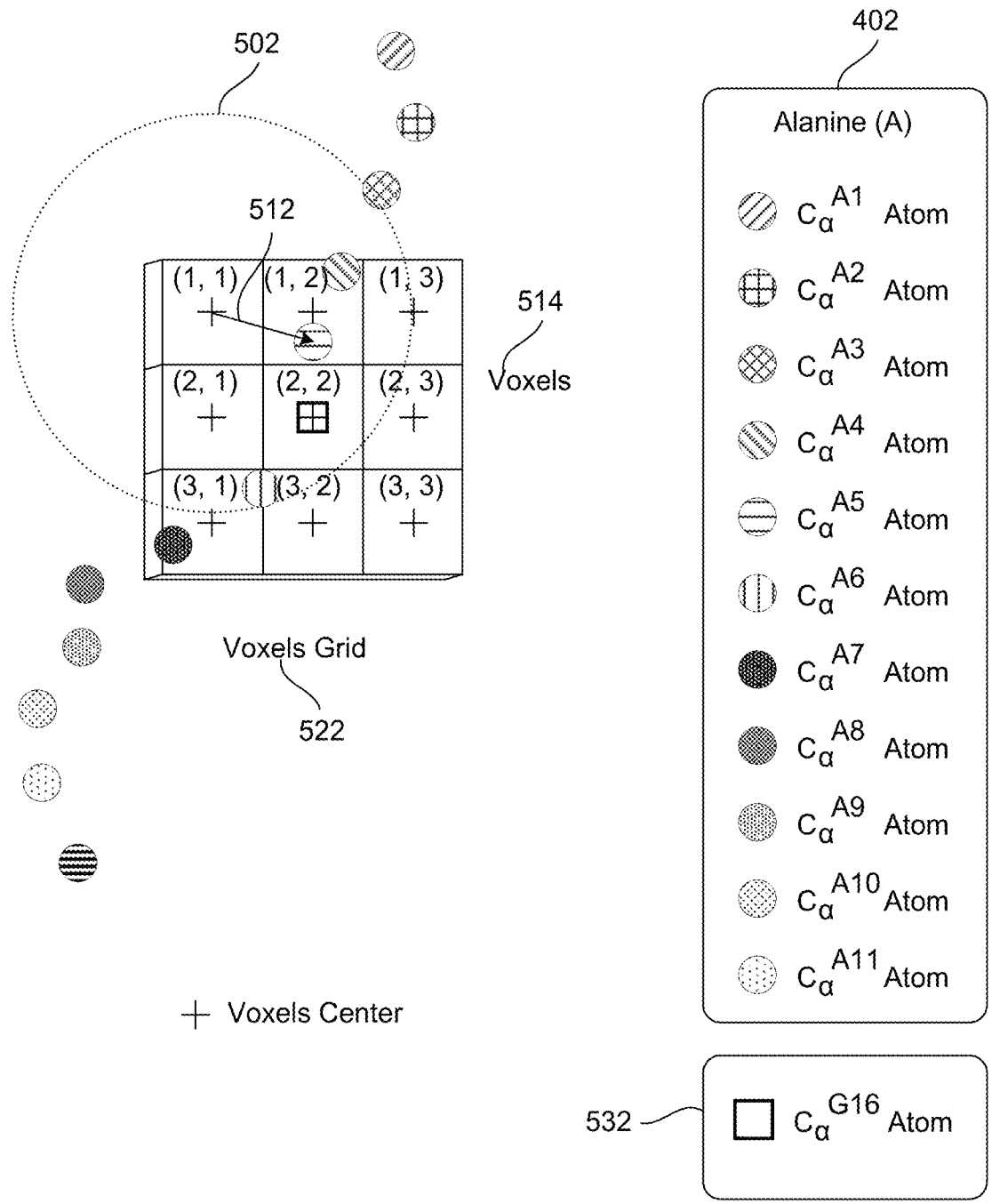
FIG. 5 schematically illustrates a process of determining voxel-wise distance values, in accordance with one implementation of the technology disclosed.

FIG. 5 schematically illustrates a process of determining voxel-wise distance values, also referred to herein as "voxel-wise distance calculation 500." In the illustrated example, the voxel-wise distance values are calculated only for the Alanine (A) distance channel. However, the same distance calculation logic is executed for each of the twenty-one amino acid categories to generate twenty-one amino acid-wise distance channels and can be further expanded to other atom types like beta-carbon atoms and other atomic elements like oxygen, nitrogen, and hydrogen, as discussed above with respect to FIG. 1. In some implementations, the atoms are randomly rotated prior to the distance calculation to make the training of the pathogenicity classifier invariant to atom orientation.

In FIG. 5, a voxel grid 522 has nine voxels 514 identified with indices (1, 1), (1, 2), (1, 3), (2, 1), (2, 2), (2, 3), (3, 1), (3, 2), and (3, 3). The voxel grid 522 is centered, for example, at the 3D atomic coordinate 532 of the alpha-carbon atom of the Glycine (G) amino acid at position 16 in the reference amino acid sequence 202 because, in the alternative amino acid sequence 212, the position 16 experiences the variant that mutates the Glycine (G) amino acid to the Alanine (A) amino acid, as discussed above with respect to FIG. 2. Also, the center of the voxel grid 522 coincides with the center of voxel (2, 2).

The centered voxel grid 522 is used for the voxel-wise distance calculation for each of the twenty-one amino acid-wise distance channels. Starting, for example, with the Alanine (A) distance channel, distances between the 3D coordinates of respective centers of the nine voxels 514 and the 3D atomic coordinates 402 of the eleven Alanine alpha-carbon atoms are measured to locate a nearest Alanine alpha-carbon atom for each of the nine voxels 514. Then, nine distance values for nine distances between the nine voxels 514 and the respective nearest Alanine alpha-carbon atoms are used to construct the Alanine distance channel. The resulting Alanine distance channel arranges the nine Alanine distance values in the same order as the nine voxels 514 in the voxel grid 522.

The above process is executed for each of the twenty-one amino acid categories. For example, the centered voxel grid 522 is similarly used to calculate the Arginine (R) distance channel, such that distances between the 3D coordinates of respective centers of the nine voxels 514 and the 3D atomic coordinates 404 of the thirty-five Arginine alpha-carbon atoms are measured to locate a nearest Arginine alpha-carbon atom for each of the nine voxels 514. Then, nine distance values for nine distances between the nine voxels 514 and the respective nearest Arginine alpha-carbon atoms are used to construct the Arginine distance channel. The resulting Arginine distance channel arranges the nine Arginine distance values in the same order as the nine voxels 514 in the voxel grid 522. The twenty-one amino acid-wise distance channels are voxel-wise encoded to form a distance channel tensor.

Specifically, in the illustrated example, a distance 512 is between the center of voxel (1, 1) of voxel grid 522 and the nearest alpha-carbon ($C_\alpha$) atom, which is the $C\alpha^{45}$ atom in list 402. Accordingly, the value assigned to voxel (1, 1) is the distance 512. In another example, the $C\alpha^{44}$ atom is the nearest Ca atom to the center of voxel (1, 2). Accordingly, the value assigned to voxel (1, 2) is the distance between the center of voxel (1, 2) and the $C\alpha^{44}$ atom. In still another example, the $C\alpha^{46}$ atom is the nearest Ca atom to the center of voxel (2, 1). Accordingly, the value assigned to voxel (2, 1) is the distance between the center of voxel (2, 1) and the $C\alpha^{46}$ atom. In still another example, the $C\alpha^{46}$ atom is also the nearest Ca atom to the center of voxels (3, 2) and (3, 3). Accordingly, the value assigned to voxel (3, 2) is the distance between the center of voxel (3, 2) and the $C\alpha^{46}$ atom and the value assigned to voxel (3, 3) is the distance between the center of voxel (3, 3) and the $C\alpha^{46}$ atom. In some implementations, the distance values assigned to the voxels 514 may be normalized distances. For example, the distance value assigned to voxel (1, 1) may be the distance 512 divided by a maximum distance 502 (predefined maximum scan radius). In some implementations, the nearest-atom distances may be Euclidean distances and the nearest-atom distances may be normalized by dividing the Euclidean distances with a maximum nearest-atom distance (e.g., such as the maximum distance 502).

As described above, for amino acids having alpha-carbon atoms, the distances may be nearest-alpha-carbon atom distances from corresponding voxel centers to nearest alpha-carbon atoms of the corresponding amino acids. Additionally, for amino acids having beta-carbon atoms, the distances may be nearest-beta-carbon atom distances from corresponding voxel centers to nearest beta-carbon atoms of the corresponding amino acids. Similarly, for amino acids having backbone atoms, the distances may be nearest-backbone atom distances from corresponding voxel centers to nearest backbone atoms of the corresponding amino acids. Similarly, for amino acids having sidechain atoms, the distances may be nearest-sidechain atom distances from corresponding voxel centers to nearest sidechain atoms of the corresponding amino acids. In some implementations, the distances additionally/alternatively can include distances to second, third, fourth nearest atoms, and so on.

Amino Acid-Wise Distance Channels

FIG. 6 shows an example of twenty-one amino acid-wise distance channels 600. Each column in FIG. 6 corresponds to a respective one of the twenty-one amino acid-wise distance channels 602-642. Each amino acid-wise distance channel comprises a distance value for each of the voxels 514 of the voxel grid 522. For example, the amino acid-wise distance channel 602 for Alanine (A) comprises distance values for respective ones of the voxels 514 of the voxel grid 522. As mentioned above, the voxel grid 522 is 3D grid of volume 3×3×3 and comprises twenty-seven voxels. Likewise, though FIG. 6 illustrates the voxels 514 in two dimensions (e.g., nine voxels of a 3×3 grid), each amino acid-wise distance channel may comprise twenty-seven voxel-wise distance values for the 3×3×3 voxel grid.

Directionality Encoding

In some implementations, the technology disclosed uses a directionality parameter to specify the directionality of the reference amino acids in the reference amino acid sequence 202. In some implementations, the technology disclosed uses the directionality parameter to specify the directionality of the alternative amino acids in the alternative amino acid sequence 212. In some implementations, the technology disclosed uses the directionality parameter to specify the position in the protein 200 that experiences the target variant at the amino acid level.

As discussed above, all the distance values in the twenty-one amino acid-wise distance channels 602-642 are measured from respective nearest atoms to the voxels 514 in the voxel grid 512. These nearest atoms originate from one of the reference amino acids in the reference amino acid sequence 202. These originating reference amino acids, which contain the nearest atoms, can be classified into two categories: (1) those originating reference amino acids that precede the variant-experiencing reference amino acid 204 in the reference amino acid sequence 202 and (2) those originating reference amino acids that succeed the variant-experiencing reference amino acid 204 in the reference amino acid sequence 202. The originating reference amino acids in the first category can be called preceding reference amino acids. The originating reference amino acids in the second category can be called succeeding reference amino acids.

The directionality parameter is applied to those distance values in the twenty-one amino acid-wise distance channels 602-642 that are measured from those nearest atoms that originate from the preceding reference amino acids. In one implementation, the directionality parameter is multiplied with such distance values. The directionality parameter can be any number, such as −1.

As a result of the application of the directionality parameter, the twenty-one amino acid-wise distance channels 600 include some distance values that indicate to the pathogenicity classifier which end of the protein 200 is the start terminal and which end is the end terminal. This also allows the pathogenicity classifier to reconstruct a protein sequence from the 3D protein structure information supplied by the distance channels and the reference and allele channels.

Distance Channel Tensor

Figure 7:
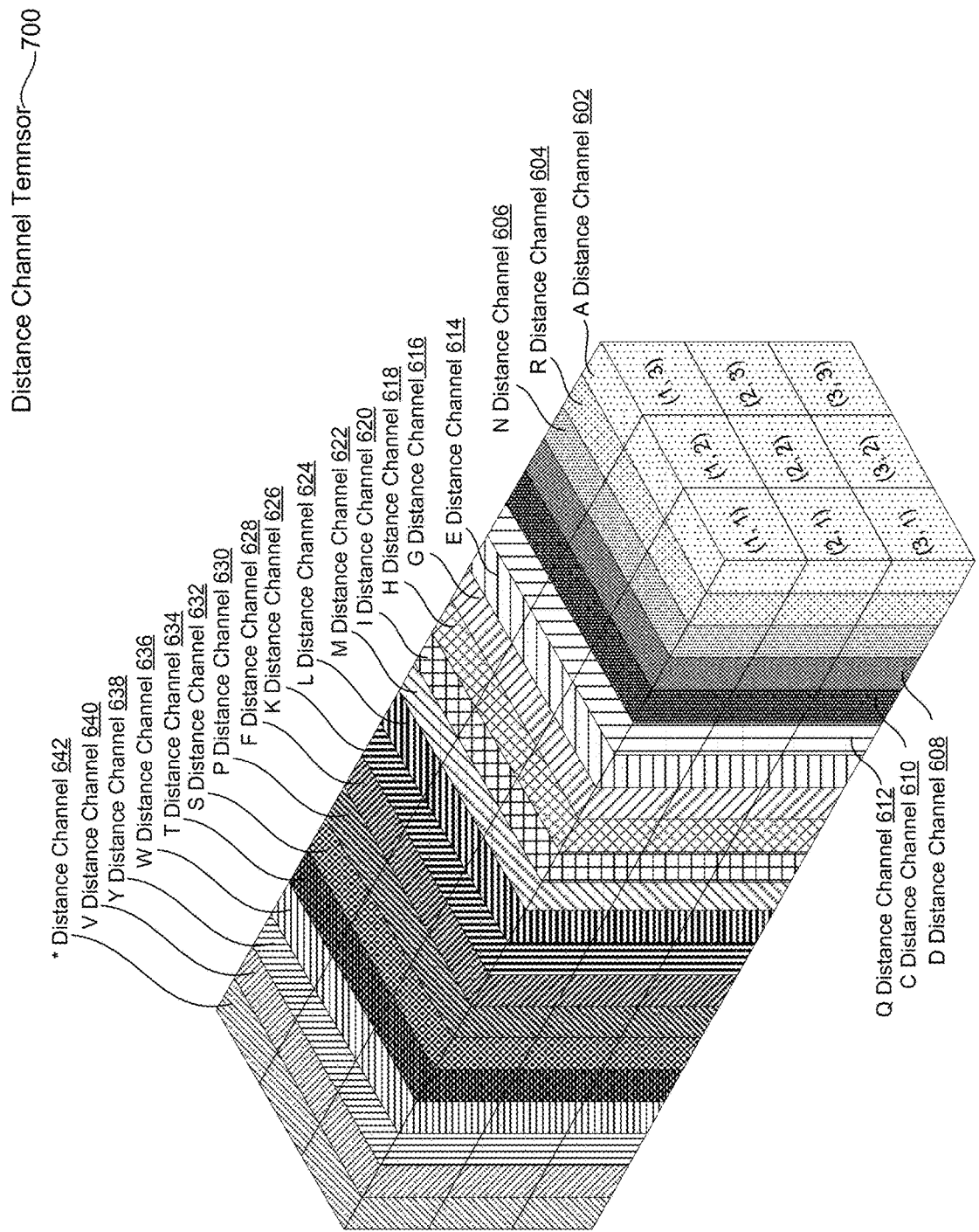
FIG. 7 is a schematic diagram of a distance channel tensor, in accordance with one implementation of the technology disclosed.

FIG. 7 is a schematic diagram of a distance channel tensor 700. Distance channel tensor 700 is a voxelized representation of the amino acid-wise distance channels 600 from FIG. 6. In the distance channel tensor 700, the twenty-one amino acid-wise distance channels 602-642 are concatenated voxel-wise, like RGB channels of a color image. The voxelized dimensionality of the distance channel tensor 700 is 21×3×3×3 (where 21 denotes the twenty-one amino acid categories and 3×3×3 denotes the 3D voxel grid with twenty-seven voxels); although FIG. 7 is a 2D depiction of dimensionality 21×3×3.

One-Hot Encodings

FIG. 8 shows one-hot encodings 800 of the reference amino acid 204 and the alternative amino acid 214. In FIG. 8, left column is a one-hot encoding 802 of the reference amino acid Glycine (G) 204, with one for the Glycine amino acid category and zeros for all other amino acid categories. In FIG. 8, right column is a one-hot encoding 804 of the variant/alternative amino acid Alanine (A) 214, with one for the Alanine amino acid category and zeros for all other amino acid categories.

FIG. 9 is a schematic diagram of a voxelized one-hot encoded reference amino acid 902 and a voxelized one-hot encoded variant/alternative amino acid 912. The voxelized one-hot encoded reference amino acid 902 is a voxelized representation of the one-hot encoding 802 of the reference amino acid Glycine (G) 204 from FIG. 8. The voxelized one-hot encoded alternative amino acid 912 is a voxelized representation of the one-hot encoding 804 of the variant/alternative amino acid Alanine (A) 214 from FIG. 8. The voxelized dimensionality of the voxelized one-hot encoded reference amino acid 902 is 21×1×1×1 (where 21 denotes the twenty-one amino acid categories); although FIG. 9 is a 2D depiction of dimensionality 21×1×1. Similarly, the voxelized dimensionality of the voxelized one-hot encoded alternative amino acid 912 is 21×1×1×1 (where 21 denotes the twenty-one amino acid categories); although FIG. 9 is a 2D depiction of dimensionality 21×1×1.

Reference Allele Tensor

Figure 10:
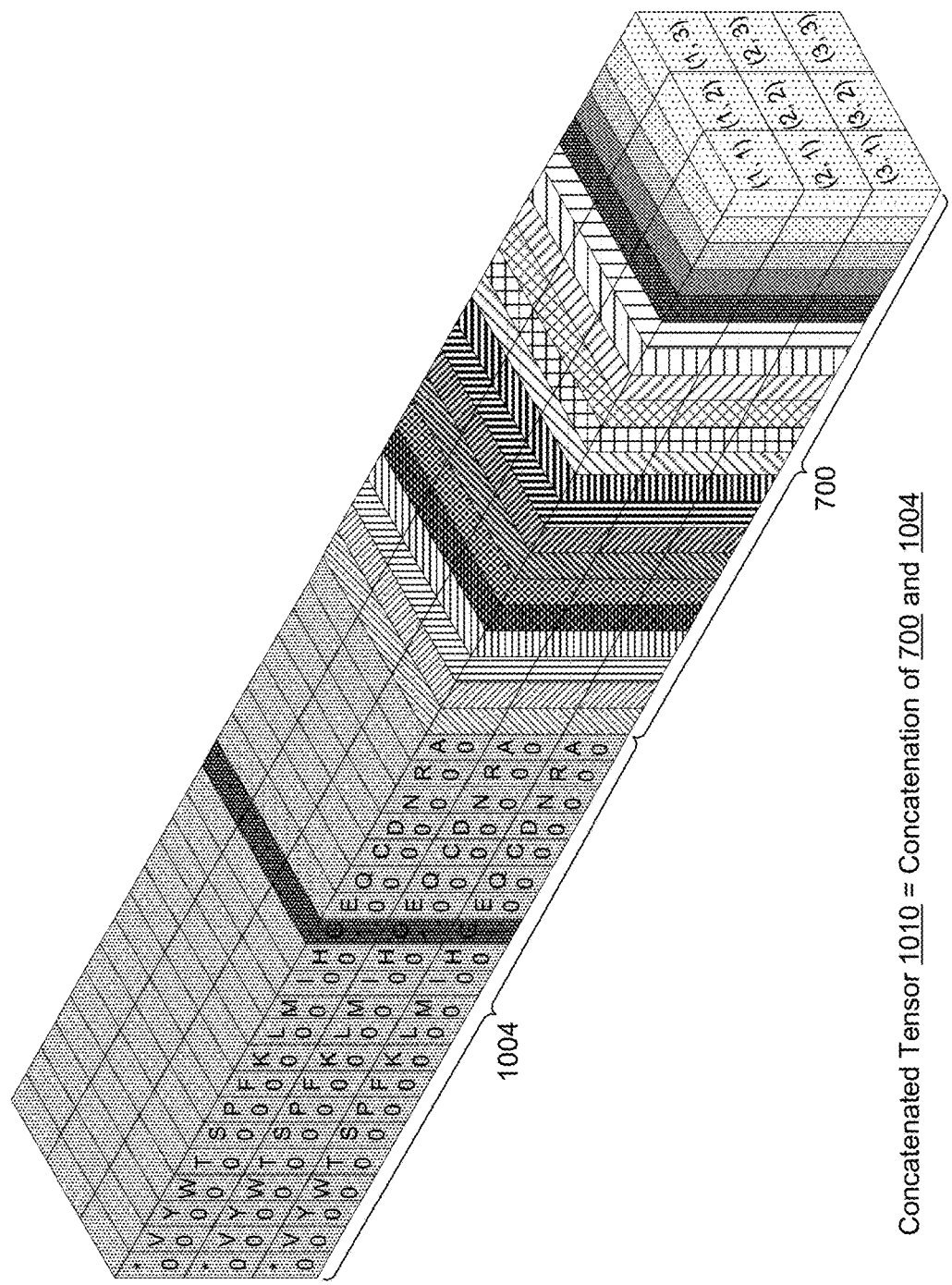
FIG. 10 schematically illustrates a concatenation process that voxel-wise concatenates the distance channel tensor of FIG. 7 and a reference allele tensor, in accordance with one implementation of the technology disclosed.

FIG. 10 schematically illustrates a concatenation process 1000 that voxel-wise concatenates the distance channel tensor 700 of FIG. 7 and a reference allele tensor 1004. The reference allele tensor 1004 is a voxel-wise aggregation (repetition/cloning/replication) of the voxelized one-hot encoded reference amino acid 902 from FIG. 9. That is, multiple copies of the voxelized one-hot encoded reference amino acid 902 are voxel-wise concatenated according with each other to the spatial arrangement of the voxels 514 in the voxel grid 512, such that the reference allele tensor 1004 has a corresponding copy of the voxelized one-hot encoded reference amino acid 910 for each of the voxels 514 in the voxel grid 512.

The concatenation process 1000 produces a concatenated tensor 1010. The voxelized dimensionality of the reference allele tensor 1004 is 21×3×3×3 (where 21 denotes the twenty-one amino acid categories and 3×3×3 denotes the 3D voxel grid with twenty-seven voxels); although FIG. 10 is a 2D depiction of the reference allele tensor 1004 having dimensionality 21×3×3. The voxelized dimensionality of the concatenated tensor 1010 is 42×3×3×3; although FIG. 10 is a 2D depiction of the concatenated tensor 1010 having dimensionality 42×3×3.

Alternative Allele Tensor

Figure 11:
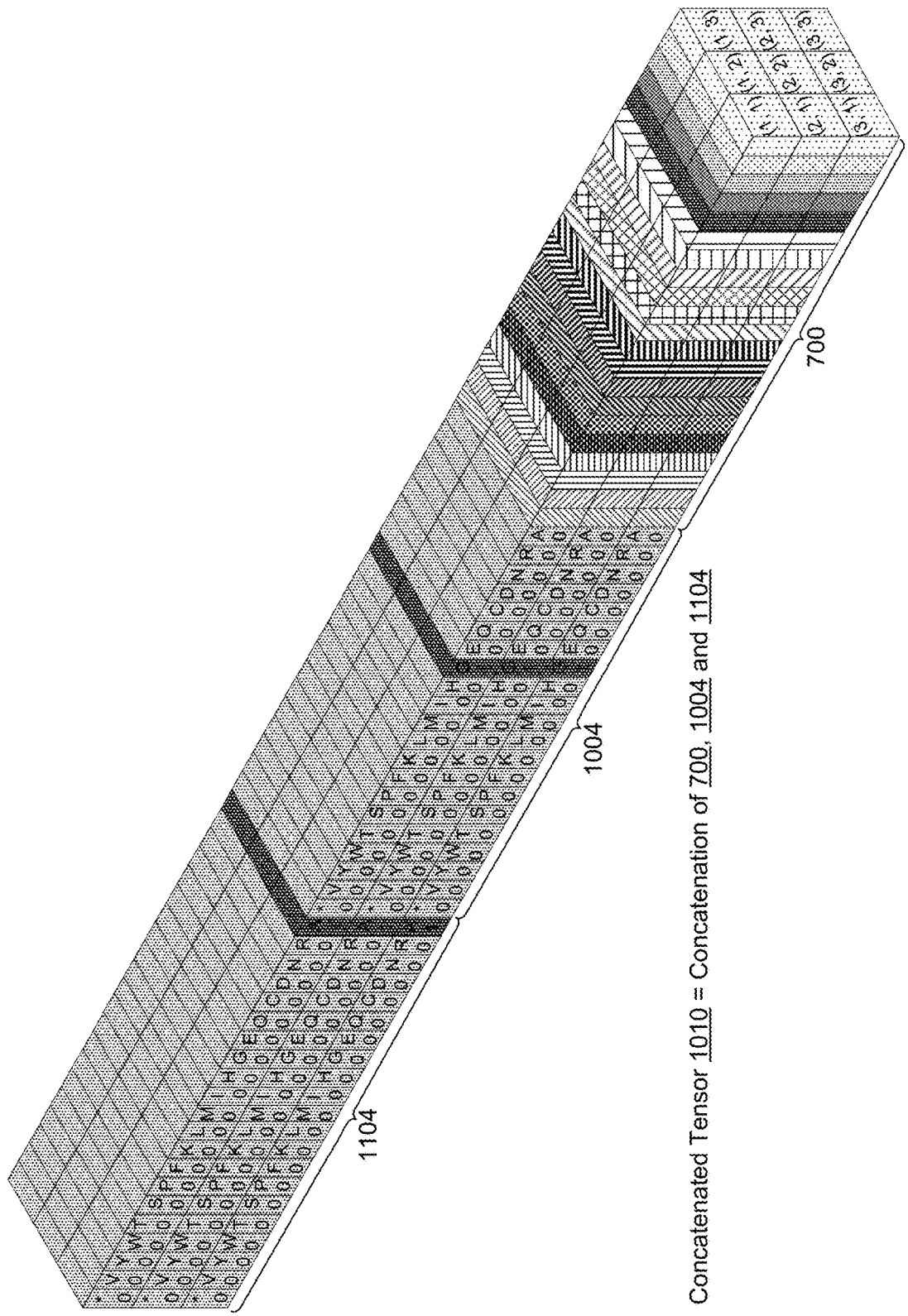
FIG. 11 schematically illustrates a concatenation process that voxel-wise concatenates the distance channel tensor of FIG. 7, the reference allele tensor of FIG. 10, and an alternative allele tensor, in accordance with one implementation of the technology disclosed.

FIG. 11 schematically illustrates a concatenation process 1100 that voxel-wise concatenates the distance channel tensor 700 of FIG. 7, the reference allele tensor 1004 of FIG. 10, and an alternative allele tensor 1104. The alternative allele tensor 1104 is a voxel-wise aggregation (repetition/cloning/replication) of the voxelized one-hot encoded alternative amino acid 912 from FIG. 9. That is, multiple copies of the voxelized one-hot encoded alternative amino acid 912 are voxel-wise concatenated with each other according to the spatial arrangement of the voxels 514 in the voxel grid 512, such that the alternative allele tensor 1104 has a corresponding copy of the voxelized one-hot encoded alternative amino acid 910 for each of the voxels 514 in the voxel grid 512.

The concatenation process 1100 produces a concatenated tensor 1110. The voxelized dimensionality of the alternative allele tensor 1104 is 21×3×3×3 (where 21 denotes the twenty-one amino acid categories and 3×3×3 denotes the 3D voxel grid with twenty-seven voxels); although FIG. 11 is a 2D depiction of the alternative allele tensor 1104 having dimensionality 21×3×3. The voxelized dimensionality of the concatenated tensor 1110 is 63×3×3×3; although FIG. 11 is a 2D depiction of the concatenated tensor 1110 having dimensionality 63×3×3.

In some implementations, the runtime logic 184 processes the concatenated tensor 1110 through the pathogenicity classifier to determine a pathogenicity of the variant/alternative amino acid Alanine (A) 214, which is in turn inferred as a pathogenicity determination of the underlying nucleotide variant that creates the variant/alternative amino acid Alanine (A) 214.

Evolutionary Conservation Channels

Predicting the functional consequences of variants relies at least in part on the assumption that crucial amino acids for protein families are conserved through evolution due to negative selection (i.e., amino acid changes at these sites were deleterious in the past), and that mutations at these sites have an increased likelihood of being pathogenic (causing disease) in humans. In general, homologous sequences of a target protein are collected and aligned, and a metric of conservation is computed based on the weighted frequencies of different amino acids observed in the target position in the alignment.

Accordingly, the technology disclosed concatenates the distance channel tensor 700, the reference allele tensor 1004, and the alternative allele tensor 1004 with evolutionary channels. One example of the evolutionary channels is pan-amino acid conservation frequencies. Another example of the evolutionary channels is per-amino acid conservation frequencies.

In some implementations, the evolutionary channels are constructed using position weight matrices (PWMs). In other implementations, the evolutionary channels are constructed using position specific frequency matrices (PSFMs). In yet other implementations, the evolutionary channels are constructed using computational tools like SIFT, PolyPhen, and PANTHER-PSEC. In yet other implementations, the evolutionary channels are preservation channels based on evolutionary preservation. Preservation is related to conservation, as it also reflects the effect of negative selection that has acted to prevent evolutionary change at a given site in a protein.

Pan-Amino Acid Evolutionary Profiles

Figure 12:
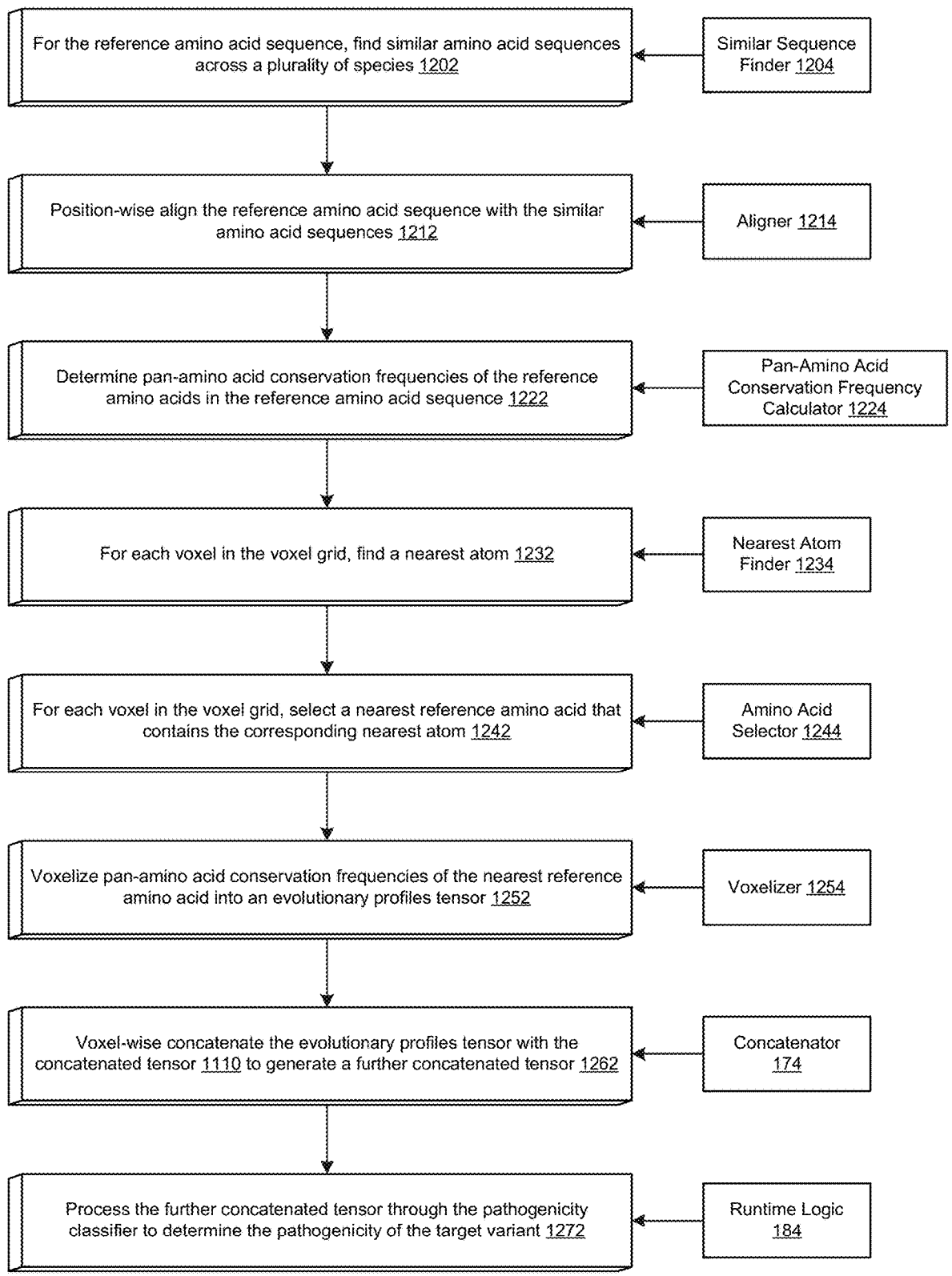
FIG. 12 is a flow diagram that illustrates a process of a system for determining and assigning pan-amino acid conservation frequencies of nearest atoms to voxels (voxelizing), in accordance with one implementation of the technology disclosed.

FIG. 12 is a flow diagram that illustrates a process 1200 of a system for determining and assigning pan-amino acid conservation frequencies of nearest atoms to voxels (voxelizing), in accordance with one implementation of the technology disclosed. FIGS. 12, 13, 14, 15, 16, 17, and 18 are discussed in tandem.

At step 1202, a similar sequence finder 1204 of the system retrieves amino acid sequences that are similar (homologous) to the reference amino acid sequence 202. The similar amino acid sequences can be selected from multiple species like primates, mammals, and vertebrates.

Figure 14:
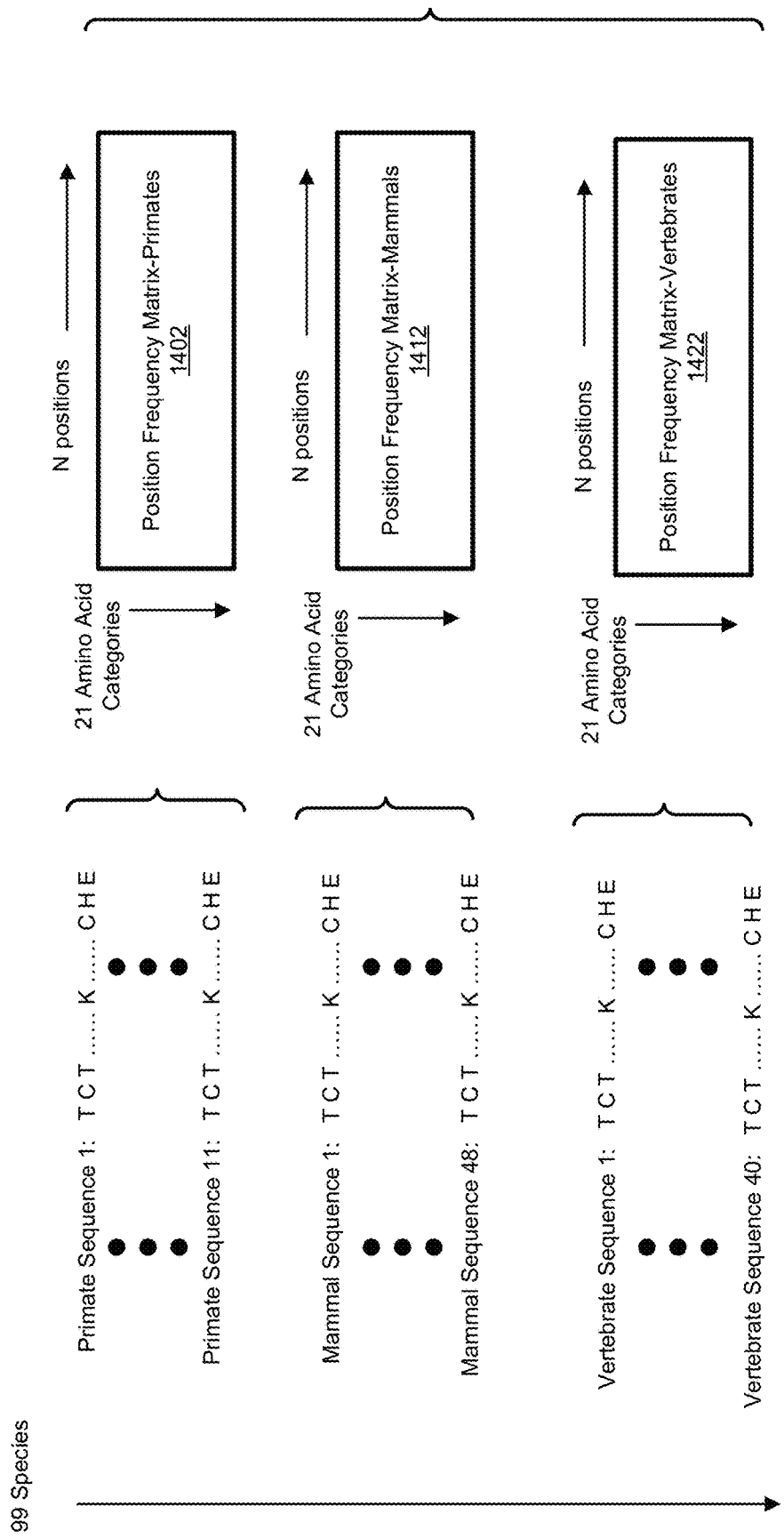
FIG. 14 shows an example multi-sequence alignment of the reference amino acid sequence across a ninety-nine species, in accordance with one implementation of the technology disclosed.

At step 1212, an aligner 1214 of the system position-wise aligns the reference amino acid sequence 202 with the similar amino acid sequences, i.e., the aligner 1214 performs a multi-sequence alignment. FIG. 14 shows an example multi-sequence alignment 1400 of the reference amino acid sequence 202 across a ninety-nine species. In some implementations, the multi-sequence alignment 1400 can be partitioned, for example, to generate a first position frequency matrix 1402 for primates, a second position frequency matrix 1412 for mammals, and a third position frequency matrix 1422 for primates. In other implementations, a single position frequency matrix is generated across the ninety-nine species.

At step 1222, a pan-amino acid conservation frequency calculator 1224 of the system uses the multi-sequence alignment to determine pan-amino acid conservation frequencies of the reference amino acids in the reference amino acid sequence 202.

At step 1232, a nearest atom finder 1234 of the system finds nearest atoms to the voxels 514 in the voxel grid 512. In some implementations, the search for the voxel-wise nearest atoms may not be confined to any particular amino acid category or atom type. That is, the voxel-wise nearest atoms can be selected across the amino acid categories and the amino acid types, as long as they are the most proximate atoms to the respective voxel centers. In other implementations, the search for the voxel-wise nearest atoms may be confined to only a particular atom category, such as only to a particular atomic element like oxygen, nitrogen, and hydrogen, or only to alpha-carbon atoms, or only to beta-carbon atoms, or only to sidechain atoms, or only to backbone atoms.

At step 1242, an amino acid selector 1244 of the system selects those reference amino acids in the reference amino acid sequence 202 that contain the nearest atoms identified at the step 1232. Such reference amino acids can be called nearest reference amino acids. FIG. 13 shows an example of locating nearest atoms 1302 to the voxels 514 in the voxel grid 512 and respectively mapping nearest reference amino acids 1312 that contain the nearest atoms 1302 to the voxels 514 in the voxel grid 512. This is identified in FIG. 13 as "voxels-to-nearest amino acids mapping 1300."

At step 1252, a voxelizer 1254 of the system voxelizes pan-amino acid conservation frequencies of the nearest reference amino acids. FIG. 15 shows an example of determining a pan-amino acid conservation frequencies sequence for the first voxel (1, 1) in the voxel grid 512, also referred to herein as "per-voxel evolutionary profile determination 1500."

Turning to FIG. 13, the nearest reference amino acid that was mapped to the first voxel (1, 1) is Aspartic acid (D) amino acid at position 15 in the reference amino acid sequence 202. Then, the multi-sequence alignment of the reference amino acid sequence 202 with, for example, ninety-nine homologous amino acid sequences of the ninety-nine species is analyzed at position 15. Such a position-specific and cross-species analysis reveals how many instances of amino acids from each of the twenty-one amino acid categories are found at position 15 across the hundred aligned amino acid sequences (i.e., the reference amino acid sequence 202 plus the ninety-nine homologous amino acid sequences).

In the example illustrated in FIG. 15, the Aspartic acid (D) amino acid is found at position 15 in ninety-six out of the hundred aligned amino acid sequences. So, the Aspartic acid amino acid category 1504 is assigned a pan-amino acid conservation frequency of 0.96. Similarly, in the illustrated example, the Valine (V) acid amino acid is found at position 15 in four out of the hundred aligned amino acid sequences. So, the Valine acid amino acid category 1514 is assigned a pan-amino acid conservation frequency of 0.04. Since no instances of amino acids from other amino acid categories are detected at position 15, the remaining amino acid categories are assigned a pan-amino acid conservation frequency of zero. This way, each of the twenty-one amino acid categories is assigned a respective pan-amino acid conservation frequency, which can be encoded in the pan-amino acid conservation frequencies sequence 1502 for the first voxel (1, 1).

FIG. 16 shows respective pan-amino acid conservation frequencies 1612-1692 determined for respective ones of the voxels 514 in the voxel grid 512 using the position frequency logic described in FIG. 15, also referred to herein as "voxels-to-evolutionary profiles mapping 1600."

Figure 17:
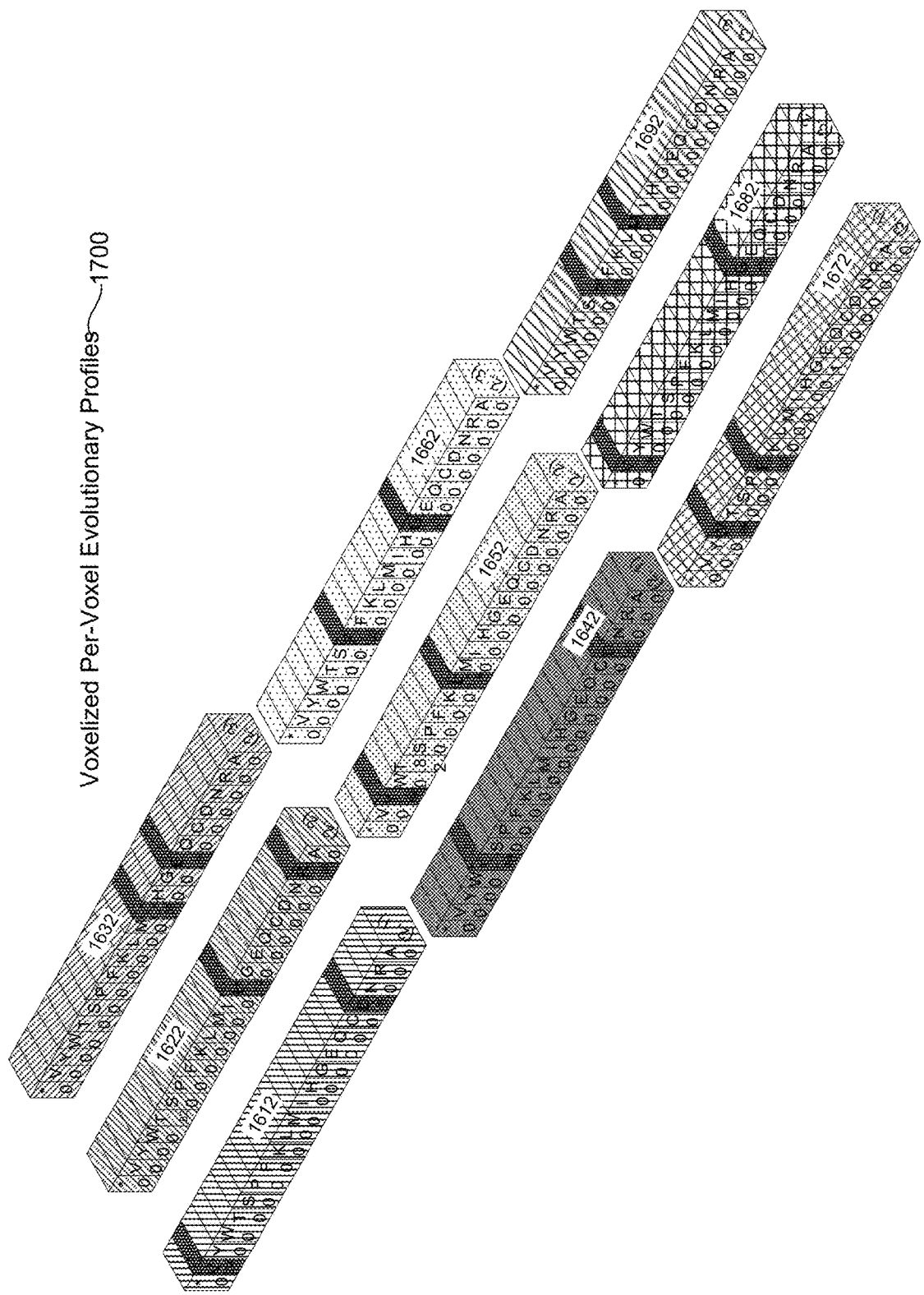
FIG. 17 illustrates voxelized per-voxel evolutionary profiles, in accordance with one implementation of the technology disclosed.

Per-voxel evolutionary profiles 1602 are then used by the voxelizer 1254 to generate voxelized per-voxel evolutionary profiles 1700, illustrated in FIG. 17. Often, each of the voxels 514 in the voxel grid 512 has a different pan-amino acid conservation frequencies sequence and therefore a different voxelized per-voxel evolutionary profile because the voxels are regularly mapped to different nearest atoms and therefore to different nearest reference amino acids. Of course, when two or more voxels have a same nearest atom and thereby a same nearest reference amino acid, a same pan-amino acid conservation frequencies sequence and a same voxelized per-voxel evolutionary profile is assigned to each of the two or more voxels.

Figure 18:
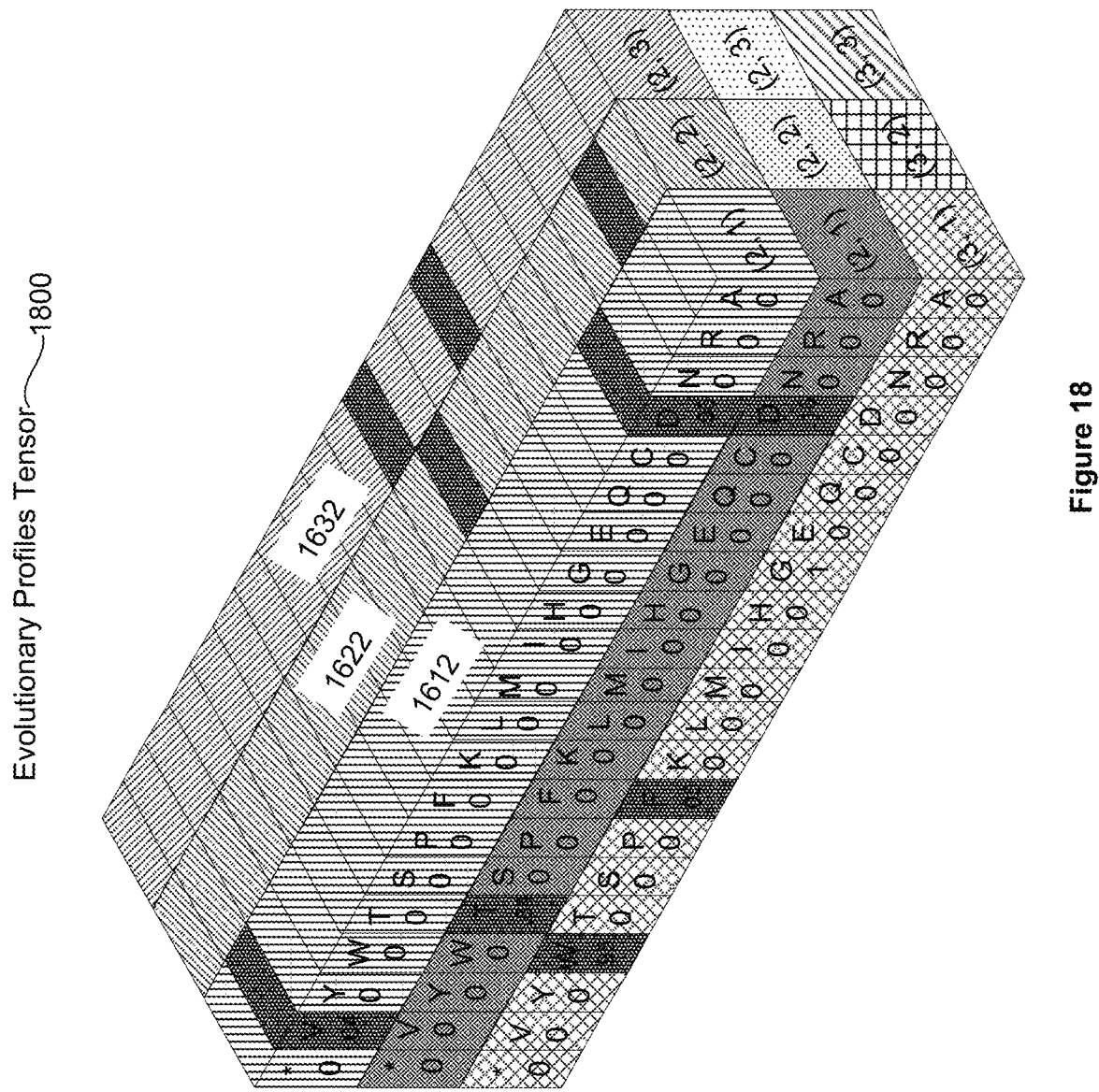
FIG. 18 depicts example of an evolutionary profiles tensor, in accordance with one implementation of the technology disclosed.

FIG. 18 depicts example of an evolutionary profiles tensor 1800 in which the voxelized per-voxel evolutionary profiles 1700 are voxel-wise concatenated with each other according to the spatial arrangement of the voxels 514 in the voxel grid 512. The voxelized dimensionality of the evolutionary profiles tensor 1800 is 21×3×3×3 (where 21 denotes the twenty-one amino acid categories and 3×3×3 denotes the 3D voxel grid with twenty-seven voxels); although FIG. 18 is a 2D depiction of the evolutionary profiles tensor 1800 having dimensionality 21×3×3.

At step 1262, the concatenator 174 voxel-wise concatenates the evolutionary profiles tensor 1800 with the distance channel tensor 700. In some implementations, the evolutionary profiles tensor 1800 is voxel-wise concatenated with the concatenator tensor 1110 to generate a further concatenated tensor of dimensionality 84×3×3×3 (not shown).

At step 1272, the runtime logic 184 processes the further concatenated tensor of dimensionality 84×3×3×3 through the pathogenicity classifier to determine the pathogenicity of the target variant, which is in turn inferred as a pathogenicity determination of the underlying nucleotide variant that creates the target variant at the amino acid level.

Per-Amino Acid Evolutionary Profiles

Figure 19:
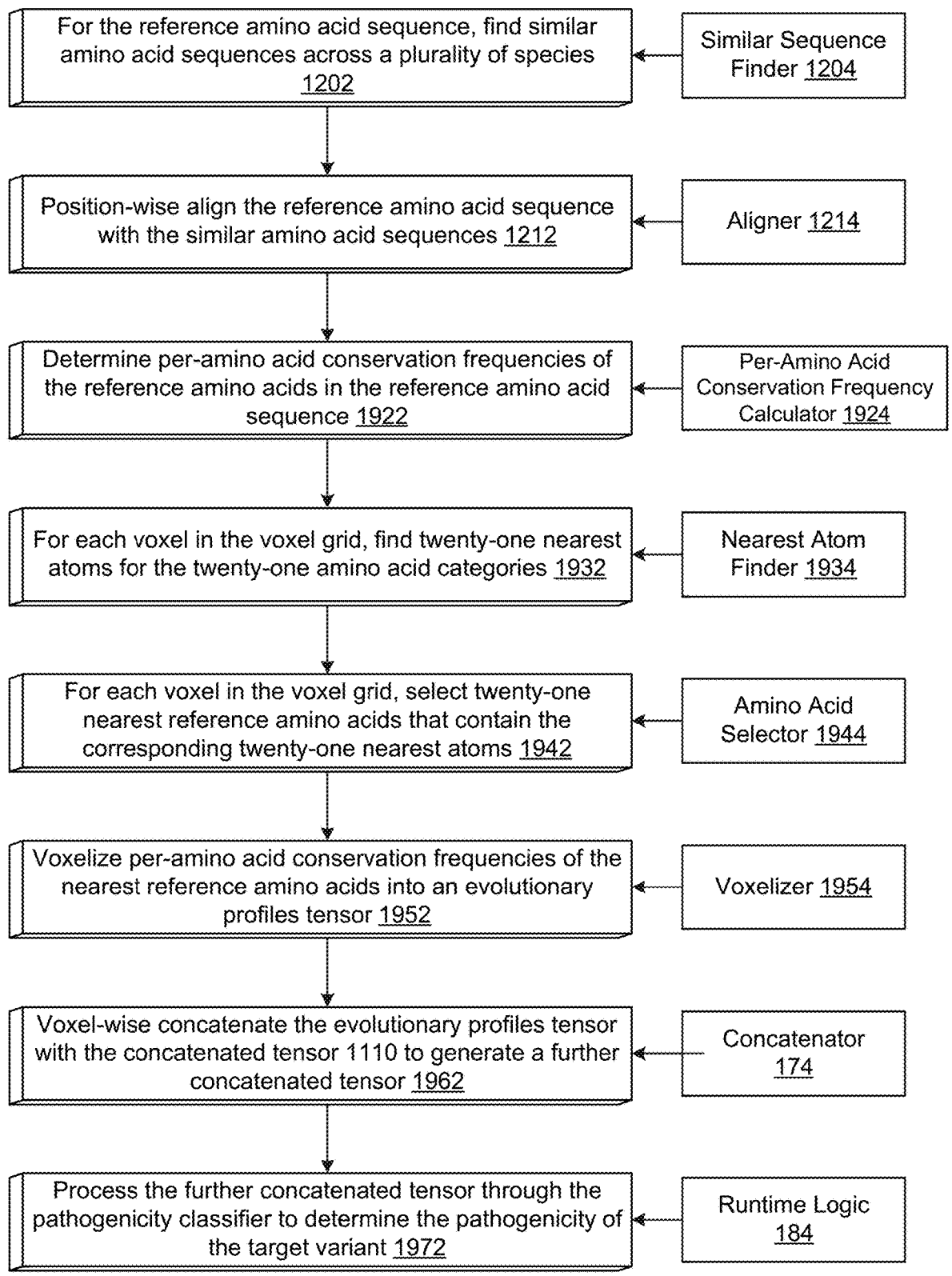
FIG. 19 is a flow diagram that illustrates a process of a system for determining and assigning per-amino acid conservation frequencies of nearest atoms to voxels (voxelizing), in accordance with one implementation of the technology disclosed.

FIG. 19 is a flow diagram that illustrates a process 1900 of a system for determining and assigning per-amino acid conservation frequencies of nearest atoms to voxels (voxelizing). In FIG. 19, the steps 1202 and 1212 are the same as FIG. 12.

At step 1922, a per-amino acid conservation frequency calculator 1924 of the system uses the multi-sequence alignment to determine per-amino acid conservation frequencies of the reference amino acids in the reference amino acid sequence 202.

At step 1932, a nearest atom finder 1934 of the system finds, for each of the voxels 514 in the voxel grid 512, twenty-one nearest atoms across each of the twenty-one amino acid categories. Each of the twenty-one nearest atoms is different from each other because they are selected from different amino acid categories. This leads to the selection of twenty-one unique nearest reference amino acids for a particular voxel, which in turn leads to generation of twenty-one unique position frequency matrices for the particular voxel, and which in turn leads to determination of twenty-one unique per-amino acid conservation frequencies for the particular voxel.

At step 1942, an amino acid selector 1944 of the system selects, for each of the voxels 514 in the voxel grid 512, twenty-one reference amino acids in the reference amino acid sequence 202 that contain the twenty-one nearest atoms identified at the step 1932. Such reference amino acids can be called nearest reference amino acids.

At step 1952, a voxelizer 1954 of the system voxelizes pen-amino acid conservation frequencies of the twenty-one nearest reference amino acids identified for the particular voxel at the step 1942. The twenty-one nearest reference amino acids are necessarily located at twenty-one different positions in the reference amino acid sequence 202 because they correspond to different underlying nearest atoms. Accordingly, for the particular voxel, twenty-one position frequency matrices can be generated for the twenty-one nearest reference amino acids. The twenty-one position frequency matrices can be generated across multiple species whose homologous amino acid sequences are position-wise aligned with the reference amino acid sequence 202, as discussed above with respect to FIGS. 12 to 15.

Then, using the twenty-one position frequency matrices, twenty-one position-specific conservation scores can be calculated for the twenty-one nearest reference amino acids identified for the particular voxel. These twenty-one position-specific conservation scores form the pen-amino acid conservation frequencies for the particular voxel, similar to the pan-amino acid conservation frequencies sequence 1502 in FIG. 12; except the sequence 1502 has many zero entries, whereas each element (feature) in a per-amino acid conservation frequencies sequence has a value (e.g., a floating point number) because the twenty-one nearest reference amino acids across the twenty-one amino acid categories necessarily have different positions that yield different position frequency matrices and thereby different per-amino acid conservation frequencies.

The above process is executed for each of the voxels 514 in the voxel grid 512, and the resulting voxel-wise per-amino acid conservation frequencies voxelized, tensorized, concatenated, and processed for pathogenicity determination similar to the pan-amino acid conservation frequencies discussed with respect to FIGS. 12 to 18.

Annotation Channels

Figure 20:
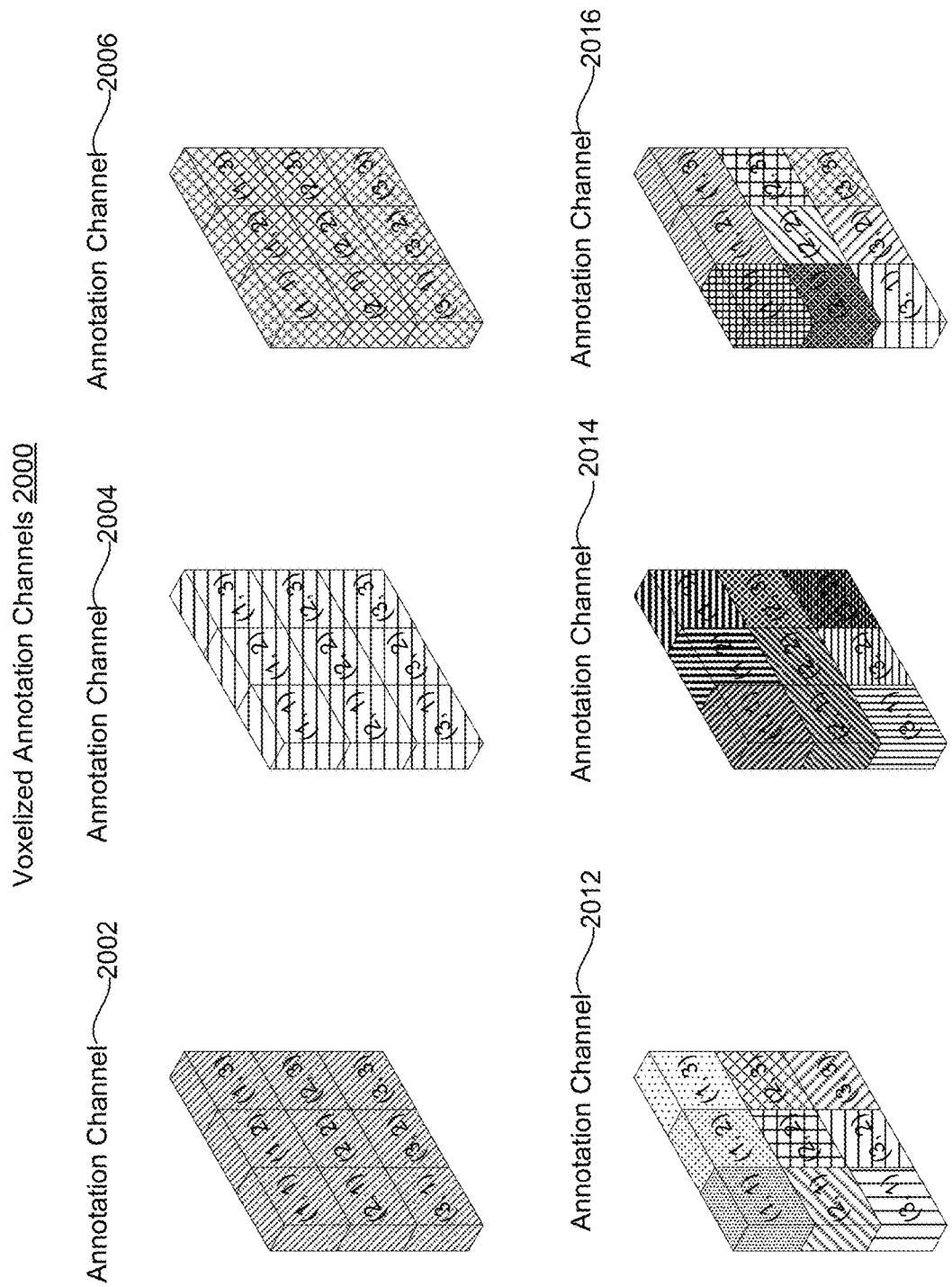
FIG. 20 shows various examples of voxelized annotation channels that are concatenated with the distance channel tensor, in accordance with one implementation of the technology disclosed.

FIG. 20 shows various examples of voxelized annotation channels 2000 that are concatenated with the distance channel tensor 700. In some implementations, the voxelized annotation channels are one-hot indicators for different protein annotations, for example whether an amino acid (residue) is part of a transmembrane region, a signal peptide, an active site, or any other binding site, or whether the residue is subject to posttranslational modifications, Path-Ratio (See Pei P, Zhang A: A Topological Measurement for Weighted Protein Interaction Network. *CSB* 2005, 268-278.), etc. Additional examples of the annotation channels can be found below in the Particular Implementations section and in the Claims.

The voxelized annotation channels are arranged voxel-wise such that the voxels can have a same annotation sequence like the voxelized reference allele and alternative allele sequences (e.g., annotation channels 2002, 2004, 2006), or the voxels can have respective annotation sequences like the voxelized per-voxel evolutionary profiles 1700 (e.g., annotation channels 2012, 2014, 2016 (as indicated by different shading)).

The annotation channels are voxelized, tensorized, concatenated, and processed for pathogenicity determination similar to the pan-amino acid conservation frequencies discussed with respect to FIGS. 12 to 18.

Structural Confidence Channels

The technology disclosed can also concatenate various voxelized structural confidence channels with the distance channel tensor 700. Some examples of the structure confidence channels include GMQE score (provided by Swiss-Model); B-factor; temperature factor column of homology models (indicates how well a residue satisfies (physical) constraints in the protein structure); normalized number of aligning template proteins for the residue nearest to the center of a voxel (alignments provided by HHpred, e.g., voxel is nearest to a residue at which 3 of 6 template structures align, signifying that the feature has value ⅜=0.5; minimum, maximum, and mean TM-scores; and predicted TM-scores of the template protein structures that align to the residue that is nearest to a voxel (continuing the example above, assume the 3 template structure has TM-scores 0.5, 0.5 and 1.5, then the minimum is 0.5, the mean is ⅔, and the maximum is 1.5). The TM-scores can be provided per protein template by HHpred. Additional examples of the structural confidence channels can be found below in the Particular Implementations section and in the Claims.

The voxelized structural confidence channels are arranged voxel-wise such that the voxels can have a same structural confidence sequence like the voxelized reference allele and alternative allele sequences, or the voxels can have respective structural confidence sequences like the voxelized per-voxel evolutionary profiles 1700.

The structural confidence channels are voxelized, tensorized, concatenated, and processed for pathogenicity determination similar to the pan-amino acid conservation frequencies discussed with respect to FIGS. 12 to 18.

Pathogenicity Classifier

Figure 21:
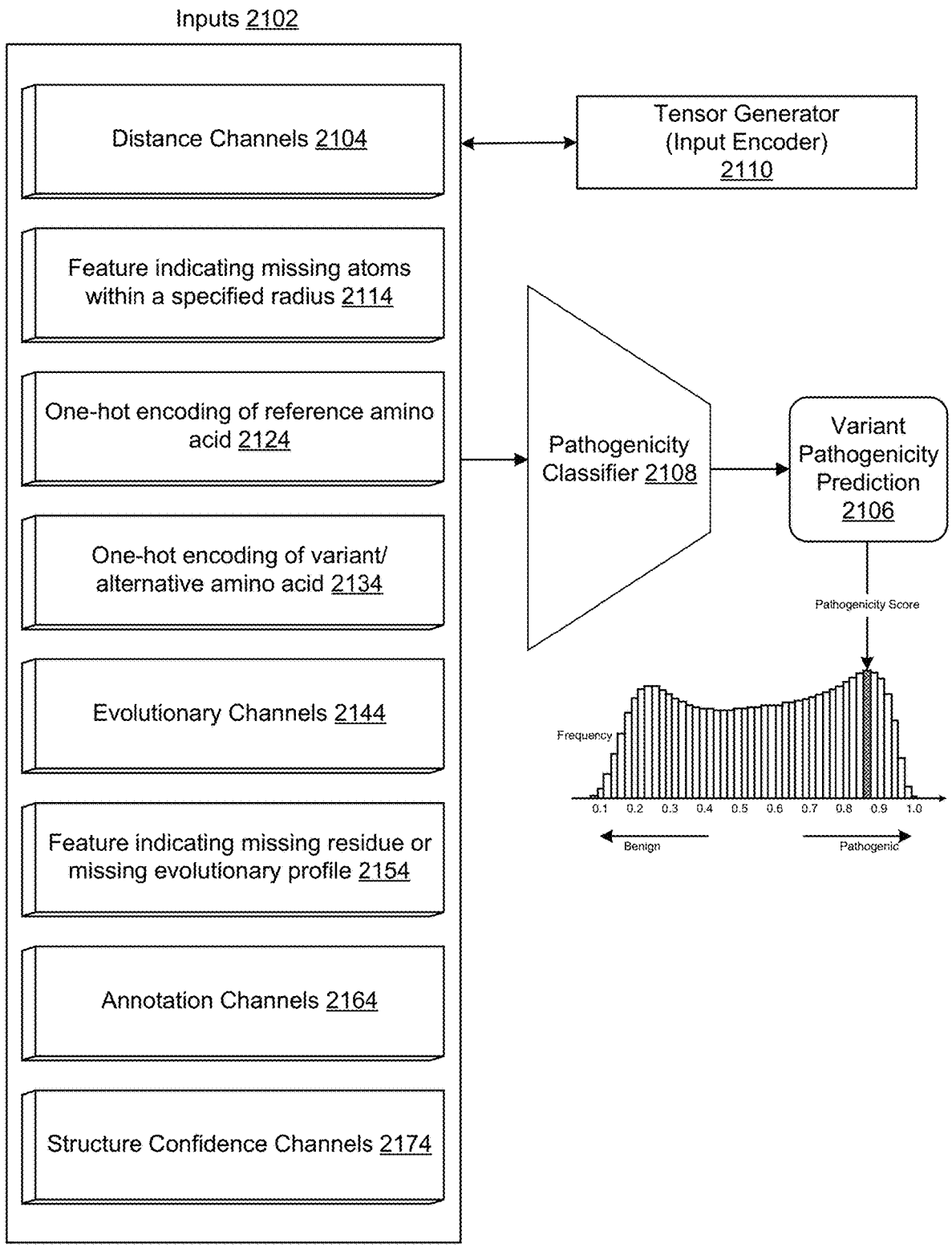
FIG. 21 illustrates different combinations and permutations of input channels that can be provided as inputs to a pathogenicity classifier for pathogenicity determination of a target variant, in accordance with one implementation of the technology disclosed.
Figure 22:
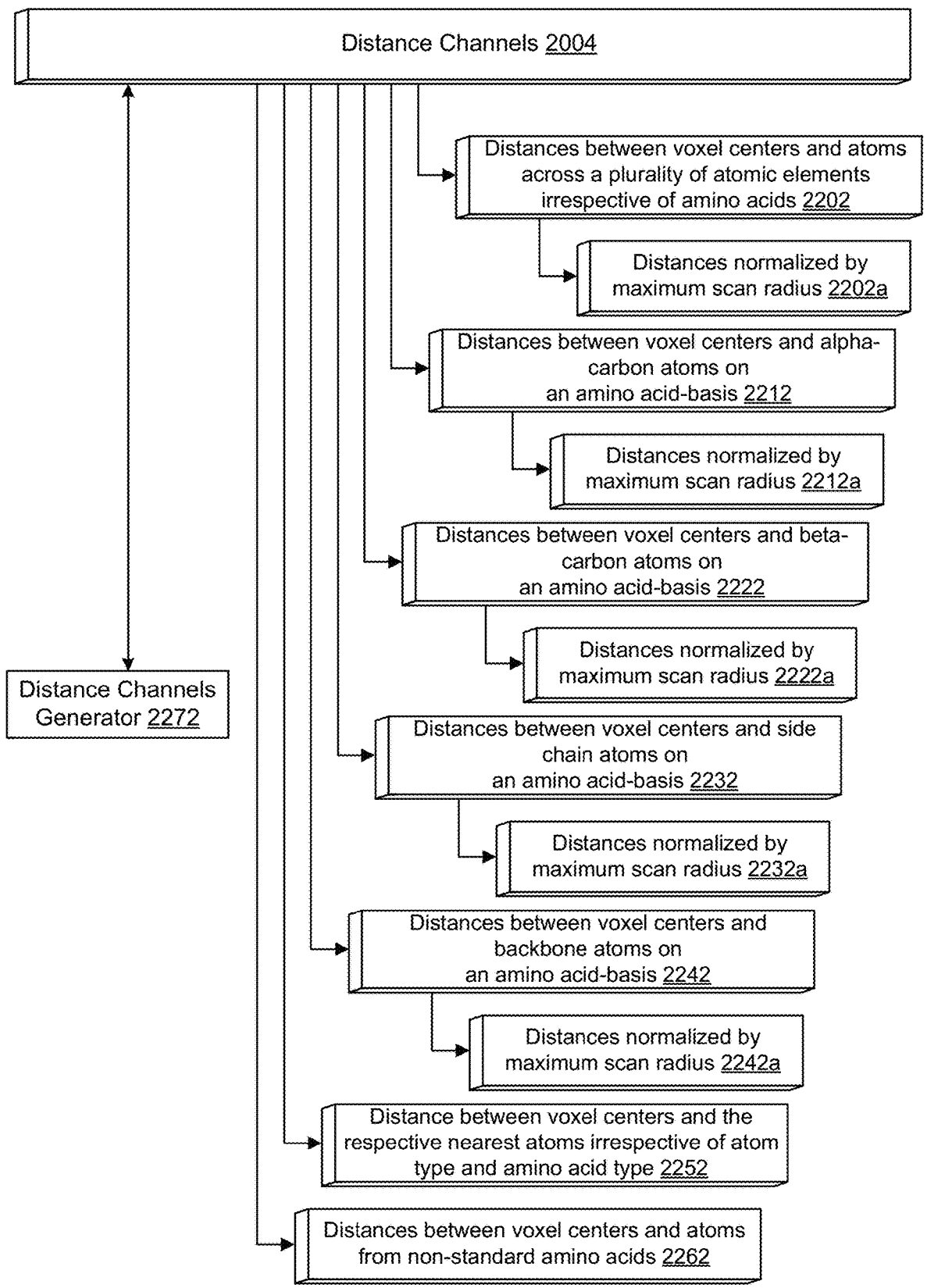
FIG. 22 shows different methods of calculating the disclosed distance channels, in accordance with various implementations of the technology disclosed.

FIG. 21 illustrates different combinations and permutations of input channels that can be provided as inputs 2102 to a pathogenicity classifier 2104 for a pathogenicity determination 2106 of a target variant. One of the inputs 2102 can be distance channels 2104 generated by a distance channels generator 2272. FIG. 22 shows different methods of calculating the distance channels 2104. In one implementation, the distance channels 2104 are generated based on distances 2202 between voxel centers and atoms across a plurality of atomic elements irrespective of amino acids. In some implementations, the distances 2202 are normalized by a maximum scan radius to generate normalized distances 2202*a*. In another implementation, the distance channels 2104 are generated based on distances 2212 between voxel centers and alpha-carbon atoms on an amino acid-basis. In some implementations, the distances 2212 are normalized by the maximum scan radius to generate normalized distances 2212*a*. In yet another implementation, the distance channels 2104 are generated based on distances 2222 between voxel centers and beta-carbon atoms on an amino acid-basis. In some implementations, the distances 2222 are normalized by the maximum scan radius to generate normalized distances 2222a. In yet another implementation, the distance channels 2104 are generated based on distances 2232 between voxel centers and side chain atoms on an amino acid-basis. In some implementations, the distances 2232 are normalized by the maximum scan radius to generate normalized distances 2232a. In yet another implementation, the distance channels 2104 are generated based on distances 2242 between voxel centers and backbone atoms on an amino acid-basis. In some implementations, the distances 2242 are normalized by the maximum scan radius to generate normalized distances 2242a. In yet another implementation, the distance channels 2104 are generated based on distances 2252 (one feature) between voxel centers and the respective nearest atoms irrespective of atom type and amino acid type. In yet another implementation, the distance channels 2104 are generated based on distances 2262 (one feature) between voxel centers and atoms from non-standard amino acids. In some implementations, the distances between the voxels and the atoms are calculated based on polar coordinates of the voxels and the atoms. The polar coordinates are parameterized by angles between the voxels and the atoms. In one implementation, this angel information is used to generate an angle channel for the voxels (i.e., independent of the distance channels). In some implementations, angles between a nearest atom and neighboring atoms (e.g., backbone atoms) can be used as features that are encoded with the voxels.

Another one of the inputs 2102 can be a feature 2114 indicating missing atoms within a specified radius.

Another one of the inputs 2102 can be one-hot encoding 2124 of the reference amino acid. Another one of the inputs 2102 can be one-hot encoding 2134 of the variant/alternative amino acid.

Figure 23:
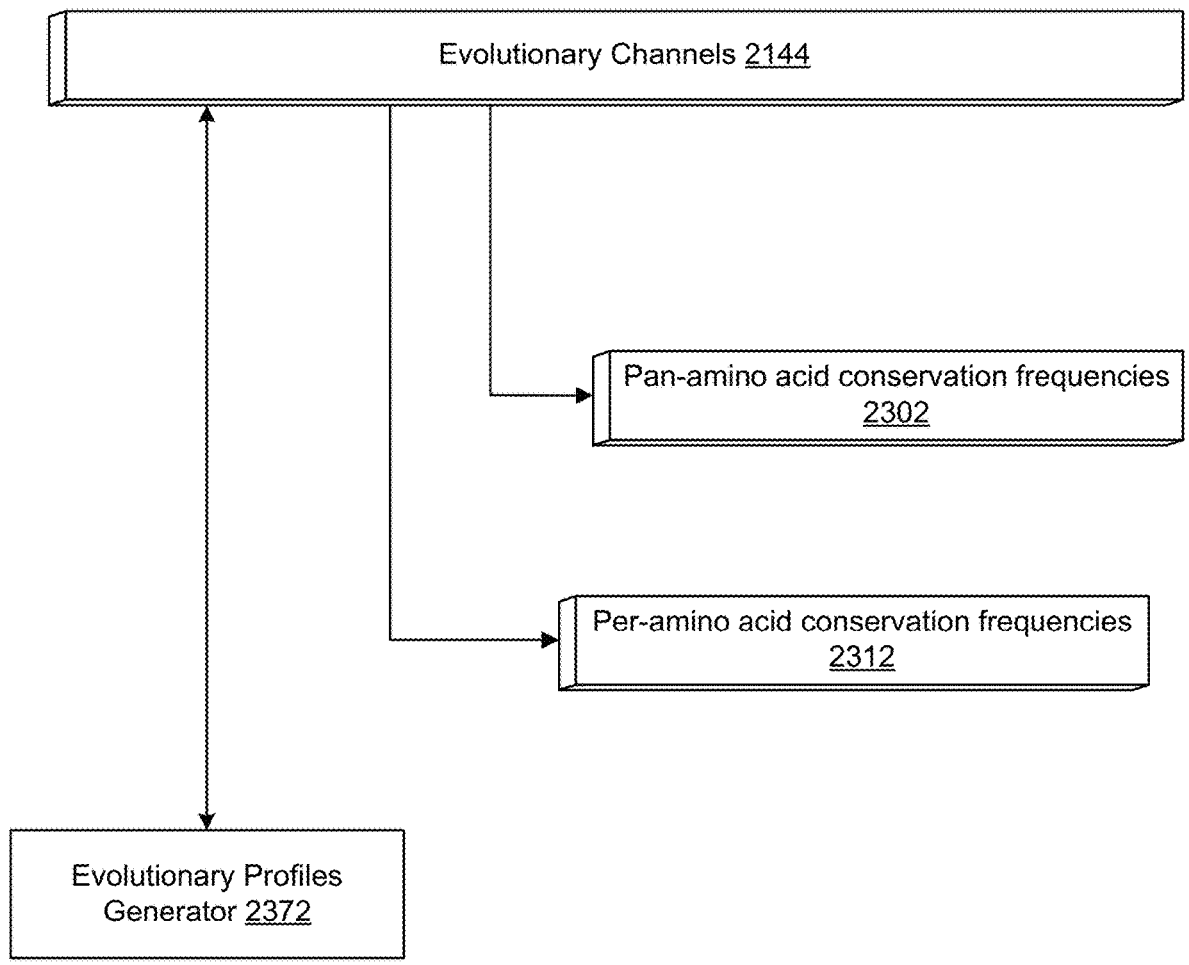
FIG. 23 shows different examples of the evolutionary channels, in accordance with various implementations of the technology disclosed.

Another one of the inputs 2102 can be evolutionary channels 2144 generated by an evolutionary profiles generator 2372, shown in FIG. 23. In one implementation, the evolutionary channels 2144 can be generated based on pan-amino acid conservation frequencies 2302. In another implementation, the evolutionary channels 2144 can be generated based on pan-amino acid conservation frequencies 2312.

Another one of the inputs 2102 can be a feature 2154 indicating missing residue or missing evolutionary profile.

Figure 24:
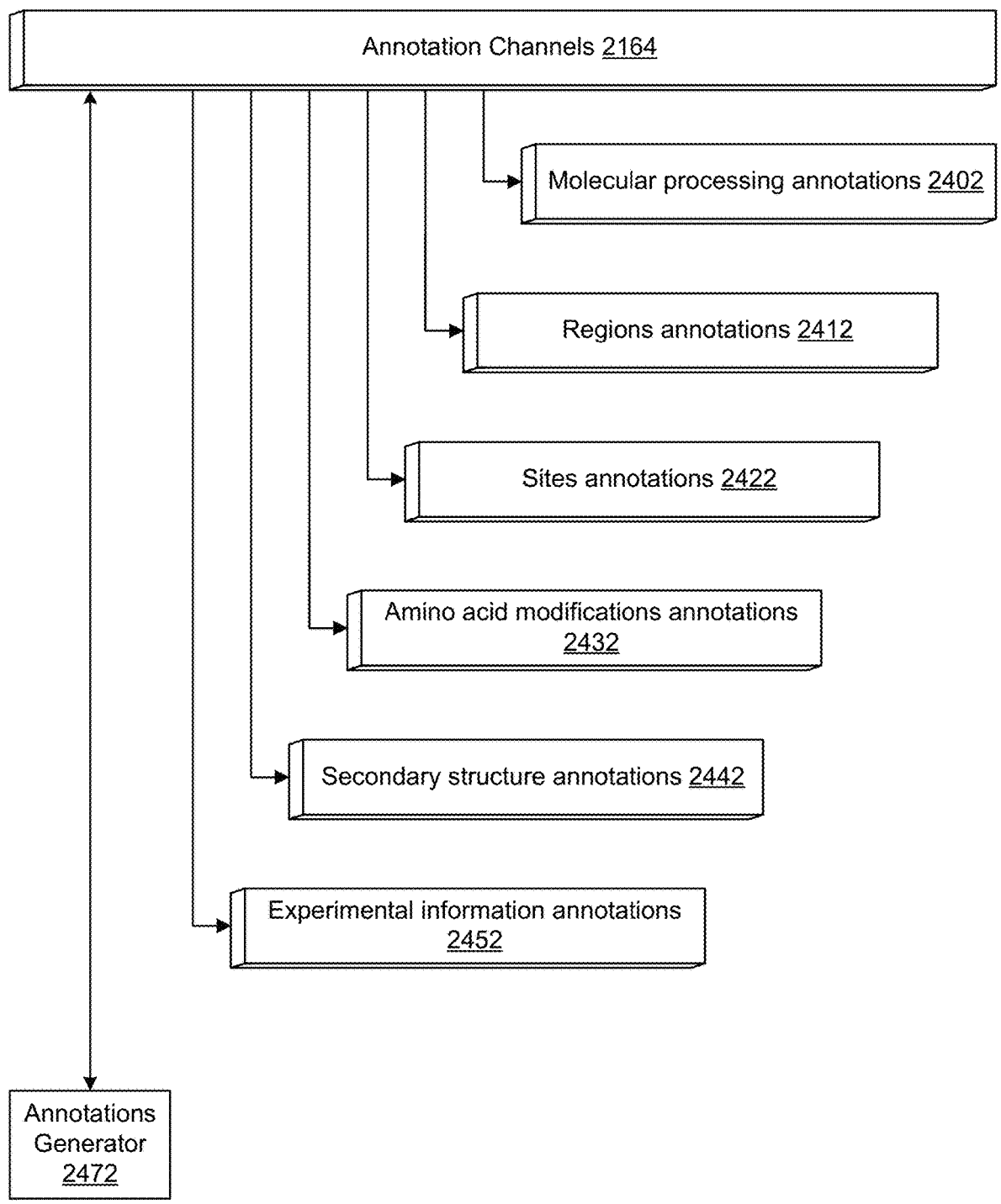
FIG. 24 shows different examples of the annotations channels, in accordance with various implementations of the technology disclosed.

Another one of the inputs 2102 can be annotations channels 2164 generated by an annotations generator 2472, shown in FIG. 24. In one implementation, the annotations channels 2154 can be generated based on molecular processing annotations 2402. In another implementation, the annotations channels 2154 can be generated based on regions annotations 2412. In yet another implementation, the annotations channels 2154 can be generated based on sites annotations 2422. In yet another implementation, the annotations channels 2154 can be generated based on Amino acid modifications annotations 2432. In yet another implementation, the annotations channels 2154 can be generated based on secondary structure annotations 2442. In yet another implementation, the annotations channels 2154 can be generated based on experimental information annotations 2452.

Figure 25:
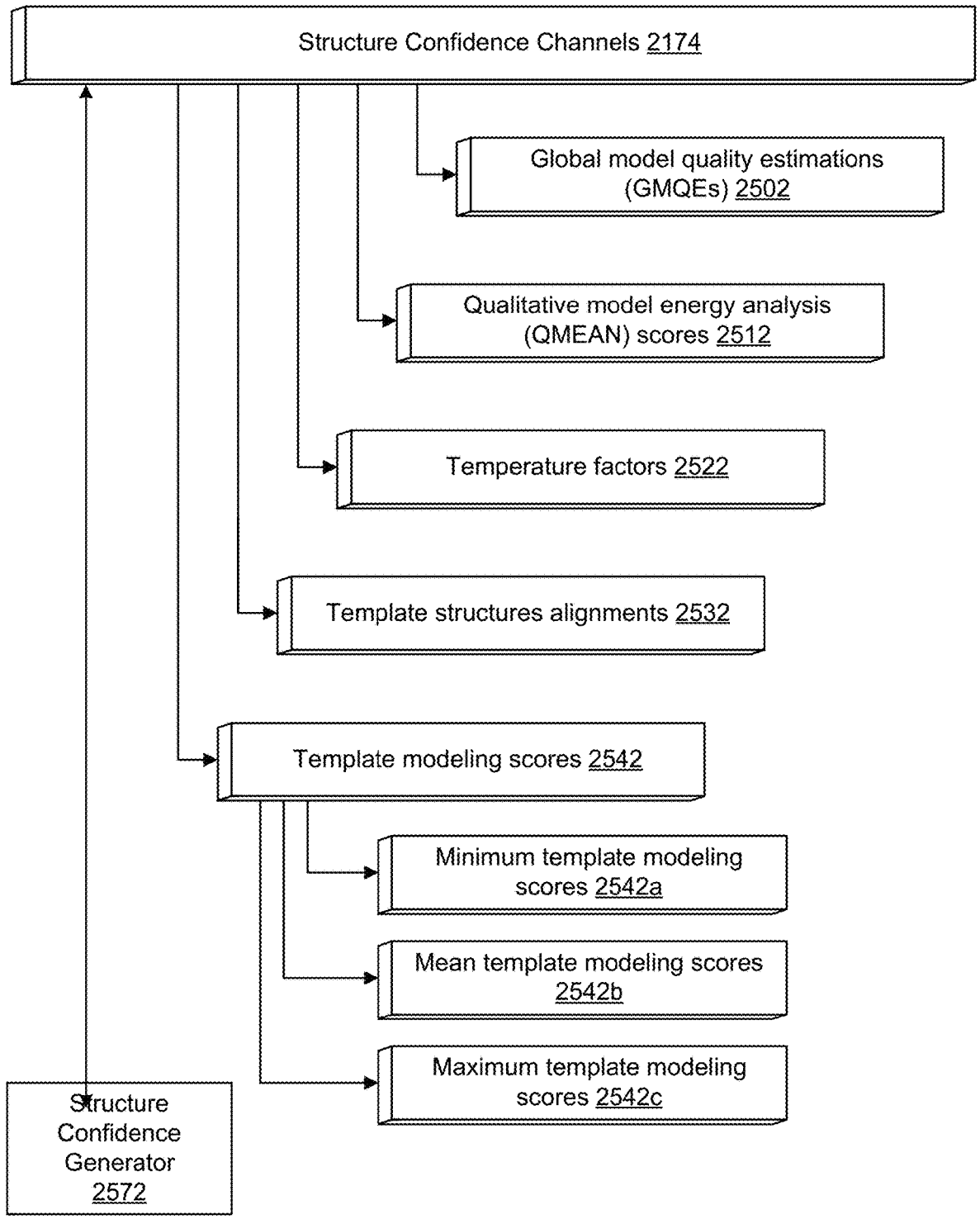
FIG. 25 shows different examples of the structure confidence channels, in accordance with various implementations of the technology disclosed.

Another one of the inputs 2102 can be structure confidence channels 2174 generated by a structure confidence generator 2572, shown in FIG. 25. In one implementation, the structure confidence 2174 can be generated based on global model quality estimations (GMQEs) 2502. In another implementation, the structure confidence 2174 can be generated based on qualitative model energy analysis (QMEAN) scores 2512. In yet another implementation, the structure confidence 2174 can be generated based on temperature factors 2522. In yet another implementation, the structure confidence 2174 can be generated based on template modeling scores 2542. Examples of the template modeling scores 2542 include minimum template modeling scores 2542a, mean template modeling scores 2542b, and maximum template modeling scores 2542c.

A person skilled in the art will appreciate that any permutation and combination of the input channels can be concatenated into an input for processing through the pathogenicity classifier 2104 for the pathogenicity determination 2106 of the target variant. In some implementations, only a subset of the input channels may be concatenated. The input channels can be concatenated in any order. In one implementation, the input channels can be concatenated into a single tensor by a tensor generator (input encoder) 2114. This single tensor can then be provided as input to the pathogenicity classifier 2104 for the pathogenicity determination 2106 of the target variant.

In one implementation, the pathogenicity classifier 2104 uses convolutional neural networks (CNNs) with a plurality of convolution layers. In another implementation, the pathogenicity classifier 2104 uses recurrent neural networks (RNNs) such as a long short-term memory networks (LSTMs), bi-directional LSTMs (Bi-LSTMs), and gated recurrent units (GRU)s. In yet another implementation, the pathogenicity classifier 2104 uses both the CNNs and the RNNs. In yet another implementation, the pathogenicity classifier 2104 uses graph-convolutional neural networks that model dependencies in graph-structured data. In yet another implementation, the pathogenicity classifier 2104 uses variational autoencoders (VAEs). In yet another implementation, the pathogenicity classifier 2104 uses generative adversarial networks (GANs). In yet another implementation, the pathogenicity classifier 2104 can also be a language model based, for example, on self-attention such as the one implemented by Transformers and BERTs.

In yet other implementations, the pathogenicity classifier 2104 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, attention mechanisms, and gaussian error linear unit.

The pathogenicity classifier 2104 is trained using back-propagation-based gradient update techniques. Example gradient descent techniques that can be used for training the pathogenicity classifier 2104 include stochastic gradient descent, batch gradient descent, and mini-batch gradient descent. Some examples of gradient descent optimization algorithms that can be used to train the pathogenicity classifier 2104 are Momentum, Nesterov accelerated gradient, Adagrad, Adadelta, RMSprop, Adam, AdaMax, Nadam, and AMSGrad. In other implementations, the pathogenicity classifier 2104 can be trained by unsupervised learning, semi-supervised learning, self-learning, reinforcement learning, multitask learning, multimodal learning, transfer learning, knowledge distillation, and so on.

Figure 26:
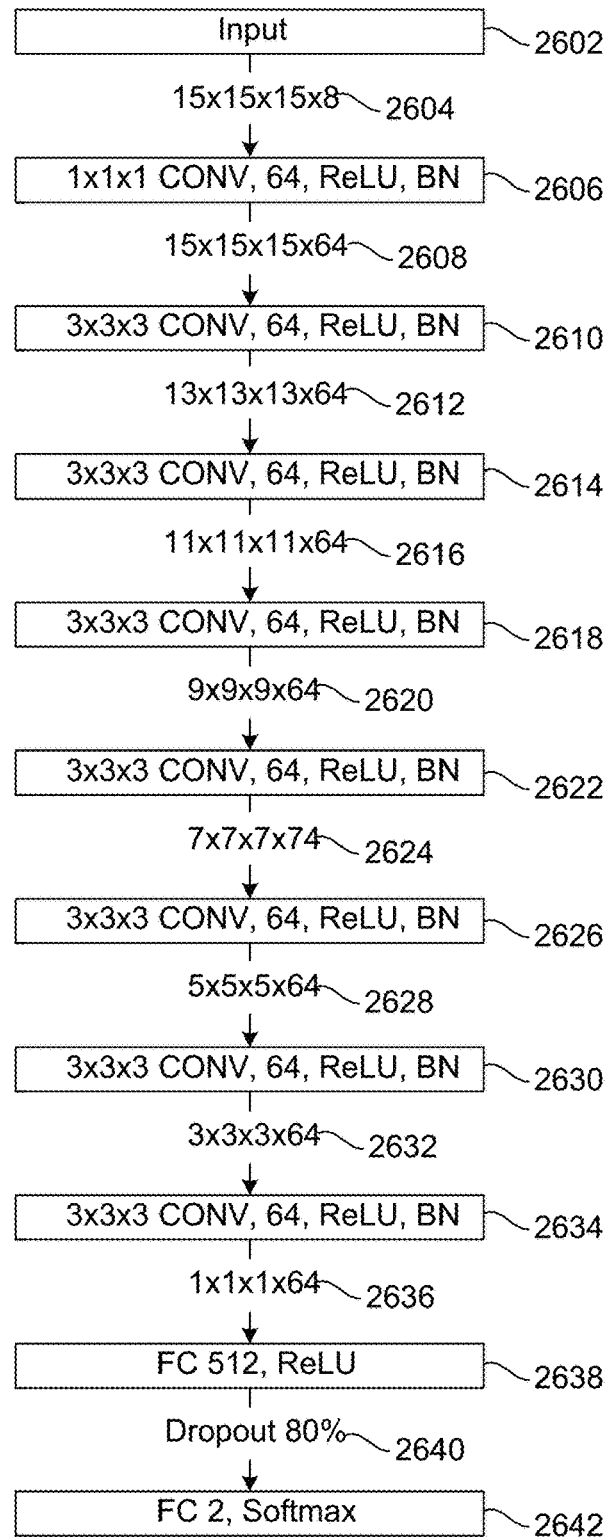
FIG. 26 shows an example processing architecture of the pathogenicity classifier, in accordance with one implementation of the technology disclosed.

FIG. 26 shows an example processing architecture 2600 of the pathogenicity classifier 2104, in accordance with one implementation of the technology disclosed. The processing architecture 2600 includes a cascade of processing modules 2606, 2610, 2614, 2618, 2622, 2626, 2630, 2634, 2638, and 2642 each of which can include 1D convolutions (1×1×1 CONV), 3D convolutions (3×3×3 CONV), ReLU non-linearity, and batch normalization (BN). Other examples of the processing modules include fully-connected (FC) layers, a dropout layer, a flattening layer, and a final softmax layer that produces exponentially normalized scores for the target variant belonging to a benign class and a pathogenic class. In FIG. 26, "64" denotes a number of convolution filters applied by a particular processing module. In FIG. 26, the size of an input voxel 2602 is 15×15×15×8. FIG. 26 also shows respective volumetric dimensionalities of the intermediate inputs 2604, 2608, 2612, 2616, 2620, 2624, 2628, 2632, 2636, and 2640 generated by the processing architecture 2600.

Figure 27:
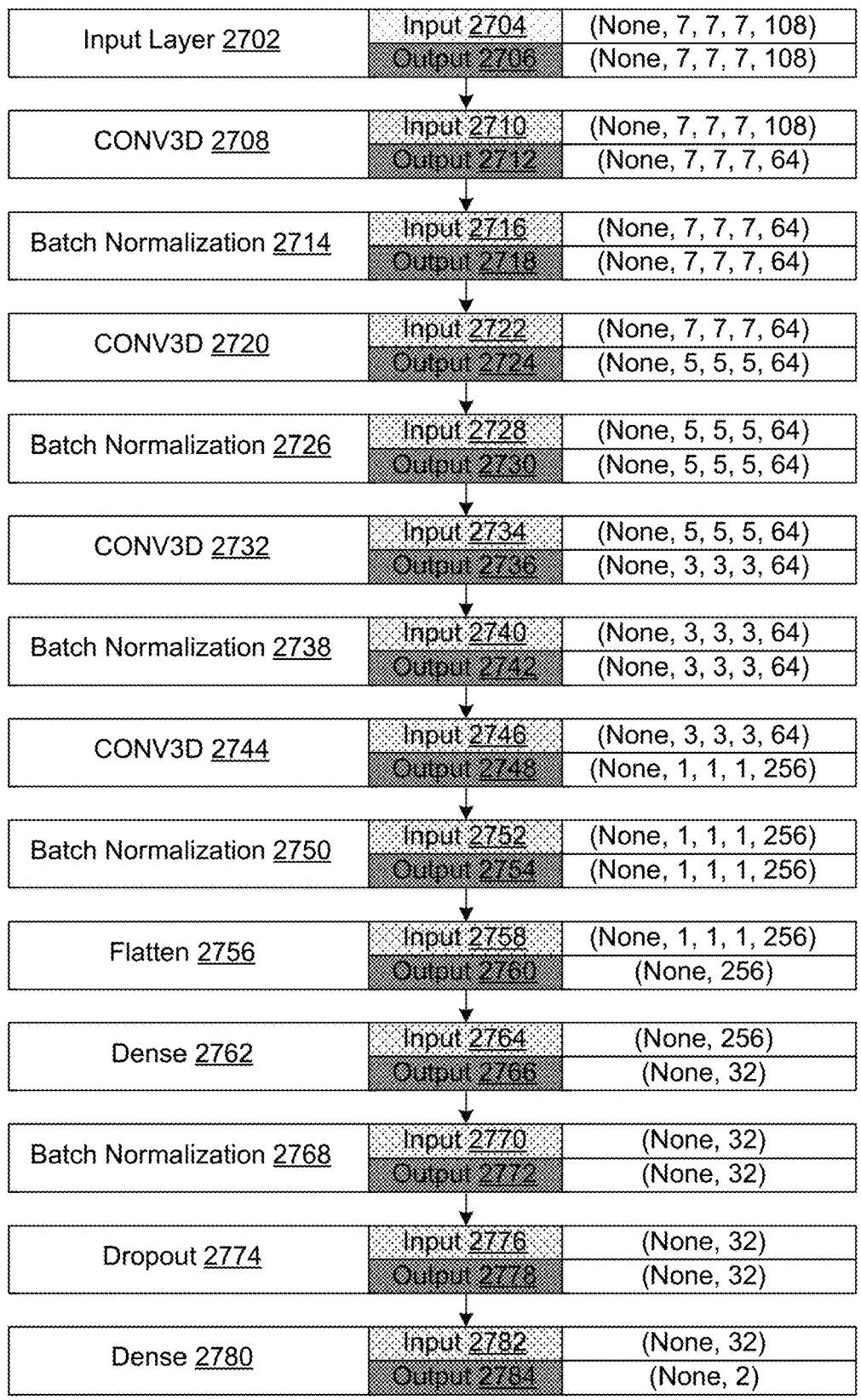
FIG. 27 shows an example processing architecture of the pathogenicity classifier, in accordance with one implementation of the technology disclosed.

FIG. 27 shows an example processing architecture 2700 of the pathogenicity classifier 2104, in accordance with one implementation of the technology disclosed. The processing architecture 2700 includes a cascade of processing modules 2708, 2714, 2720, 2726, 2732, 2738, 2744, 2750, 2756, 2762, 2768, 2774, and 2780 such as 1D convolutions (CONV 1D), 3D convolutions (CONV 3D), ReLU non-linearity, and batch normalization (BN). Other examples of the processing modules include fully-connected (dense) layers, a dropout layer, a flattening layer, and a final softmax layer that produces exponentially normalized scores for the target variant belonging to a benign class and a pathogenic class. In FIG. 27, "64" and "32" denote a number of convolution filters applied by a particular processing module. In FIG. 27, the size of an input voxel 2704 supplied by an input layer 2702 is 7×7×7×108. FIG. 27 also shows respective volumetric dimensionalities of the intermediate inputs 2710, 2716, 2722, 2728, 2734, 2740, 2746, 2752, 2758, 2764, 2770, 2776, and 2782 and the resulting intermediate outputs 2706, 2712, 2718, 2724, 2730, 2736, 2742, 2748, 2754, 2760, 2766, 2772, 2778, and 2784 generated by the processing architecture 2700.

A person skilled in the art will appreciate that other current and future artificial intelligence, machine learning, and deep learning models, datasets, and training techniques can be incorporated in the disclosed variant pathogenicity classifier without deviating from the spirit of the technology disclosed.

Performance Results as Objective Indicia of Inventiveness and Non-Obviousness

The variant pathogenicity classifier disclosed herein makes pathogenicity predictions based on 3D protein structures and is referred to as "PrimateAI 3D." "Primate AI" is a commonly owned and previously disclosed variant pathogenicity classifier that makes pathogenicity predictions based protein sequences. Additional details about PrimateAI can be found in commonly owned U.S. patent application Ser. Nos. 16/160,903; 16/160,986; 16/160,968; and 16/407, 149 and in Sundaram, L. et al. Predicting the clinical impact of human mutation with deep neural networks. Nat. Genet. 50, 1161-1170 (2018).

FIGS. 28, 29, 30, and 31 use PrimateAI as a benchmark model to demonstrate PrimateAI 3D's classification superiority over PrimateAI. The performance results in FIGS. 28, 29, 30, and 31 are generated on the classification task of accurately distinguishing benign variants from pathogenic variants across a plurality of validation sets. PrimateAI 3D is trained on training sets that are different from the plurality of validation sets. PrimateAI 3D is trained on common human variants and variants from primates used as benign dataset while simulated variants based on trinucleotide context used as unlabeled or pseudo-pathogenic dataset.

New developmental delay disorder (new DDD) is one example of a validation set used to compare the classification accuracy of Primate AI 3D against Primate AI. The new DDD validation set labels variants from individuals with DDD as pathogenic and labels the same variants from healthy relatives of the individuals with the DDD as benign. A similar labelling scheme is used with an autism spectrum disorder (ASD) validation set shown in FIG. 31.

BRCA1 is another example of a validation set used to compare the classification accuracy of Primate AI 3D against Primate AI. The BRCA1 validation set labels synthetically generated reference amino acid sequences simulating proteins of the BRCA1 gene as benign variants and labels synthetically altered allele amino acid sequences simulating proteins of the BRCA1 gene as pathogenic variants. A similar labelling scheme is used with different validation sets of the TP53 gene, TP53S3 gene and its variants, and other genes and their variants shown in FIG. 31.

Figure 28:
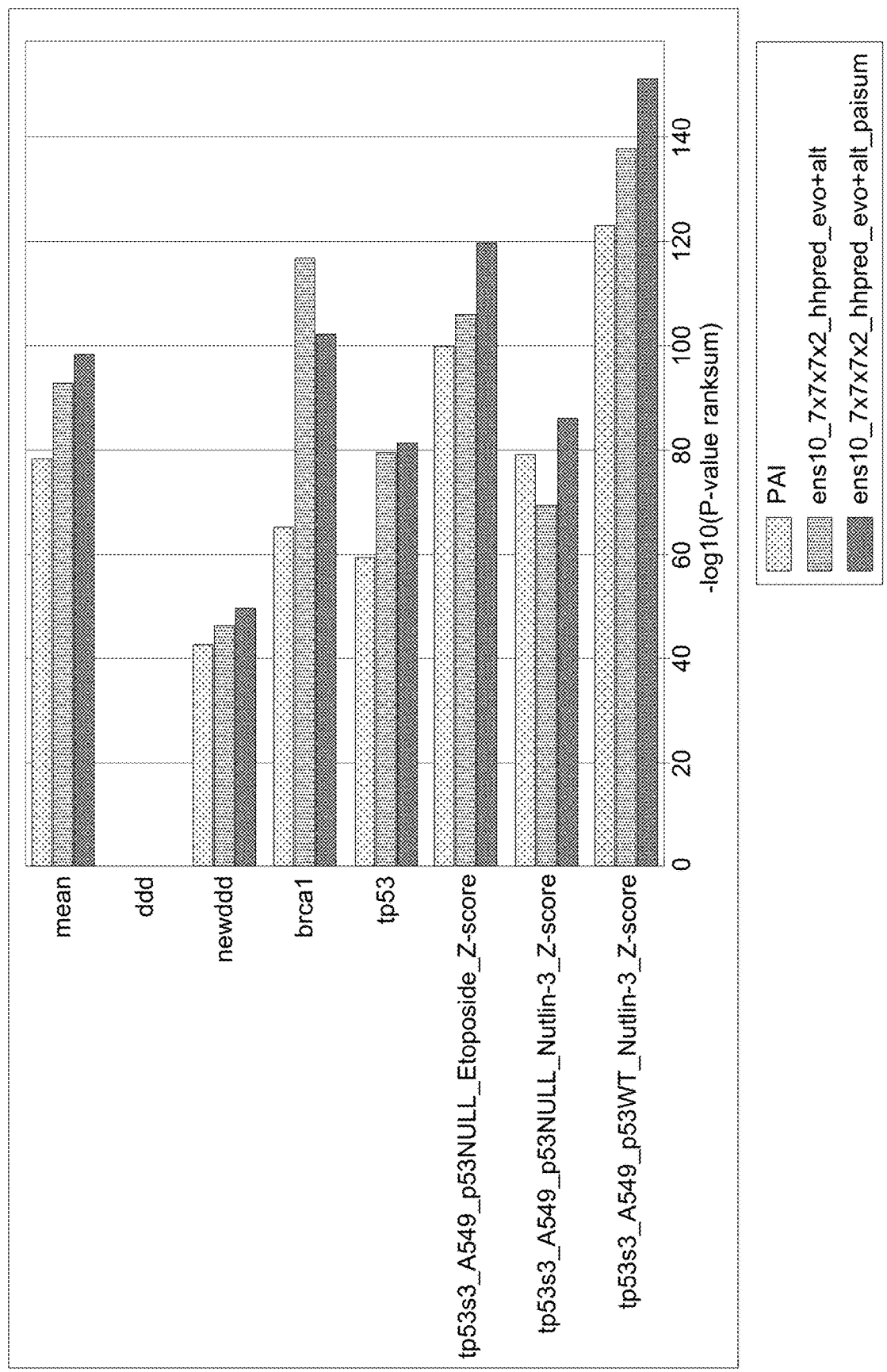
FIGS. 28, 29, 30, and 31 use PrimateAI as a benchmark model to demonstrate the disclosed PrimateAI 3D's classification superiority over PrimateAI.

FIG. 28 identifies performance of the benchmark PrimateAI model (PAI) and performance of the disclosed PrimateAI 3D model (ens10_7×7×7×2_hhpred_evo+alt). A third horizontal bar (ens10_7×7×7×2_hhpred_evo+alt_ paisum) depicts pathogenicity predictions derived by combining respective pathogenicity predictions of the disclosed PrimateAI 3D model and the benchmark PrimateAI model. In the legend, "ens10" denotes an ensemble of ten PrimateAI 3D models, each trained with a different seed training dataset and randomly initialized with different weights and biases. Also, "7×7×7×2" depicts the size of the voxel grid used to encode the input channels during the training of the ensemble of ten PrimateAI 3D models. For a given variant, the ensemble of ten PrimateAI 3D models respectively generates ten pathogenicity predictions, which are subsequently combined (e.g., by averaging) to generate a final pathogenicity prediction for the given variant. This logic analogous applies to ensembles of different group sizes.

Also, in FIG. 28, the y-axis has the different validation sets and the x-axis has p-values. Greater p-values, i.e., longer horizontal bars denote greater accuracy in differentiating benign variants from pathogenic variants. As demonstrated by the p-values in FIG. 28, PrimateAI 3D outperforms PrimateAI across most of the validation sets (only exception being the tp53s3_A549 validation set). That is, the horizontal bars for PrimateAI 3D are consistently longer than the horizontal bars for PrimateAI (PAI).

Also, in FIG. 28, a "mean" category along the y-axis calculates the mean of the p-values determined for each of the validation sets. In the mean category as well, PrimateAI 3D outperforms PrimateAI.

Figure 29:
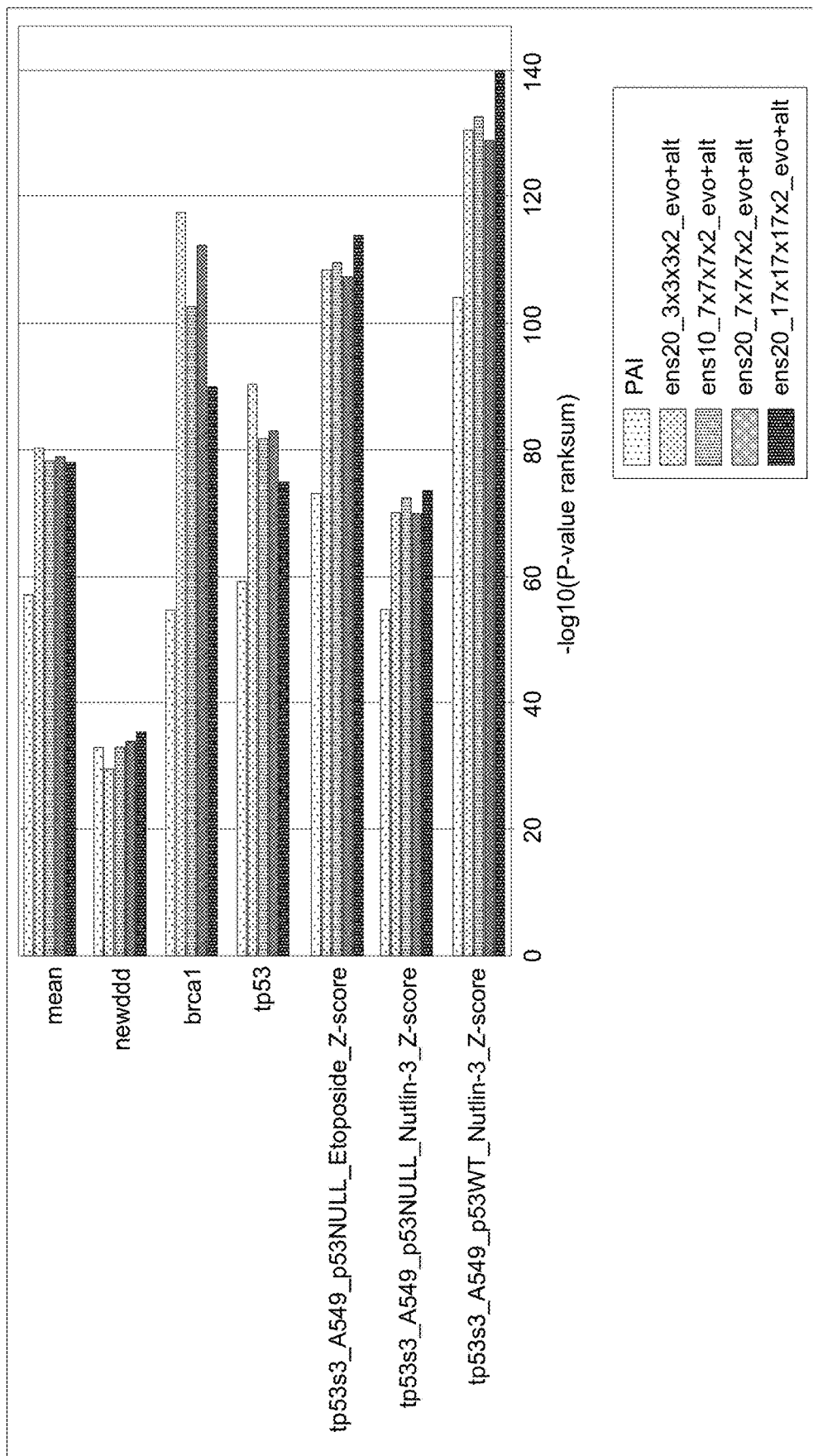

In FIG. 29, PrimateAI is represented by horizontal bars corresponding to "PAI," an ensemble of twenty PrimateAI 3D models trained with a voxel grid of size 3×3×3 is represented by horizontal bars corresponding to "ens20_3×3×3×2_evo+alt," an ensemble of ten PrimateAI 3D models trained with a voxel grid of size 7×7×7 is represented by horizontal bars corresponding to "ens10_7×7×7×2_evo+alt," an ensemble of twenty PrimateAI 3D models trained with a voxel grid of size 7×7×7 is represented by horizontal bars corresponding to "ens20_7×7×7×2_evo+alt," and an ensemble of twenty PrimateAI 3D models trained with a voxel grid of size 17×17×17 is represented by horizontal bars corresponding to "ens20_17×17×17×2_evo+alt."

Also, in FIG. 29, the y-axis has the different validation sets and the x-axis has p-values. As before, greater p-values, i.e., longer horizontal bars denote greater accuracy in differentiating benign variants from pathogenic variants. As demonstrated by the p-values in FIG. 20, different configurations of PrimateAI 3D outperform PrimateAI across most of the validation sets. That is, the horizontal bars for PrimateAI 3D are mostly longer than the horizontal bars for PrimateAI.

Also, in FIG. 29, a "mean" category along the y-axis calculates the mean of the p-values determined for each of the validation sets. In the mean category as well, the different configurations of PrimateAI 3D outperform PrimateAI.

Figure 30:
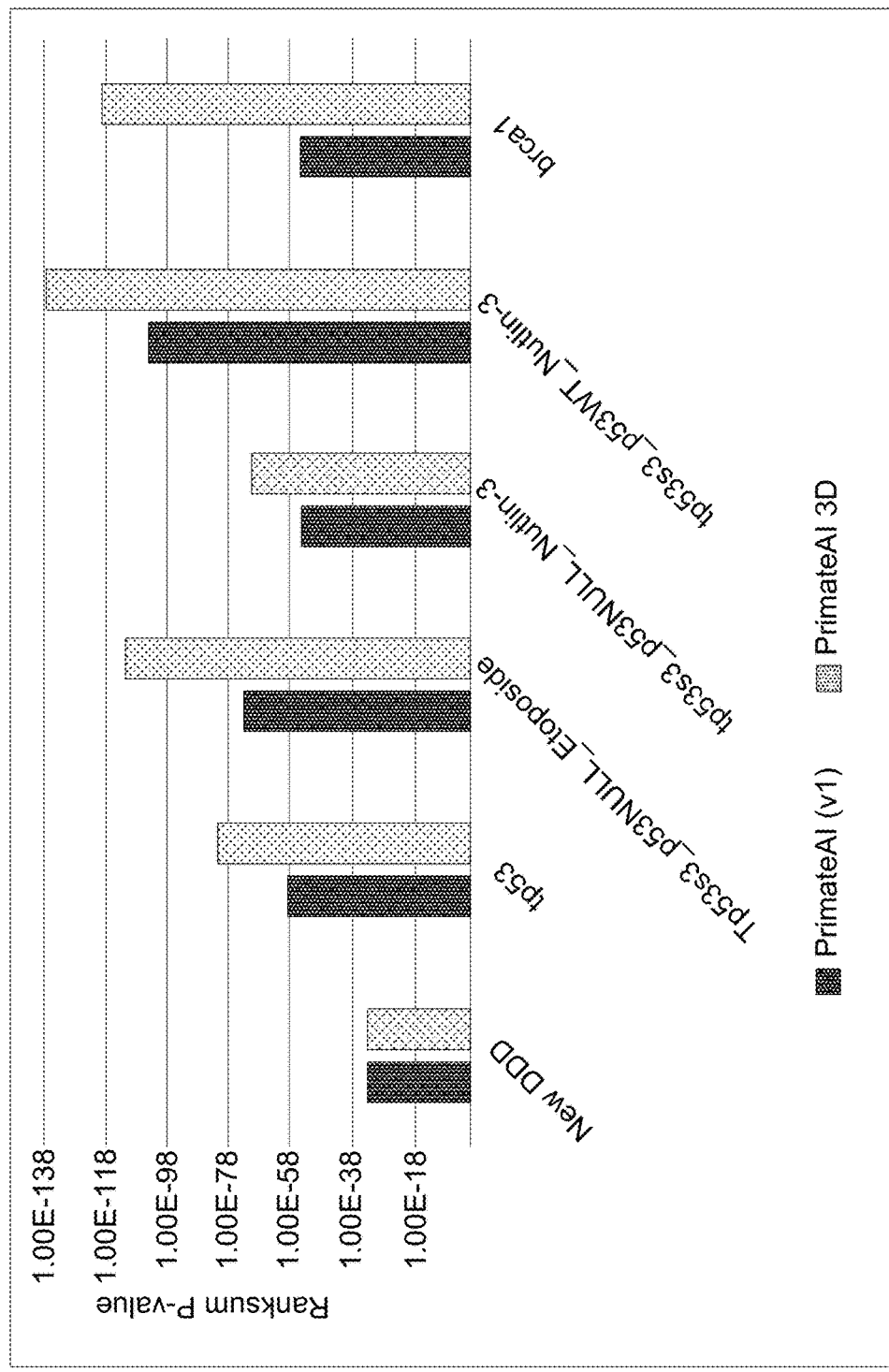

In FIG. 30, the dark vertical bars represent PrimateAI, and the light vertical bars represent PrimateAI 3D. In FIG. 30, the y-axis has p-values, and the x-axis has the different validation sets. In FIG. 30, without exceptions, PrimateAI 3D consistently outperforms PrimateAI across all of the validation sets. That is, the light vertical bars for PrimateAI 3D are always longer than the dark vertical bars for PrimateAI.

Figure 31:
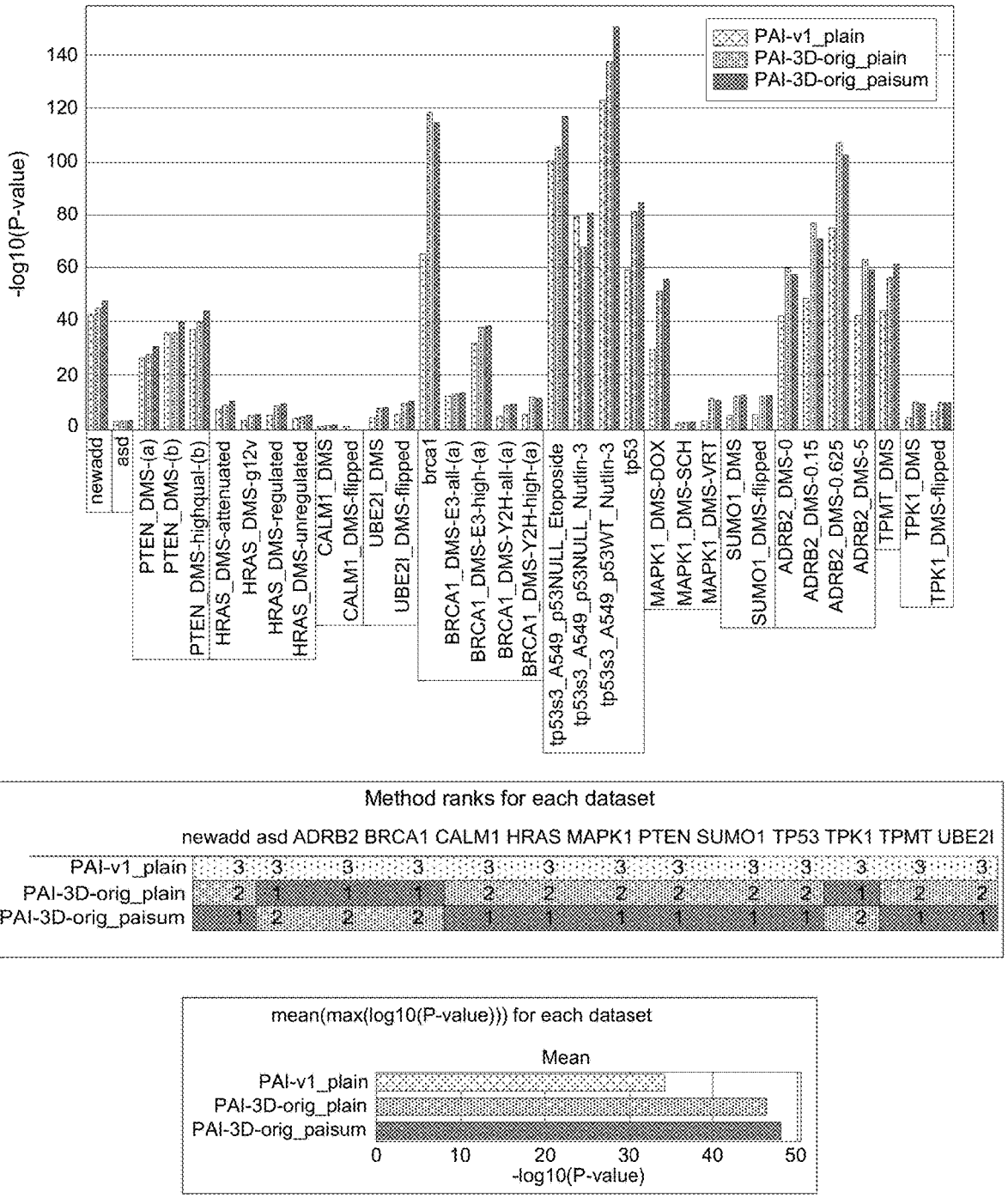
Figure 34:
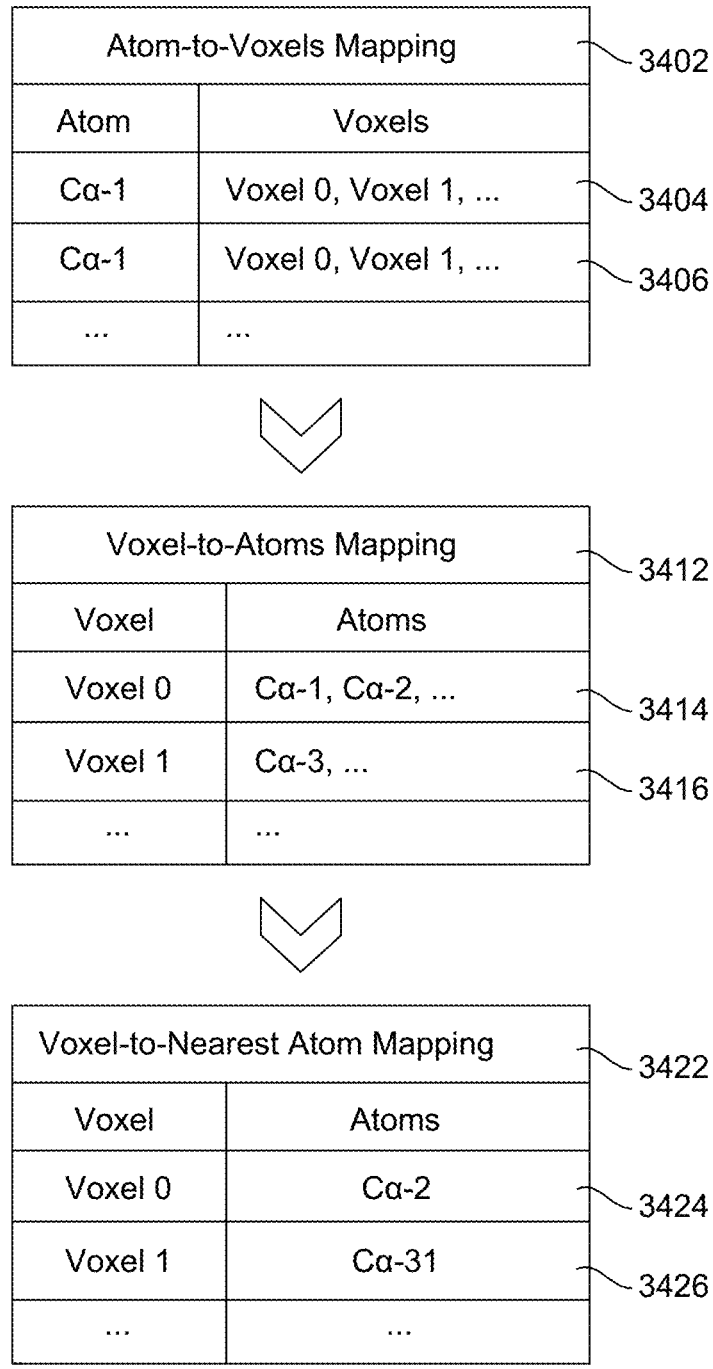
FIG. 34 shows generating voxel-to-atoms mapping from atom-to-voxels mapping to identify nearest atoms on a voxel-by-voxel basis, in accordance with one implementation of the technology disclosed.

FIG. 31 identifies performance of the benchmark PrimateAI model with vertical bars for "PAI-v1_plain" and performance of the disclosed PrimateAI 3D model with vertical bars for "PAI-3D-orig_plain." A third vertical bar, "PAI-3D-orig_paisum," depicts pathogenicity predictions derived by combining respective pathogenicity predictions of the disclosed PrimateAI 3D model and the benchmark PrimateAI model. In FIG. 31, the y-axis has p-values, and the x-axis has the different validation sets.

As demonstrated by the p-values in FIG. 31, PrimateAI 3D outperforms PrimateAI across most of the validation sets (only exception being the tp53s3_A549_p53NULL_Nutlin-3 validation set). That is, the vertical bars for PrimateAI 3D are consistently longer than the vertical bars for PrimateAI.

Also, in FIG. 31, a separate "mean" chart calculates the mean of the p-values determined for each of the validation sets. In the mean chart as well, PrimateAI 3D outperforms PrimateAI.

The mean statistics may be biased by outliers. To address this, a separate "method ranks" chart is also depicted in FIG. 31. Higher rank denotes poorer classification accuracy. In the method ranks chart as well, PrimateAI 3D outperforms PrimateAI by having more counts of lower ranks 1 and 2 versus Primate AI having all 3s.

In FIGS. 28 to 31, it is also evident that combining PrimateAI 3D with PrimateAI produces superior classification accuracy. That is, a protein can be fed as an amino acid sequence to PrimateAI to generate a first output, and the same protein can be fed as a 3D, voxelized protein structure to PrimateAI 3D to generate a second output, and the first and second outputs can be combined or analyzed in aggregate to produce a final pathogenicity prediction for a variant experienced by the protein.

Efficient Voxelization

FIG. 32 is a flowchart illustrating an efficient voxelization process 3200 that efficiently identifies nearest atoms on a voxel-by-voxel basis.

The discussion now revisits the distance channels. As discussed above, the reference amino acid sequence 202 can contain different types of atoms, such as alpha-carbon atoms, beta-carbon atoms, oxygen atoms, nitrogen atoms, hydrogen atoms, and so on. Accordingly, as discussed above, the distance channels can be arranged by nearest alpha-carbon atoms, nearest beta-carbon atoms, nearest oxygen atoms, nearest nitrogen atoms, nearest hydrogen atoms, and so on. For example, in FIG. 6, each of the nine voxels 514 has twenty-one amino acid-wise distance channels for nearest alpha-carbon atoms. FIG. 6 can be further expanded for each of the nine voxels 514 to also have twenty-one amino acid-wise distance channels for nearest beta-carbon atoms, and for each of the nine voxels 514 to also have a nearest generic atom distance channel for a nearest atom irrespective of the type of the atom and the type of the amino acid. This way, each of the nine voxels 514 can have forty-three distance channels.

The discussion now turns to the number of distance calculations required to identify the nearest atoms on a voxel-by-voxel basis for inclusion in the distance channels. Consider the example in FIG. 3 that depicts a total of eight hundred and twenty-eight alpha-carbon atoms distributed across the twenty-one amino acid categories. To calculate the amino acid-wise distance channels 602-642 in FIG. 6, i.e., to determine the one hundred and eighty-nine distance values, distances are measured from each of the nine voxels 514 to each of the eight hundred and twenty-eight alpha-carbon atoms, resulting in 9*828=7,452 distance calculations. In the 3D case of twenty-seven voxels, this results in 27*828=22,356 distance calculations. When the eight hundred and twenty-eight beta-carbon atoms are also included, this number increases to 27*1656=44,712 distance calculations.

Figure 35A:
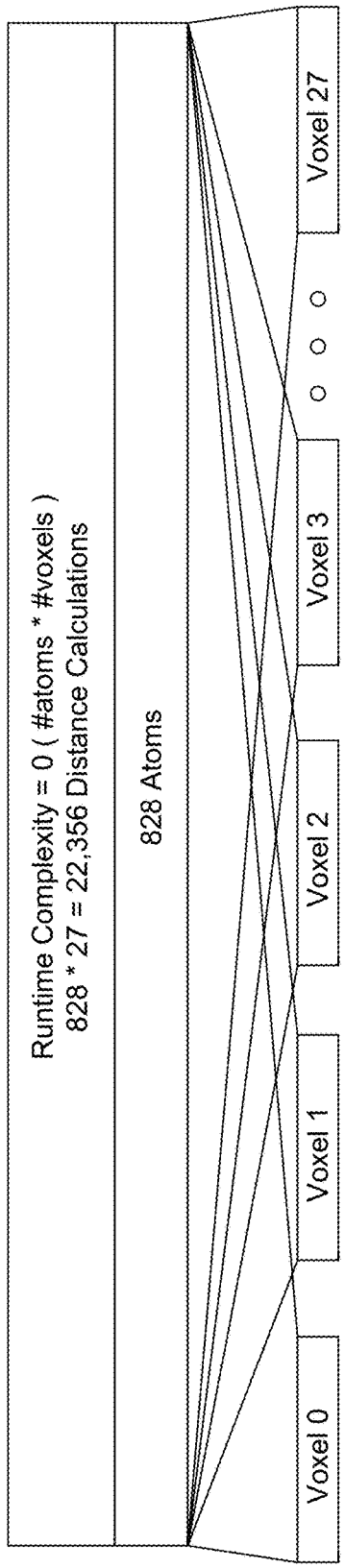
FIGS. 35A and 35B illustrate how the disclosed efficient voxelization has a runtime complexity of O(#atoms) versus the runtime complexity of O(#atoms*#voxels) without the use of disclosed efficient voxelization.

This means that the runtime complexity of identifying the nearest atoms on a voxel-by-voxel basis for a single protein voxelization is O(#atoms*#voxels), as illustrated by FIG. 35A. Furthermore, the runtime complexity for a single protein voxelization increases to O(#atoms*#voxels*#attributes) when the distance channels are calculated across a variety of attributes (e.g., different features or channels per voxel like annotation channels and structural confidence channels).

Consequently, the distance calculations can become the most compute-consuming part of the voxelization process, taking valuable compute resources away from critical runtime tasks like model training and model inference. Consider, for example, the case of model training with a training dataset of 7,000 proteins. Generating distance channels for a plurality of voxels across a plurality of amino acids, atoms, and attributes can involve more than 100 voxelizations per protein, resulting in about 800,000 voxelizations in a single training iteration (epoch). A training run of 20-40 epochs, with rotation of atomic coordinates in each epoch, can result in as many as 32 million voxelizations.

In addition to the high compute cost, the size of the data for 32 million voxelizations is too big to fit in main memory (e.g., >20 TB for a 15×15×15 voxel grid). Considering repeated training runs for parameter optimization and ensemble learning, the memory footprint of the voxelization process gets too big to be stored on disk, making the voxelization process a part of the model training and not a precomputation step.

The technology disclosed provides an efficient voxelization process that achieves up to ~100× speedup over the runtime complexity of O(#atoms*#voxels). The disclosed efficient voxelization process reduces the runtime complexity for a single protein voxelization to O(#atoms). In the case of different features or channels per voxel, the disclosed efficient voxelization process reduces the runtime complexity for a single protein voxelization to O(#atoms*#attributes). As a result, the voxelization process becomes as fast as model training, shifting the computational bottleneck from voxelization back to computing neural network weights on processors such as GPUs, ASICs, TPUs, FPGAs, CGRAs, etc.

In some implementations of the disclosed efficient voxelization process involving large voxel grids, the runtime complexity for a single protein voxelization is O(#atoms+voxels) and O(#atoms*#attributes+voxels) for the case of different features or channels per voxel. The "+voxels" complexity is observed when the number of atoms is minuscule compared to the number of voxels, for example, when there is one atom in a 100×100×100 voxel grid (i.e., one million voxels per atom). In such a scenario, the runtime is dominated by the overhead of the huge number of voxels, for example, for allocating the memory for one million voxels, initialization one million voxels to zero, etc.

The discussion now turns to details of the disclosed efficient voxelization process. FIGS. 32A, 32B, 33, 34, and 35B are discussed in tandem.

Starting with FIG. 32A, at step 3202, each atom (e.g., each of the 828 alpha-carbon atoms and each of the 828 beta-carbon atoms) is associated with a voxel that contains the atom (e.g., one of the nine voxels 514). The term "contains" refers to the 3D atomic coordinates of the atom being located in the voxel. The voxel that contains the atom is also referred to herein as "the atom-containing voxel."

FIGS. 32B and 33 describe how a voxel that contains a particular atom is selected. FIG. 33 uses 2D atomic coordinates as representative of 3D atomic coordinates. Note that the voxel grid 522 is regularly spaced with each of the voxels 514 having a same step size (e.g., 1 angstrom (Å) or 2 Å).

Also, in FIG. 33, the voxel grid 522 has indices [0, 1, 2] along a first dimension (e.g., x-axis) and indices [0, 1, 2] along a second dimension (e.g., y-axis). Also, in FIG. 33, the respective voxels 514 in the voxel 512 are identified by voxel indices [Voxel 0, Voxel 1, . . . , Voxel 8] and by voxel center indices [(1, 1), (1, 2), . . . , (3, 3)].

Also, in FIG. 33, center coordinates of the voxel centers along the first dimension, i.e., first dimension voxel coordinates, are identified with double dash underlines. Also, in FIG. 33, center coordinates of the voxel centers along the second dimension, i.e., second dimension voxel coordinates, are identified with double dash-dot-dot-dash underlines.

First, at step 3202a (Step 1 in FIG. 33), 3D atomic coordinates (1.7456, 2.14323) of the particular atom are quantized to generated quantized 3D atomic coordinates (1.7, 2.1). The quantization can be achieved by rounding or truncation of bits.

Then, at step 3202b (Step 2 in FIG. 33), voxel coordinates (or voxel centers or voxel center coordinates) of the voxels 514 are assigned to the quantized 3D atomic coordinates on a dimension-basis. For the first dimension, the quantized atomic coordinate 1.7 is assigned to Voxel 1 because it covers first dimension voxel coordinates ranging from 1 to 2 and is centered at 1.5 in the first dimension. Note that Voxel 1 has index 1 along the first dimension, in contrast to having index 0 along the second dimension.

For the second dimension, starting from Voxel 1, the voxel grid 522 is traversed along the second dimension. This results in the quantized atomic coordinate 2.5 being assigned to Voxel 7 because it covers second dimension voxel coordinates ranging from 2 to 3 and is centered at 2.5 in the second dimension. Note that Voxel 7 has index 2 along the second dimension, in contrast to having index 1 along the first dimension.

Then, at step 3202c (Step 3 in FIG. 33), dimension indices corresponding to the assigned voxel coordinates are selected. That is, for Voxel 1, index 1 is selected along the first dimension, and, for Voxel 7, index 2 is selected along the second dimension. A person skilled in the art will appreciate that the above steps can be analogously executed for a third dimension to select a dimension index along the third dimension.

Then, at step 3202d (Step 4 in FIG. 33), an accumulated sum is generated based on position-wise weighting the selected dimension indices by powers of a radix. The general idea behind positional numbering systems is that a numeric value is represented through increasing powers of the radix (or base), for example, binary is base two, ternary is base three, octal is base eight, and hexadecimal is base sixteen. This is often referred to as a weighted numbering system because each position is weighted by a power of the radix. The set of valid numericals for a positional numbering system is equal in size to the radix of that system. For example, there are ten digits in the decimal system, zero through nine, and three digits in the ternary system, zero, one, and two. The largest valid number in a radix system is one smaller than the radix (so eight is not a valid numerical in any radix system smaller than nine). Any decimal integer can be expressed exactly in any other integral base system, and vice-versa.

Returning to the example in FIG. 33, the selected dimension indices 1 and 2 are converted to a single integer by position-wise multiplying them with respective powers of base three and summing the results of the position-wise multiplications. Base three is selected here because the 3D atomic coordinates have three dimensions (although FIG. 33 shows only 2D atomic coordinates along two dimensions for simplicity's sake).

Since index 2 is positioned at the rightmost bit (i.e., the least significant bit), it is multiplied by three to the power of zero to yield two. Since index 1 is positioned at the second rightmost bit (i.e., the second least significant bit), it is multiplied by three to the power of one to yield three. This results in the accumulated sum being five.

Then, at step 3202e (Step 5 in FIG. 33), based on the accumulated sum, a voxel index of the voxel containing the particular atom is selected. That is, the accumulated sum is interpreted as the voxel index of the voxel containing the particular atom.

At step 3212, after each atom is associated with the atom-containing voxel, each atom is further associated with one or more voxels that are in a neighborhood of the atom-containing voxel, also referred to herein as "neighborhood voxels." The neighborhood voxels can be selected based on being within a predefined radius of the atom-containing voxel (e.g., 5 angstrom (Å)). In other implementations, the neighborhood voxels can be selected based on being contiguously adjacent to the atom-containing voxel (e.g., top, bottom, right, left adjacent voxels). The resulting association that associates each atom with the atom-containing voxel and the neighborhood voxels is encoded in an atom-to-voxels mapping 3402, also referred to herein as element-to-cells mapping. In one example, a first alpha-carbon atom is associated with a first subset of voxels 3404 that includes an atom-containing voxel and neighborhood voxels for the first alpha-carbon atom. In another example, a second alpha-carbon atom is associated with a second subset of voxels 3406 that includes an atom-containing voxel and neighborhood voxels for the second alpha-carbon atom.

Note that no distance calculations are made to determine the atom-containing voxel and the neighborhood voxels. The atom-containing voxel is selected by virtue of the spatial arrangement of the voxels that allows assignment of quantized 3D atomic coordinates to corresponding regularly spaced voxel centers in the voxel grid (without using any distance calculations). Also, the neighborhood voxels are selected by virtue of being spatially contiguous to the atom-containing voxel in the voxel grid (again without using any distance calculations).

At step 3222, each voxel is mapped to atoms to which it was associated at steps 3202 and 3212. In one implementation, this mapping is encoded in a voxel-to-atoms mapping 3412, which is generated based on the atom-to-voxels mapping 3402 (e.g., by applying a voxel-based sorting key on the atom-to-voxels mapping 3402). The voxel-to-atoms mapping 3412 is also referred to herein as "cell-to-elements mapping." In one example, a first voxel is mapped to a first subset of alpha-carbon atoms 3414 that includes alpha-carbon atoms associated with the first voxel at steps 3202 and 3212. In another example, a second voxel is mapped to a second subset of alpha-carbon atoms 3416 that includes alpha-carbon atoms associated with the second voxel at steps 3202 and 3212.

At step 3232, for each voxel, distances are calculated between the voxel and atoms mapped to the voxel at step 3222. Step 3232 has a runtime complexity of O(#atoms) because distance to a particular atom is measured only once from a respective voxel to which the particular atom is uniquely mapped in the voxel-to-atoms mapping 3412. This is true when no neighboring voxels are considered. Without neighbors, the constant factor that is implied in the big-O notation is 1. With neighbors, the big-O notation is equal to the number of neighbors+1 since the number of neighbors is constant for each voxel, and therefore the runtime complexity of O(#atoms) remains true. In contrast, in FIG. 35A, distances to a particular atom are redundantly measured as many times as the number of voxels (e.g., 27 distances for a particular atom due to 27 voxels).

Figure 35B:
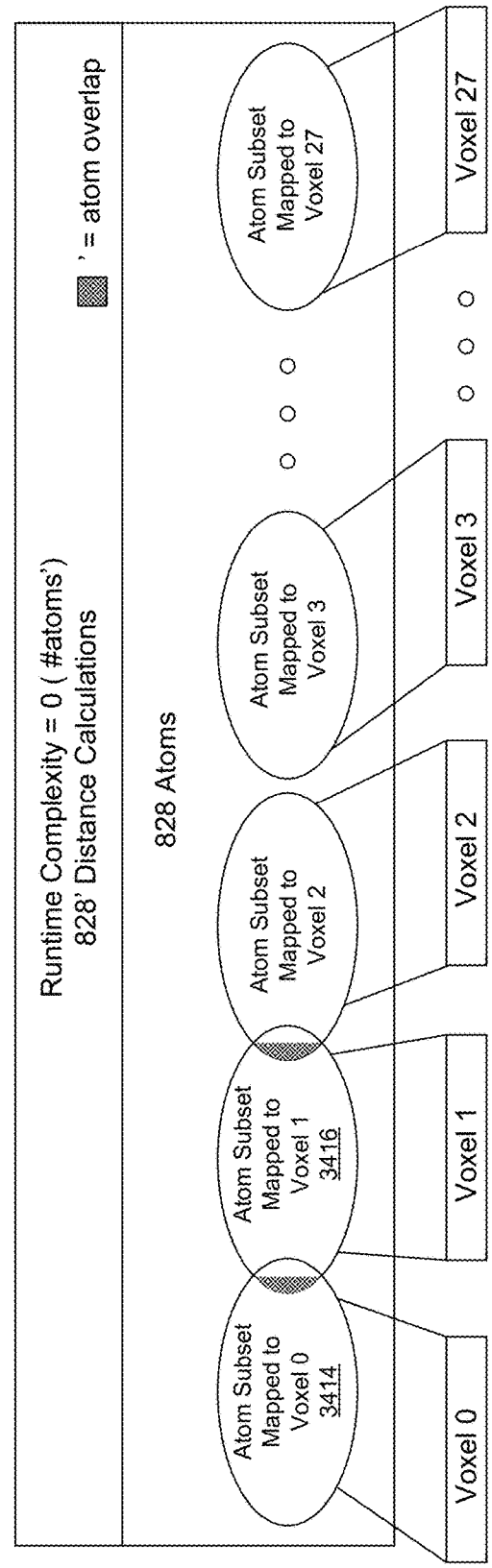

In FIG. 35B, based on the voxel-to-atoms mapping 3412, each voxel is mapped to a respective subset of the 828 atoms (not including distance calculations to neighborhood voxels), as illustrated by respective ovals for respective voxels. The respective subsets are largely non-overlapping, with some exceptions. Insignificant overlap exists due to some instances when multiple atoms are mapped to a same voxel, as indicated in FIG. 35B by the prime symbol "'" and the shaded overlap between the ovals. This minimal overlap has an additive effect on the runtime complexity of O(#atoms) and not a multiplicative effect. This overlap is a result of considering neighboring voxels, after determining the voxel that contains the atom. Without neighboring voxels, there can be no overlap, because an atom is only associated with one voxel. Considering neighbors, however, each neighbor could potentially be associated with the same atom (as long as there is no other atom of the same amino acid that is closer).

At step 3242, for each voxel, based on the distances calculated at step 3232, a nearest atom to the voxel is identified. In one implementation, this identification is encoded in a voxel-to-nearest atom mapping 3422, also referred to herein as "cell-to-nearest element mapping." In one example, the first voxel is mapped to a second alpha-carbon atom as its nearest alpha-carbon atom 3424. In another example, the second voxel is mapped to a thirty-first alpha-carbon atom as its nearest alpha-carbon atom 3426.

Furthermore, as the voxel-wise distances are calculated using the technique discussed above, the atom-type and amino acid-type categorization of the atoms and the corresponding distance values are stored to generate categorized distance channels.

Once the distances to nearest atoms are identified using the technique discussed above, these distances can be encoded in the distance channels for voxelization and subsequent processing by the pathogenicity classifier 2104.

Computer System

Figure 36:
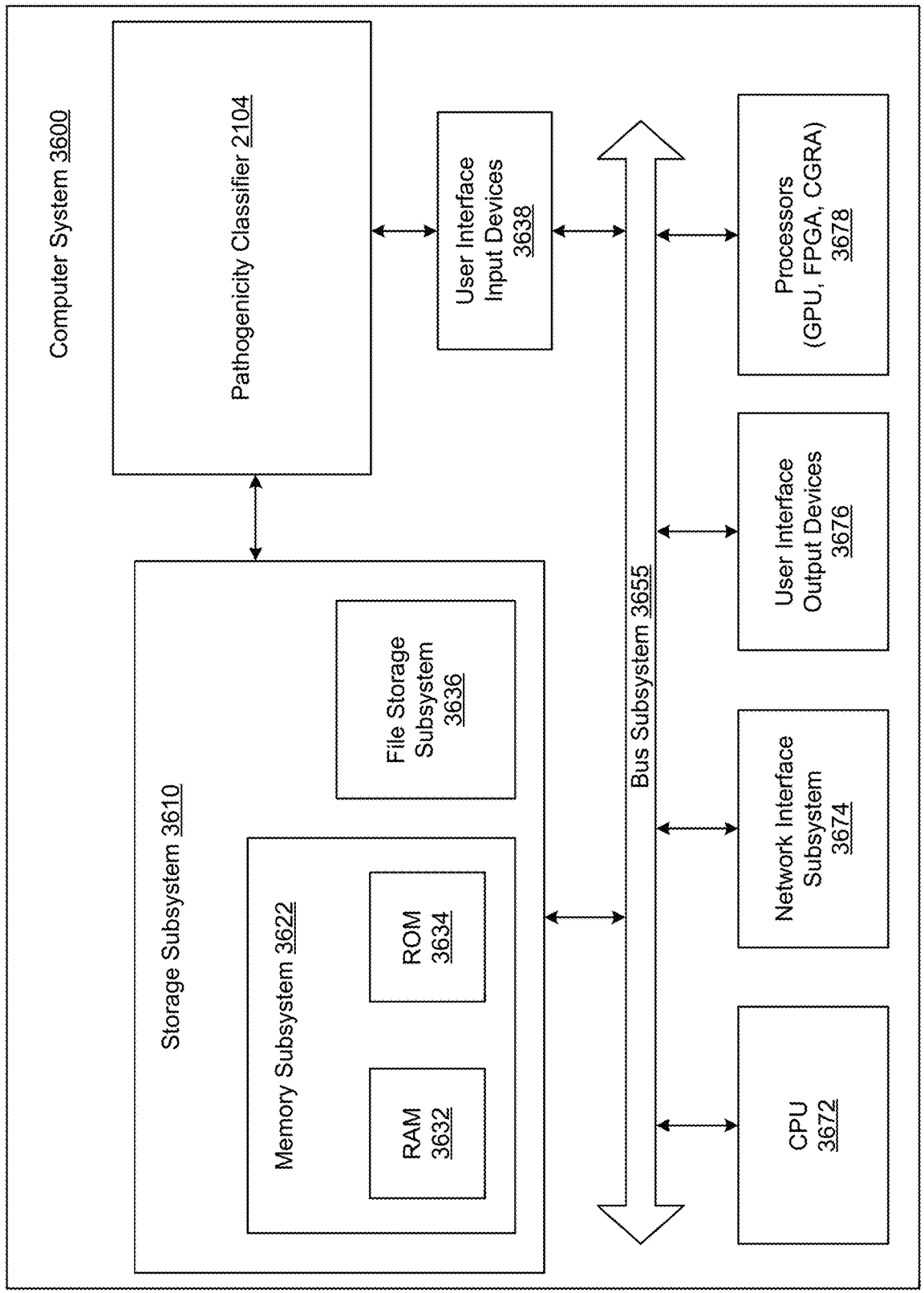
FIG. 36 shows an example computer system that can be used to implement the technology disclosed.

FIG. 36 shows an example computer system 3600 that can be used to implement the technology disclosed. Computer system 3600 includes at least one central processing unit (CPU) 3672 that communicates with a number of peripheral devices via bus subsystem 3655. These peripheral devices can include a storage subsystem 3610 including, for example, memory devices and a file storage subsystem 3636, user interface input devices 3638, user interface output devices 3676, and a network interface subsystem 3674. The input and output devices allow user interaction with computer system 3600. Network interface subsystem 3674 provides an interface to outside networks, including an interface to corresponding interface devices in other computer systems.

In one implementation, the pathogenicity classifier 2104 is communicably linked to the storage subsystem 3610 and the user interface input devices 3638.

User interface input devices 3638 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 3600.

User interface output devices 3676 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 3600 to the user or to another machine or computer system.

Storage subsystem 3610 stores programming and data constructs that provide the functionality of some or all of the modules and methods described herein. These software modules are generally executed by processors 3678.

Processors 3678 can be graphics processing units (GPUs), field-programmable gate arrays (FPGAs), application-specific integrated circuits (ASICs), and/or coarse-grained reconfigurable architectures (CGRAs). Processors 3678 can be hosted by a deep learning cloud platform such as Google Cloud Platform™, Xilinx™, and Cirrascale™. Examples of processors 3678 include Google's Tensor Processing Unit (TPU)™, rackmount solutions like GX4 Rackmount Series™, GX36 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 3622 used in the storage subsystem 3610 can include a number of memories including a main random access memory (RAM) 3632 for storage of instructions and data during program execution and a read only memory (ROM) 3634 in which fixed instructions are stored. A file storage subsystem 3636 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 3636 in the storage subsystem 3610, or in other machines accessible by the processor.

Bus subsystem 3655 provides a mechanism for letting the various components and subsystems of computer system 3600 communicate with each other as intended. Although bus subsystem 3655 is shown schematically as a single bus, alternative implementations of the bus subsystem can use multiple busses.

Computer system 3600 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 3600 depicted in FIG. 36 is intended only as a specific example for purposes of illustrating the preferred implementations of the present invention. Many other configurations of computer system 3600 are possible having more or less components than the computer system depicted in FIG. 36.

Particular Implementations 1

The following implementations can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Though the technology disclosed uses 3D data as input, in other implementations, it can analogously use 1D data, 2D data (e.g., pixels and 2D atomic coordinates), 4D data, 5D data, and so on.

In some implementations, a system comprises memory storing amino acid-wise distance channels for a plurality of amino acids in a protein. Each of the amino acid-wise distance channels has voxel-wise distance values for voxels in a plurality of voxels. The voxel-wise distance values specify distances from corresponding voxels in the plurality of voxels to atoms of corresponding amino acids in the plurality of amino acids. The system further comprises a pathogenicity determination engine configured to process a tensor that includes the amino acid-wise distance channels and an alternative allele of the protein expressed by a variant. The pathogenicity determination engine can also be configured to determine a pathogenicity of the variant based at least in part on the tensor.

In some implementations, the system further comprises a distance channels generator that centers a voxel grid of the voxels on an alpha-carbon atom of respective residues of the amino acids. The distance channels generator can center the voxel grid on an alpha-carbon atom of a residue of a particular amino acid that positioned at a variant amino acid in the protein.

The system can be configured to encode, in the tensor, a directionality of the amino acids and a position of the particular amino acid by multiplying, with a directionality parameter, voxel-wise distance values for those amino acids that precede the particular amino acid. The distances can be nearest-atom distances from corresponding voxel centers in the voxel grid to nearest atoms of the corresponding amino acids. In some implementations, the nearest-atom distances can be Euclidean distances. The nearest-atom distances can be normalized by dividing the Euclidean distances with a maximum nearest-atom distance. The amino acids can have alpha-carbon atoms and, in some implementations, the distances can be nearest-alpha-carbon atom distances from the corresponding voxel centers to nearest alpha-carbon atoms of the corresponding amino acids. The amino acids can have beta-carbon atoms and, in some implementations, the distances can be nearest-beta-carbon atom distances from the corresponding voxel centers to nearest beta-carbon atoms of the corresponding amino acids. The amino acids can have backbone atoms and, in some implementations, the distances can be nearest-backbone atom distances from the corresponding voxel centers to nearest backbone atoms of the corresponding amino acids. The amino acids have side chain atoms and, in some implementations, the distances can be nearest-sidechain atom distances from the corresponding voxel centers to nearest sidechain atoms of the corresponding amino acids.

The system can further be configured to encode, in the tensor, a nearest atom channel that specifies a distance from each voxel to a nearest atom. The nearest atom can be selected irrespective of the amino acids and atomic elements of the amino acids. In some implementations, the distance is a Euclidean distance. The distance can be normalized by dividing the Euclidean distance with a maximum distance. The amino acids can include non-standard amino acids. The tensor can include an absentee atom channel that specifies atoms not found within a predefined radius of a voxel center, and the absentee atom channel can be one-hot encoded. In some implementations, the tensor can further include a one-hot encoding of the alternative allele that is voxel-wise encoded to each of the amino acid-wise distance channels. The tensor can further include a reference allele of the protein. In some implementations, the tensor can further include a one-hot encoding of the reference allele that is voxel-wise encoded to each of the amino acid-wise distance channels. The tensor can further include evolutionary profiles that specify conservation levels of the amino acids across a plurality of species.

The system can further comprise an evolutionary profiles generator that, for each of the voxels, selects a nearest atom across the amino acids and the atom categories, selects a pan-amino acid conservation frequencies sequence for a residue of an amino acid that includes the nearest atom, and makes the pan-amino acid conservation frequencies sequence available as one of the evolutionary profiles. The pan-amino acid conservation frequencies sequence can be configured for a particular position of the residue as observed in the plurality of species. The pan-amino acid conservation frequencies sequence can specify whether there is a missing conservation frequency for a particular amino acid. In some implementations, the evolutionary profiles generator, for each of the voxels, can select respective nearest atoms in respective ones of the amino acids, can select respective per-amino acid conservation frequencies for respective residues of the amino acids that include the nearest atoms, and can make the per-amino acid conservation frequencies available as one of the evolutionary profiles. The per-amino acid conservation frequencies can be configured for a particular position of the residues as observed in the plurality of species. The per-amino acid conservation frequencies can specify whether there is a missing conservation frequency for a particular amino acid.

In some implementations of the system, the tensor can further include annotation channels for the amino acids. The annotation channels can be one-hot encoded in the tensor. The annotation channels can be molecular processing annotations that include initiator methionine, signal, transit peptide, propeptide, chain, and peptide. The annotation channels can be regions annotations that include topological domain, transmembrane, intramembrane, domain, repeat, calcium binding, zinc finger, deoxyribonucleic acid (DNA) binding, nucleotide binding, region, coiled coil, motif, and compositional bias. The annotation channels can be sites annotations that include active site, metal binding, binding site, and site. The annotation channels can be amino acid modifications annotations that include non-standard residue, modified residue, lipidation, glycosylation, disulfide bond, and cross-link. The annotation channels can be secondary structure annotations that include helix, turn, and beta strand. The annotation channels can be experimental information annotations that include mutagenesis, sequence uncertainty, sequence conflict, non-adjacent residues, and non-terminal residue.

In some implementations of the system, the tensor further includes structure confidence channels for the amino acids that specify quality of respective structures of the amino acids. The structure confidence channels can be global model quality estimations (GMQEs). The structure confidence channels can include qualitative model energy analysis (QMEAN) scores. The structure confidence channels can be temperature factors that specify a degree to which the residues satisfy physical constraints of respective protein structures. The structure confidence channels can be template structures alignments that specify a degree to which residues of atoms nearest to the voxels have aligned template structures. The structure confidence channels can be template modeling scores of the aligned template structures. The structure confidence channels can be a minimum one of the template modeling scores, a mean of the template modeling scores, and a maximum one of the template modeling scores.

In some implementations, the system can further comprise a tensor generator that voxel-wise concatenates amino acid-wise distance channels for the alpha-carbon atoms with the one-hot encoding of the alternative allele to generate the tensor. The tensor generator can voxel-wise concatenate amino acid-wise distance channels for the beta-carbon atoms with the one-hot encoding of the alternative allele to generate the tensor. The tensor generator can voxel-wise concatenate the amino acid-wise distance channels for the alpha-carbon atoms, the amino acid-wise distance channels for the beta-carbon atoms, and the one-hot encoding of the alternative allele to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, and pan-amino acid conservation frequencies to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the pan-amino acid conservation frequencies, and the annotation channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the pan-amino acid conservation frequencies, the annotation channels, and the structure confidence channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, and per-amino acid conservation frequencies for each of the amino acids to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, per-amino acid conservation frequencies for each of the amino acids, and the annotation channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, per-amino acid conservation frequencies for each of the amino acids, the annotation channels, and the structure confidence channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, and the one-hot encoding of the reference allele to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, and the pan-amino acid conservation frequencies to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, the pan-amino acid conservation frequencies, and the annotation channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, the pan-amino acid conservation frequencies, the annotation channels, and the structure confidence channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, and the per-amino acid conservation frequencies for each of the amino acids to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, the per-amino acid conservation frequencies for each of the amino acids, and the annotation channels to generate the tensor. The tensor generator can voxel-wise concatenate the amino acid-wise distance channels for the alpha-carbon atoms, the amino acid-wise distance channels for the beta-carbon atoms, the one-hot encoding of the alternative allele, the one-hot encoding of the reference allele, the per-amino acid conservation frequencies for each of the amino acids, the annotation channels, and the structure confidence channels to generate the tensor.

In some implementations, the system can further comprise an atoms rotation engine that rotates atoms of the amino acids before the amino acid-wise distance channels are generated. The pathogenicity determination engine can be a neural network. In particular implementations, the pathogenicity determination engine can be a convolutional neural network. The convolutional neural network can use 1×1×1 convolutions, 3×3×3 convolutions, rectified linear unit activation layers, batch normalization layers, a fully-connected layer, a dropout regularization layer, and a softmax classification layer. The 1×1×1 convolutions and the 3×3×3 convolutions can be three-dimensional convolutions.

In some implementations, a layer of the 1×1×1 convolutions can process the tensor and produce an intermediate output that is a convolved representation of the tensor. A sequence of layers of the 3×3×3 convolutions can process the intermediate output and produce a flattened output. The fully-connected layer can process the flattened output and produce unnormalized outputs. The softmax classification layer can process the unnormalized outputs and produce exponentially normalized outputs that identify likelihoods of the variant being pathogenic and benign. A sigmoid layer can process the unnormalized outputs and produce a normalized output that identifies a likelihood of the variant being pathogenic. The voxels, the atoms, and the distances can have three-dimensional coordinates. The tensor can have at least three dimensions, the intermediate output can have at least three dimensions, and the flattened output can have one dimension.

In some implementations, the pathogenicity determination engine is a recurrent neural network. In other implementations, the pathogenicity determination engine is an attention-based neural network. In still other implementations, the pathogenicity determination engine is a gradient-boosted tree. In still other implementations, the pathogenicity determination engine is a state vector machine.

In other implementations, a system can comprise memory storing atom category-wise distance channels for amino acids in a protein. The amino acids can have atoms for a plurality of atom categories, and atom categories in the plurality of atom categories can specify atomic elements of the amino acids. The atom category-wise distance channels can have voxel-wise distance values for voxels in a plurality of voxels. The voxel-wise distance values can specify distances from corresponding voxels in the plurality of voxels to atoms in corresponding atom categories in the plurality of atom categories. The system can further comprise a pathogenicity determination engine configured to process a tensor that includes the atom category-wise distance channels and an alternative allele of the protein expressed by a variant, and to determine a pathogenicity of the variant based at least in part on the tensor.

The system can further comprise a distance channels generator that centers a voxel grid of the voxels on respective atoms of respective atom categories in the plurality of atom categories. The distance channels generator can center the voxel grid on an alpha-carbon atom of a residue of at least one variant amino acid in the protein. The distances can be nearest-atom distances from corresponding voxel centers in the voxel grid to nearest atoms in the corresponding atom categories. The nearest-atom distances can be Euclidean distances. The nearest-atom distances can be normalized by dividing the Euclidean distances with a maximum nearest-atom distances. The distances can be nearest-atom distances from the corresponding voxel centers in the voxel grid to nearest atoms irrespective of the amino acids and the atom categories of the amino acids. The nearest-atom distances can be Euclidean distances. The nearest-atom distances can be normalized by dividing the Euclidean distances with a maximum nearest-atom distances.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

1. A computer-implemented method, comprising:
   storing amino acid-wise distance channels for a plurality of amino acids in a protein,
      wherein each of the amino acid-wise distance channels has voxel-wise distance values for voxels in a plurality of voxels, and
      wherein the voxel-wise distance values specify distances from corresponding voxels in the plurality of voxels to atoms of corresponding amino acids in the plurality of amino acids;
   processing a tensor that includes the amino acid-wise distance channels and an alternative allele of the protein expressed by a variant; and
   determining a pathogenicity of the variant based at least in part on the tensor.

2. The computer-implemented method of claim 1, further comprising centering a voxel grid of the voxels on an alpha carbon atom of respective residues of the amino acids.

3. The computer-implemented method of claim 2, further comprising centering the voxel grid on an alpha carbon atom of a residue of a particular amino acid that corresponds to at least one variant amino acid in the protein.

4. The computer-implemented method of claim 3, further comprising encoding, in the tensor, a directionality of the amino acids and a position of the particular amino acid by multiplying, with a directionality parameter, voxel-wise distance values for those amino acids that precede the particular amino acid.

5. The computer-implemented method of claim 3, wherein the distances are nearest-atom distances from corresponding voxel centers in the voxel grid to nearest atoms of the corresponding amino acids.

6. The computer-implemented method of claim 5, wherein the nearest-atom distances are Euclidean distances.

7. The computer-implemented method of claim 6, wherein the nearest-atom distances are normalized by dividing the Euclidean distances with a maximum nearest-atom distance.

8. The computer-implemented method of claim 5, wherein the amino acids have alpha carbon atoms, and wherein the distances are nearest-alpha carbon atom distances from the corresponding voxel centers to nearest alpha carbon atoms of the corresponding amino acids.

9. The computer-implemented method of claim 5, wherein the amino acids have beta carbon atoms and wherein the distances are nearest-beta carbon atom distances from the corresponding voxel centers to nearest beta carbon atoms of the corresponding amino acids.

10. The computer-implemented method of claim 5, wherein the amino acids have backbone atoms and wherein the distances are nearest-backbone atom distances from the corresponding voxel centers to nearest backbone atoms of the corresponding amino acids.

11. The computer-implemented method of claim 5, wherein the amino acids have sidechain atom and wherein the distances are nearest-sidechain atom distances from the corresponding voxel centers to nearest sidechain atoms of the corresponding amino acids.

12. The computer-implemented method of claim 3, further comprising encoding, in the tensor, a nearest atom channel that specifies a distance from each voxel to a nearest atom, wherein the nearest atom is selected irrespective of the amino acids and atomic elements of the amino acids.

13. The computer-implemented method of claim 12, wherein the distance is a Euclidean distance.

14. The computer-implemented method of claim 13, wherein the distance is normalized by dividing the Euclidean distance with a maximum distance.

15. The computer-implemented method of claim 12, wherein the amino acids include non-standard amino acids.

16. The computer-implemented method of claim 1, wherein the tensor further includes an absentee atom channel that specifies atoms not found within a predefined radius of a voxel center, and wherein the absentee atom channel is one-hot encoded.

17. The computer-implemented method of claim 1, wherein the tensor further includes a one-hot encoding of the alternative allele that is voxel-wise encoded to each of the amino acid-wise distance channels.

18. The computer-implemented method of claim 1, wherein the tensor further includes a reference allele of the protein.

19. The computer-implemented method of claim 18, wherein the tensor further includes a one-hot encoding of the reference allele that is voxel-wise encoded to each of the amino acid-wise distance channels.

20. The computer-implemented method of claim 1, wherein the tensor further includes evolutionary profiles that specify conservation levels of the amino acids across a plurality of species.

21. The computer-implemented method of claim 20, further comprising, for each of the voxels,
selecting a nearest atom across the amino acids and the atom categories,
selecting a pan-amino acid conservation frequencies sequence for a residue of an amino acid that includes the nearest atom, and
making the pan-amino acid conservation frequencies sequence available as one of the evolutionary profiles.

22. The computer-implemented method of claim 21, wherein the pan-amino acid conservation frequencies sequence is configured for a particular position of the residue as observed in the plurality of species.

23. The computer-implemented method of claim 21, wherein the pan-amino acid conservation frequencies sequence specifies whether there is a missing conservation frequency for a particular amino acid.

24. The computer-implemented method of claim 21, further comprising, for each of the voxels,
selecting respective nearest atoms in respective ones of the amino acids,
selecting respective per-amino acid conservation frequencies for respective residues of the amino acids that include the nearest atoms, and
making the per-amino acid conservation frequencies available as one of the evolutionary profiles.

25. The computer-implemented method of claim 24, wherein the per-amino acid conservation frequencies are configured for a particular position of the residues as observed in the plurality of species.

26. The computer-implemented method of claim 24, wherein the per-amino acid conservation frequencies specify whether there is a missing conservation frequency for a particular amino acid.

27. The computer-implemented method of claim 1, wherein the tensor further includes annotation channels for the amino acids, wherein the annotation channels are one-hot encoded in the tensor.

28. The computer-implemented method of claim 27, wherein the annotation channels are molecular processing annotations that include initiator methionine, signal, transit peptide, propeptide, chain, and peptide.

29. The computer-implemented method of claim 27, wherein the annotation channels are regions annotations that include topological domain, transmembrane, intramembrane, domain, repeat, calcium binding, zinc finger, deoxyribonucleic acid (DNA) binding, nucleotide binding, region, coiled coil, motif, and compositional bias.

30. The computer-implemented method of claim 27, wherein the annotation channels are sites annotations that include active site, metal binding, binding site, and site.

31. The computer-implemented method of claim 27, wherein the annotation channels are amino acid modifications annotations that include non-standard residue, modified residue, lipidation, glycosylation, disulfide bond, and cross-link.

32. The computer-implemented method of claim 27, wherein the annotation channels are secondary structure annotations that include helix, turn, and beta strand.

33. The computer-implemented method of claim 27, wherein the annotation channels are experimental information annotations that include mutagenesis, sequence uncertainty, sequence conflict, non-adjacent residues, and non-terminal residue.

34. The computer-implemented method of claim 1, wherein the tensor further includes structure confidence channels for the amino acids that specify quality of respective structures of the amino acids.

35. The computer-implemented method of claim 34, wherein the structure confidence channels are global model quality estimations (GMQEs).

36. The computer-implemented method of claim 34, wherein the structure confidence channels include qualitative model energy analysis (QMEAN) scores.

37. The computer-implemented method of claim 34, wherein the structure confidence channels are temperature factors that specify a degree to which the residues satisfy physical constraints of respective protein structures.

38. The computer-implemented method of claim 34, wherein the structure confidence channels are template structures alignments that specify a degree to which residues of atoms nearest to the voxels have aligned template structures.

39. The computer-implemented method of claim 38, wherein the structure confidence channels are template modeling scores of the aligned template structures.

40. The computer-implemented method of claim 39, wherein the structure confidence channels are a minimum one of the template modeling scores, a mean of the template modeling scores, and a maximum one of the template modeling scores.

41. The computer-implemented method of claim 1, further comprising voxel-wise concatenating amino acid-wise distance channels for the alpha carbon atoms with the one-hot encoding of the alternative allele to generate the tensor.

42. The computer-implemented method of claim 41, further comprising voxel-wise concatenating amino acid-wise distance channels for the beta carbon atoms with the one-hot encoding of the alternative allele to generate the tensor.

43. The computer-implemented method of claim 42, further comprising voxel-wise concatenating the amino acid-wise distance channels for the alpha carbon atoms, the amino acid-wise distance channels for the beta carbon atoms, and the one-hot encoding of the alternative allele to generate the tensor.

44. The computer-implemented method of claim 43, further comprising voxel-wise concatenating the amino acid-wise distance channels for the alpha carbon atoms, the amino acid-wise distance channels for the beta carbon atoms, the one-hot encoding of the alternative allele, and pan-amino acid conservation frequencies sequences to generate the tensor.

45. The computer-implemented method of claim 44, further comprising voxel-wise concatenating the amino acid-wise distance channels for the alpha carbon atoms, the amino acid-wise distance channels for the beta carbon atoms, the one-hot encoding of the alternative allele, the pan-amino acid conservation frequencies sequences, and the annotation channels to generate the tensor.

46. The computer-implemented method of claim 45, further comprising voxel-wise concatenating the amino acid-wise distance channels for the alpha carbon atoms, the amino acid-wise distance channels for the beta carbon atoms, the one-hot encoding of the alternative allele, the pan-amino acid conservation frequencies sequences, the annotation channels, and the structure confidence channels to generate the tensor.

47. The computer-implemented method of claim 46, further comprising voxel-wise concatenating the amino acid-wise distance channels for the alpha carbon atoms, the amino acid-wise distance channels for the beta carbon atoms, the one-hot encoding of the alternative allele, and per-amino acid conservation frequencies for each of the amino acids to generate the tensor.

48. The computer-implemented method of claim 47, further comprising voxel-wise concatenating the amino acid-wise distance channels for the alpha carbon atoms, the amino acid-wise distance channels for the beta carbon atoms, the one-hot encoding of the alternative allele, per-amino acid conservation frequencies for each of the amino acids, and the annotation channels to generate the tensor.

49. The computer-implemented method of claim 48, further comprising voxel-wise concatenating the amino acid-wise distance channels for the alpha carbon atoms, the amino acid-wise distance channels for the beta carbon atoms, the one-hot encoding of the alternative allele, per-amino acid conservation frequencies for each of the amino acids, the annotation channels, and the structure confidence channels to generate the tensor.

50. The computer-implemented method of claim 49, further comprising voxel-wise concatenating the amino acid-wise distance channels for the alpha carbon atoms, the amino acid-wise distance channels for the beta carbon atoms, the one-hot encoding of the alternative allele, and the one-hot encoding of the reference allele to generate the tensor.

51. The computer-implemented method of claim 50, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, and the pan-amino acid conservation frequencies sequences to generate the tensor.

52. The computer-implemented method of claim 51, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the pan-amino acid conservation frequencies sequences, and the annotation channels to generate the tensor.

53. The computer-implemented method of claim 52, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the pan-amino acid conservation frequencies sequences, the annotation channels, and the structure confidence channels to generate the tensor.

54. The computer-implemented method of claim 53, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, and the per-amino acid conservation frequencies for each of the amino acids to generate the tensor.

55. The computer-implemented method of claim 54, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the per-amino acid conservation frequencies for each of the amino acids, and the annotation channels to generate the tensor.

56. The computer-implemented method of claim 55, further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the per-amino acid conservation frequencies for each of the amino acids, the annotation channels, and the structure confidence channels to generate the tensor.

57. The computer-implemented method of claim 1, further comprising rotating atoms of the amino acids before the amino acid-wise distance channels are generated.

58. The computer-implemented method of claim 1, further comprising using 1×1×1 convolutions, 3×3×3 convolutions, rectified linear unit activation layers, batch normalization layers, a fully-connected layer, a dropout regularization layer, and a softmax classification layer in a convolutional neural network.

59. The computer-implemented method of claim 58, wherein the 1×1×1 convolutions and the 3×3×3 convolutions are three-dimensional convolutions.

60. The computer-implemented method of claim 58, wherein a layer of the 1×1×1 convolutions processes the tensor and produces an intermediate output that is a convolved representation of the tensor, wherein a sequence of layers of the 3×3×3 convolutions processes the intermediate output and produces a flattened output, wherein the fully-connected layer processes the flattened output and produces unnormalized outputs, and wherein the softmax classification layer processes the unnormalized outputs and produces exponentially normalized outputs that identify likelihoods of the variant being pathogenic and benign.

61. The computer-implemented method of claim 60, wherein a sigmoid layer processes the unnormalized outputs and produces a normalized output that identifies a likelihood of the variant being pathogenic.

62. The computer-implemented method of claim 60, wherein the voxels, the atoms, and the distances have three-dimensional coordinates, wherein the tensor has at least three dimensions, wherein the intermediate output has at least three dimensions, and wherein the flattened output has one dimension.

63. A computer-implemented method, comprising:
storing atom category-wise distance channels for amino acids in a protein,
wherein the amino acids have atoms for a plurality of atom categories,
wherein atom categories in the plurality of atom categories specify atomic elements of the amino acids,
wherein each of the atom category-wise distance channels has voxel-wise distance values for voxels in a plurality of voxels, and
wherein the voxel-wise distance values specify distances from corresponding voxels in the plurality of voxels to atoms in corresponding atom categories in the plurality of atom categories;
processing a tensor that includes the atom category-wise distance channels and an alternative allele of the protein expressed by a variant; and
determining a pathogenicity of the variant based at least in part on the tensor.

64. The computer-implemented method of claim 63, further comprising centering a voxel grid of the voxels on respective atoms of respective atom categories in the plurality of atom categories.

65. The computer-implemented method of claim 64, further comprising centering the voxel grid on an alpha carbon atom of a residue of at least one variant amino acid in the protein.

66. The computer-implemented method of claim 65, wherein the distances are nearest-atom distances from corresponding voxel centers in the voxel grid to nearest atoms in the corresponding atom categories.

67. The computer-implemented method of claim 66, wherein the nearest-atom distances are Euclidean distances.

68. The computer-implemented method of claim 67, wherein the nearest-atom distances are normalized by dividing the Euclidean distances with a maximum nearest-atom distances.

69. The computer-implemented method of claim 68, wherein the distances are nearest-atom distances from the corresponding voxel centers in the voxel grid to nearest atoms irrespective of the amino acids and the atom categories of the amino acids.

70. The computer-implemented method of claim 69, wherein the nearest-atom distances are Euclidean distances.

71. The computer-implemented method of claim 70, wherein the nearest-atom distances are normalized by dividing the Euclidean distances with a maximum nearest-atom distances.

1. One or more computer-readable media storing computer-executable instructions that, when executed on one or more processors, configure a computer to perform operations comprising:
storing amino acid-wise distance channels for a plurality of amino acids in a protein,
wherein each of the amino acid-wise distance channels has voxel-wise distance values for voxels in a plurality of voxels, and
wherein the voxel-wise distance values specify distances from corresponding voxels in the plurality of voxels to atoms of corresponding amino acids in the plurality of amino acids;
processing a tensor that includes the amino acid-wise distance channels and an alternative allele of the protein expressed by a variant; and
determining a pathogenicity of the variant based at least in part on the tensor.

2. The computer-readable media of claim 1, the operations further comprising centering a voxel grid of the voxels on an alpha carbon atom of respective residues of the amino acids.

3. The computer-readable media of claim 2, the operations further comprising centering the voxel grid on an alpha carbon atom of a residue of a particular amino acid that corresponds to at least one variant amino acid in the protein.

4. The computer-readable media of claim 3, the operations further comprising encoding, in the tensor, a directionality of the amino acids and a position of the particular amino acid by multiplying, with a directionality parameter, voxel-wise distance values for those amino acids that precede the particular amino acid.

5. The computer-readable media of claim 3, wherein the distances are nearest-atom distances from corresponding voxel centers in the voxel grid to nearest atoms of the corresponding amino acids.

6. The computer-readable media of claim 5, wherein the nearest-atom distances are Euclidean distances.

7. The computer-readable media of claim 6, wherein the nearest-atom distances are normalized by dividing the Euclidean distances with a maximum nearest-atom distance.

8. The computer-readable media of claim 5, wherein the amino acids have alpha carbon atoms, and wherein the distances are nearest-alpha carbon atom distances from the corresponding voxel centers to nearest alpha carbon atoms of the corresponding amino acids.

9. The computer-readable media of claim 5, wherein the amino acids have beta carbon atoms and wherein the distances are nearest-beta carbon atom distances from the corresponding voxel centers to nearest beta carbon atoms of the corresponding amino acids.

10. The computer-readable media of claim 5, wherein the amino acids have backbone atoms and wherein the distances are nearest-backbone atom distances from the corresponding voxel centers to nearest backbone atoms of the corresponding amino acids.

11. The computer-readable media of claim 5, wherein the amino acids have sidechain atom and wherein the distances are nearest-sidechain atom distances from the corresponding voxel centers to nearest sidechain atoms of the corresponding amino acids.

12. The computer-readable media of claim 3, the operations further comprising encoding, in the tensor, a nearest atom channel that specifies a distance from each voxel to a nearest atom, wherein the nearest atom is selected irrespective of the amino acids and atomic elements of the amino acids.

13. The computer-readable media of claim 12, wherein the distance is a Euclidean distance.

14. The computer-readable media of claim 13, wherein the distance is normalized by dividing the Euclidean distance with a maximum distance.

15. The computer-readable media of claim 12, wherein the amino acids include non-standard amino acids.

16. The computer-readable media of claim 1, wherein the tensor further includes an absentee atom channel that specifies atoms not found within a predefined radius of a voxel center, and wherein the absentee atom channel is one-hot encoded.

17. The computer-readable media of claim 1, wherein the tensor further includes a one-hot encoding of the alternative allele that is voxel-wise encoded to each of the amino acid-wise distance channels.

18. The computer-readable media of claim 1, wherein the tensor further includes a reference allele of the protein.

19. The computer-readable media of claim 18, wherein the tensor further includes a one-hot encoding of the reference allele that is voxel-wise encoded to each of the amino acid-wise distance channels.

20. The computer-readable media of claim 1, wherein the tensor further includes evolutionary profiles that specify conservation levels of the amino acids across a plurality of species.

21. The computer-readable media of claim 20, the operations further comprising, for each of the voxels,
   selecting a nearest atom across the amino acids and the atom categories,
   selecting a pan-amino acid conservation frequencies sequence for a residue of an amino acid that includes the nearest atom, and
   making the pan-amino acid conservation frequencies sequence available as one of the evolutionary profiles.

22. The computer-readable media of claim 21, wherein the pan-amino acid conservation frequencies sequence is configured for a particular position of the residue as observed in the plurality of species.

23. The computer-readable media of claim 21, wherein the pan-amino acid conservation frequencies sequence specifies whether there is a missing conservation frequency for a particular amino acid.

24. The computer-readable media of claim 21, the operations further comprising, for each of the voxels,
   selecting respective nearest atoms in respective ones of the amino acids,
   selecting respective per-amino acid conservation frequencies for respective residues of the amino acids that include the nearest atoms, and
   making the per-amino acid conservation frequencies available as one of the evolutionary profiles.

25. The computer-readable media of claim 24, wherein the per-amino acid conservation frequencies are configured for a particular position of the residues as observed in the plurality of species.

26. The computer-readable media of claim 24, wherein the per-amino acid conservation frequencies specify whether there is a missing conservation frequency for a particular amino acid.

27. The computer-readable media of claim 1, wherein the tensor further includes annotation channels for the amino acids, wherein the annotation channels are one-hot encoded in the tensor.

28. The computer-readable media of claim 27, wherein the annotation channels are molecular processing annotations that include initiator methionine, signal, transit peptide, propeptide, chain, and peptide.

29. The computer-readable media of claim 27, wherein the annotation channels are regions annotations that include topological domain, transmembrane, intramembrane, domain, repeat, calcium binding, zinc finger, deoxyribonucleic acid (DNA) binding, nucleotide binding, region, coiled coil, motif, and compositional bias.

30. The computer-readable media of claim 27, wherein the annotation channels are sites annotations that include active site, metal binding, binding site, and site.

31. The computer-readable media of claim 27, wherein the annotation channels are amino acid modifications annotations that include non-standard residue, modified residue, lipidation, glycosylation, disulfide bond, and cross-link.

32. The computer-readable media of claim 27, wherein the annotation channels are secondary structure annotations that include helix, turn, and beta strand.

33. The computer-readable media of claim 27, wherein the annotation channels are experimental information annotations that include mutagenesis, sequence uncertainty, sequence conflict, non-adjacent residues, and non-terminal residue.

34. The computer-readable media of claim 1, wherein the tensor further includes structure confidence channels for the amino acids that specify quality of respective structures of the amino acids.

35. The computer-readable media of claim 34, wherein the structure confidence channels are global model quality estimations (GMQEs).

36. The computer-readable media of claim 34, wherein the structure confidence channels include qualitative model energy analysis (QMEAN) scores.

37. The computer-readable media of claim 34, wherein the structure confidence channels are temperature factors that specify a degree to which the residues satisfy physical constraints of respective protein structures.

38. The computer-readable media of claim 34, wherein the structure confidence channels are template structures alignments that specify a degree to which residues of atoms nearest to the voxels have aligned template structures.

39. The computer-readable media of claim 38, wherein the structure confidence channels are template modeling scores of the aligned template structures.

40. The computer-readable media of claim 39, wherein the structure confidence channels are a minimum one of the template modeling scores, a mean of the template modeling scores, and a maximum one of the template modeling scores.

41. The computer-readable media of claim 1, the operations further comprising voxel-wise concatenating amino acid-wise distance channels for the alpha carbon atoms with the one-hot encoding of the alternative allele to generate the tensor.

42. The computer-readable media of claim 41, the operations further comprising voxel-wise concatenating amino acid-wise distance channels for the beta carbon atoms with the one-hot encoding of the alternative allele to generate the tensor.

43. The computer-readable media of claim 42, the operations further comprising voxel-wise concatenating the amino acid-wise distance channels for the alpha carbon atoms, the amino acid-wise distance channels for the beta carbon atoms, and the one-hot encoding of the alternative allele to generate the tensor.

44. The computer-readable media of claim 43, the operations further comprising voxel-wise concatenating the amino acid-wise distance channels for the alpha carbon atoms, the amino acid-wise distance channels for the beta carbon atoms, the one-hot encoding of the alternative allele, and pan-amino acid conservation frequencies sequences to generate the tensor.

45. The computer-readable media of claim 44, the operations further comprising voxel-wise concatenating the amino acid-wise distance channels for the alpha carbon atoms, the amino acid-wise distance channels for the beta carbon atoms, the one-hot encoding of the alternative allele, the pan-amino acid conservation frequencies sequences, and the annotation channels to generate the tensor.

46. The computer-readable media of claim 45, the operations further comprising voxel-wise concatenating the amino acid-wise distance channels for the alpha carbon atoms, the amino acid-wise distance channels for the beta carbon atoms, the one-hot encoding of the alternative allele, the pan-amino acid conservation frequencies sequences, the annotation channels, and the structure confidence channels to generate the tensor.

47. The computer-readable media of claim 46, the operations further comprising voxel-wise concatenating the amino acid-wise distance channels for the alpha carbon atoms, the amino acid-wise distance channels for the beta carbon atoms, the one-hot encoding of the alternative allele, and per-amino acid conservation frequencies for each of the amino acids to generate the tensor.

48. The computer-readable media of claim 47, the operations further comprising voxel-wise concatenating the amino acid-wise distance channels for the alpha carbon atoms, the amino acid-wise distance channels for the beta carbon atoms, the one-hot encoding of the alternative allele, per-amino acid conservation frequencies for each of the amino acids, and the annotation channels to generate the tensor.

49. The computer-readable media of claim 48, the operations further comprising voxel-wise concatenating the amino acid-wise distance channels for the alpha carbon atoms, the amino acid-wise distance channels for the beta carbon atoms, the one-hot encoding of the alternative allele, per-amino acid conservation frequencies for each of the amino acids, the annotation channels, and the structure confidence channels to generate the tensor.

50. The computer-readable media of claim 49, the operations further comprising voxel-wise concatenating the amino acid-wise distance channels for the alpha carbon atoms, the amino acid-wise distance channels for the beta carbon atoms, the one-hot encoding of the alternative allele, and the one-hot encoding of the reference allele to generate the tensor.

51. The computer-readable media of claim 50, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, and the pan-amino acid conservation frequencies sequences to generate the tensor.

52. The computer-readable media of claim 51, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the pan-amino acid conservation frequencies sequences, and the annotation channels to generate the tensor.

53. The computer-readable media of claim 52, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the pan-amino acid conservation frequencies sequences, the annotation channels, and the structure confidence channels to generate the tensor.

54. The computer-readable media of claim 53, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, and the per-amino acid conservation frequencies for each of the amino acids to generate the tensor.

55. The computer-readable media of claim 54, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the per-amino acid conservation frequencies for each of the amino acids, and the annotation channels to generate the tensor.

56. The computer-readable media of claim 55, the operations further comprising voxel-wise concatenating the amino acid-wise distance channels for the alpha carbon atoms, the amino acid-wise distance channels for the beta carbon atoms, the one-hot encoding of the alternative allele, the one-hot encoding of the reference allele, the per-amino acid conservation frequencies for each of the amino acids, the annotation channels, and the structure confidence channels to generate the tensor.

57. The computer-readable media of claim 1, the operations further comprising rotating atoms of the amino acids before the amino acid-wise distance channels are generated.

58. The computer-readable media of claim 1, the operations further comprising using 1×1×1 convolutions, 3×3×3 convolutions, rectified linear unit activation layers, batch normalization layers, a fully-connected layer, a dropout regularization layer, and a softmax classification layer in a convolutional neural network.

59. The computer-readable media of claim 58, wherein the 1×1×1 convolutions and the 3×3×3 convolutions are three-dimensional convolutions.

60. The computer-readable media of claim 58, wherein a layer of the 1×1×1 convolutions processes the tensor and produces an intermediate output that is a convolved representation of the tensor, wherein a sequence of layers of the 3×3×3 convolutions processes the intermediate output and produces a flattened output, wherein the fully-connected layer processes the flattened output and produces unnormalized outputs, and wherein the softmax classification layer processes the unnormalized outputs and produces exponentially normalized outputs that identify likelihoods of the variant being pathogenic and benign.

61. The computer-readable media of claim 60, wherein a sigmoid layer processes the unnormalized outputs and produces a normalized output that identifies a likelihood of the variant being pathogenic.

62. The computer-readable media of claim 60, wherein the voxels, the atoms, and the distances have three-dimensional coordinates, wherein the tensor has at least three dimensions, wherein the intermediate output has at least three dimensions, and wherein the flattened output has one dimension.

63. One or more computer-readable media storing computer-executable instructions that, when executed on one or more processors, configure a computer to perform operations comprising:

storing atom category-wise distance channels for amino acids in a protein,
        wherein the amino acids have atoms for a plurality of atom categories,
        wherein atom categories in the plurality of atom categories specify atomic elements of the amino acids,
        wherein each of the atom category-wise distance channels has voxel-wise distance values for voxels in a plurality of voxels, and
        wherein the voxel-wise distance values specify distances from corresponding voxels in the plurality of voxels to atoms in corresponding atom categories in the plurality of atom categories;
    processing a tensor that includes the atom category-wise distance channels and an alternative allele of the protein expressed by a variant; and
    determining a pathogenicity of the variant based at least in part on the tensor.

64. The computer-readable media of claim 63, the operations further comprising centering a voxel grid of the voxels on respective atoms of respective atom categories in the plurality of atom categories.

65. The computer-readable media of claim 64, the operations further comprising centering the voxel grid on an alpha carbon atom of a residue of at least one variant amino acid in the protein.

66. The computer-readable media of claim 65, wherein the distances are nearest-atom distances from corresponding voxel centers in the voxel grid to nearest atoms in the corresponding atom categories.

67. The computer-readable media of claim 66, wherein the nearest-atom distances are Euclidean distances.

68. The computer-readable media of claim 67, wherein the nearest-atom distances are normalized by dividing the Euclidean distances with a maximum nearest-atom distances.

69. The computer-readable media of claim 68, wherein the distances are nearest-atom distances from the corresponding voxel centers in the voxel grid to nearest atoms irrespective of the amino acids and the atom categories of the amino acids.

70. The computer-readable media of claim 69, wherein the nearest-atom distances are Euclidean distances.

71. The computer-readable media of claim 70, wherein the nearest-atom distances are normalized by dividing the Euclidean distances with a maximum nearest-atom distances.

Particular Implementations 2

In some implementations, a system comprises a voxelizer that accesses a three-dimensional structure of a reference amino acid sequence of a protein and fits a three-dimensional grid of voxels on atoms in the three-dimensional structure on an amino acid-basis to generate amino acid-wise distance channels. Each of the amino acid-wise distance channels has a three-dimensional distance value for each voxel in the three-dimensional grid of voxels. The three-dimensional distance value specifies a distance from a corresponding voxel in the three-dimensional grid of voxels to atoms of a corresponding reference amino acid in the reference amino acid sequence. The system further comprises an alternative allele encoder that encodes an alternative allele amino acid to each voxel in the three-dimensional grid of voxels. The alternative allele amino acid is a three-dimensional representation of a one-hot encoding of a variant amino acid expressed by a variant nucleotide. The system further comprises an evolutionary conservation encoder that encodes an evolutionary conservation sequence to each voxel in the three-dimensional grid of voxels. The evolutionary conservation sequence can be a three-dimensional representation of amino acid-specific conservation frequencies across a plurality of species. The amino acid-specific conservation frequencies can be selected in dependence upon amino acid proximity to the corresponding voxel. The system further comprises a convolutional neural network configured to apply three-dimensional convolutions to a tensor that includes the amino acid-wise distance channels encoded with the alternative allele amino acid and respective evolutionary conservation sequences. The convolutional neural network can be also configured to determine a pathogenicity of the variant nucleotide based at least in part on the tensor.

The voxelizer can center the three-dimensional grid of voxels on an alpha-carbon atom of respective residues of reference amino acids in the reference amino acid sequence. The voxelizer can center the three-dimensional grid of voxels on an alpha-carbon atom of a residue of a particular reference amino acid positioned at the variant amino acid.

In some implementations, the system can be further configured to encode, in the tensor, a directionality of the reference amino acids in the reference amino acid sequence and a position of the particular reference amino acid by multiplying, with a directionality parameter, three-dimensional distance values for those reference amino acids that precede the particular reference amino acid. The distances can be nearest-atom distances from corresponding voxel centers in the three-dimensional grid of voxels to nearest atoms of the corresponding reference amino acids. The nearest-atom distances can be Euclidean distances and can be normalized by dividing the Euclidean distances with a maximum nearest-atom distance.

In some implementations, the reference amino acids can have alpha-carbon atoms and the distances can be nearest-alpha-carbon atom distances from the corresponding voxel centers to nearest alpha-carbon atoms of the corresponding reference amino acids. In some implementations, the reference amino acids can have beta-carbon atoms and the distances can be nearest-beta-carbon atom distances from the corresponding voxel centers to nearest beta-carbon atoms of the corresponding reference amino acids. In some implementations, the reference amino acids can have backbone atoms and the distances can be nearest-backbone atom distances from the corresponding voxel centers to nearest backbone atoms of the corresponding reference amino acids. In some implementations, the amino acids can have sidechain atoms and the distances can be nearest-sidechain atom distances from the corresponding voxel centers to nearest sidechain atoms of the corresponding reference amino acids.

In some implementations, the system can be further configured to encode, in the tensor, a nearest atom channel that specifies a distance from each voxel to a nearest atom. The nearest atom can be selected irrespective of the amino acids and atomic elements of the amino acids. The distance can be a Euclidean distance and can be normalized by dividing the Euclidean distance with a maximum distance. The amino acids can include non-standard amino acids. The tensor can further include an absentee atom channel that specifies atoms not found within a predefined radius of a voxel center. The absentee atom channel can be one-hot encoded.

In some implementations, the system can further comprise a reference allele encoder that voxel-wise encodes a reference allele amino acid to each three-dimensional distance value on the amino acid position-basis. The reference allele amino acid can be a three-dimensional representation of a one-hot encoding of the reference amino acid sequence. The amino acid-specific conservation frequencies can specify conservation levels of respective amino acids across the plurality of species.

In some implementations, the evolutionary conservation encoder can select a nearest atom to the corresponding voxel across the reference amino acids and the atom categories, can select pan-amino acid conservation frequencies for a residue of a reference amino acid that includes the nearest atom, and can use a three-dimensional representation of the pan-amino acid conservation frequencies as the evolutionary conservation sequence. The pan-amino acid conservation frequencies can be configured for a particular position of the residue as observed in the plurality of species. The pan-amino acid conservation frequencies can specify whether there is a missing conservation frequency for a particular reference amino acid.

In some implementations, the evolutionary conservation encoder can select respective nearest atoms to the corresponding voxel in respective ones of the reference amino acids, can select respective per-amino acid conservation frequencies for respective residues of the reference amino acids that include the nearest atoms, and can use a three-dimensional representation of the per-amino acid conservation frequencies as the evolutionary conservation sequence. The per-amino acid conservation frequencies can be configured for a particular position of the residues as observed in the plurality of species. The per-amino acid conservation frequencies can specify whether there is a missing conservation frequency for a particular reference amino acid.

In some implementations, the system can further comprise an annotations encoder that voxel-wise encodes one or more annotation channels to each three-dimensional distance value. The annotation channels can be three-dimensional representations of a one-hot encoding of residue annotations and can be molecular processing annotations that include initiator methionine, signal, transit peptide, propeptide, chain, and peptide. In some implementations, the annotation channels can be regions annotations that include topological domain, transmembrane, intramembrane, domain, repeat, calcium binding, zinc finger, deoxyribonucleic acid (DNA) binding, nucleotide binding, region, coiled coil, motif, and compositional bias or can be sites annotations that include active site, metal binding, binding site, and site. In some implementations, the annotation channels can be amino acid modifications annotations that include non-standard residue, modified residue, lipidation, glycosylation, disulfide bond, and cross-link or can be secondary structure annotations that include helix, turn, and beta strand. The annotation channels can be experimental information annotations that include mutagenesis, sequence uncertainty, sequence conflict, non-adjacent residues, and non-terminal residue.

In some implementations, the system can further comprise a structure confidence encoder that voxel-wise encodes one or more structure confidence channels to each three-dimensional distance value. The structure confidence channels can be three-dimensional representations of confidence scores that specify quality of respective residue structures. The structure confidence channels can be global model quality estimations (GMQEs), can be qualitative model energy analysis (QMEAN) scores, can be temperature factors that specify a degree to which the residues satisfy physical constraints of respective protein structures, can be template structures alignments that specify a degree to which residues of atoms nearest to the voxels have aligned template structures, can be template modeling scores of the aligned template structures, or can be a minimum one of the template modeling scores, a mean of the template modeling scores, and a maximum one of the template modeling scores.

In some implementations, the system can further comprise an atoms rotation engine that rotates the atoms before the amino acid-wise distance channels are generated.

The convolutional neural network can use 1×1×1 convolutions, 3×3×3 convolutions, rectified linear unit activation layers, batch normalization layers, a fully-connected layer, a dropout regularization layer, and a softmax classification layer. The 1×1×1 convolutions and the 3×3×3 convolutions can be the three-dimensional convolutions. In some implementations, a layer of the 1×1×1 convolutions can process the tensor and produce an intermediate output that is a convolved representation of the tensor. A sequence of layers of the 3×3×3 convolutions can process the intermediate output and produce a flattened output. The fully-connected layer can process the flattened output and produce unnormalized outputs. The softmax classification layer can process the unnormalized outputs and produce exponentially normalized outputs that identify likelihoods of the variant nucleotide being pathogenic and benign.

In some implementations, a sigmoid layer can process the unnormalized outputs and produce a normalized output that identifies a likelihood of the variant nucleotide being pathogenic. The convolutional neural network can be an attention-based neural network. The tensor can include the amino acid-wise distance channels further encoded with the reference allele amino acid, can include the amino acid-wise distance channels further encoded with the annotation channels, or can include the amino acid-wise distance channels further encoded with the structure confidence channels.

In some implementations, a system can comprise a voxelizer that accesses a three-dimensional structure of a reference amino acid sequence of a protein and fits a three-dimensional grid of voxels on atoms in the three-dimensional structure on an amino acid-basis to generate atom category-wise distance channels. The atoms span a plurality of atom categories, which specify atomic elements of the amino acids. Each of the atom category-wise distance channels has a three-dimensional distance value for each voxel in the three-dimensional grid of voxels. The three-dimensional distance value specifies a distance from a corresponding voxel in the three-dimensional grid of voxels to atoms of corresponding atom categories in the plurality of atom categories. The system further comprises an alternative allele encoder that encodes an alternative allele amino acid to each voxel in the three-dimensional grid of voxels. The alternative allele amino acid is a three-dimensional representation of a one-hot encoding of a variant amino acid expressed by a variant nucleotide. The system further comprises an evolutionary conservation encoder that encodes an evolutionary conservation sequence to each voxel in the three-dimensional grid of voxels. The evolutionary conservation sequence can be a three-dimensional representation of amino acid-specific conservation frequencies across a plurality of species. The amino acid-specific conservation frequencies can be selected in dependence upon amino acid proximity to the corresponding voxel. The system further comprises a convolutional neural network configured to apply three-dimensional convolutions to a tensor that includes the atom category-wise distance channels encoded with the alternative allele amino acid and respective evolutionary conservation sequences, and to determine a pathogenicity of the variant nucleotide based at least in part on the tensor.

In some implementations, a system comprises a voxelizer that accesses a three-dimensional structure of a reference amino acid sequence of a protein and fits a three-dimensional grid of voxels on atoms in the three-dimensional structure on an amino acid-basis to generate amino acid-wise distance channels. Each of the amino acid-wise distance channels can have a three-dimensional distance value for each voxel in the three-dimensional grid of voxels. The three-dimensional distance value can specify a distance from a corresponding voxel in the three-dimensional grid of voxels to atoms of a corresponding reference amino acid in the reference amino acid sequence. The system further comprises an alternative allele encoder that encodes an alternative allele amino acid to each voxel in the three-dimensional grid of voxels. The alternative allele amino acid is a three-dimensional representation of a one-hot encoding of a variant amino acid expressed by a variant nucleotide. The system further comprises an evolutionary conservation encoder that encodes an evolutionary conservation sequence to each voxel in the three-dimensional grid of voxels. The evolutionary conservation sequence can be a three-dimensional representation of amino acid-specific conservation frequencies across a plurality of species. The amino acid-specific conservation frequencies can be selected in dependence upon amino acid proximity to the corresponding voxel. The system further comprises a tensor generator configured to generate a tensor that includes the amino acid-wise distance channels encoded with the alternative allele amino acid and respective evolutionary conservation sequences.

In some implementations, a system comprises a voxelizer that accesses a three-dimensional structure of a reference amino acid sequence of a protein and fits a three-dimensional grid of voxels on atoms in the three-dimensional structure on an amino acid-basis to generate atom category-wise distance channels. The atoms can span a plurality of atom categories, which specify atomic elements of the amino acids. Each of the atom category-wise distance channels can have a three-dimensional distance value for each voxel in the three-dimensional grid of voxels. The three-dimensional distance value can specify a distance from a corresponding voxel in the three-dimensional grid of voxels to atoms of corresponding atom categories in the plurality of atom categories. The system further comprises an alternative allele encoder that encodes an alternative allele amino acid to each voxel in the three-dimensional grid of voxels. The alternative allele amino acid is a three-dimensional representation of a one-hot encoding of a variant amino acid expressed by a variant nucleotide. The system further comprises an evolutionary conservation encoder that encodes an evolutionary conservation sequence to each voxel in the three-dimensional grid of voxels. The evolutionary conservation sequence can be a three-dimensional representation of amino acid-specific conservation frequencies across a plurality of species. The amino acid-specific conservation frequencies can be selected in dependence upon amino acid proximity to the corresponding voxel. The system further comprises a tensor generator configured to generate a tensor that includes the atom category-wise distance channels encoded with the alternative allele amino acid and respective evolutionary conservation sequences.

1. A computer-implemented method, comprising:
   accessing a three-dimensional structure of a reference amino acid sequence of a protein, and fitting a three-dimensional grid of voxels on atoms in the three-dimensional structure on an amino acid-basis to generate amino acid-wise distance channels,
      wherein each of the amino acid-wise distance channels has a three-dimensional distance value for each voxel in the three-dimensional grid of voxels, and
      wherein the three-dimensional distance value specifies a distance from a corresponding voxel in the three-dimensional grid of voxels to atoms of a corresponding reference amino acid in the reference amino acid sequence;
   encoding an alternative allele channel to each voxel in the three-dimensional grid of voxels,
      wherein the alternative allele channel is a three-dimensional representation of a one-hot encoding of a variant amino acid expressed by a variant nucleotide;
   encoding an evolutionary conservation channel to each sequence of three-dimensional distance values across the amino acid-wise distance channels on a voxel position-basis,
      wherein the evolutionary conservation channel is a three-dimensional representation of amino acid-specific conservation frequencies across a plurality of species, and
      wherein the amino acid-specific conservation frequencies are selected in dependence upon amino acid proximity to the corresponding voxel;
   applying three-dimensional convolutions to a tensor that includes the amino acid-wise distance channels encoded with the alternative allele channel and respective evolutionary conservation channels; and
   determining a pathogenicity of the variant nucleotide based at least in part on the tensor.

2. The computer-implemented method of clause 1, further comprising centering the three-dimensional grid of voxels on an alpha carbon atom of respective residues of reference amino acids in the reference amino acid sequence.

3. The computer-implemented method of clause 2, further comprising centering the three-dimensional grid of voxels on an alpha carbon atom of a residue of a particular reference amino acid that corresponds to the variant amino acid.

4. The computer-implemented method of clause 3, further comprising encoding, in the tensor, a directionality of the reference amino acids in the reference amino acid sequence and a position of the particular reference amino acid by multiplying, with a directionality parameter, three-dimensional distance values for those reference amino acids that precede the particular reference amino acid.

5. The computer-implemented method of clause 4, wherein the distances are nearest-atom distances from corresponding voxel centers in the three-dimensional grid of voxels to nearest atoms of the corresponding reference amino acids.

6. The computer-implemented method of clause 5, wherein the nearest-atom distances are Euclidean distances.

7. The computer-implemented method of clause 6, wherein the nearest-atom distances are normalized by dividing the Euclidean distances with a maximum nearest-atom distance.

8. The computer-implemented method of clause 5, wherein the reference amino acids have alpha carbon atoms and wherein the distances are nearest-alpha carbon atom distances from the corresponding voxel centers to nearest alpha carbon atoms of the corresponding reference amino acids.

9. The computer-implemented method of clause 5, wherein the reference amino acids have beta carbon atoms and wherein the distances are nearest-beta carbon atom distances from the corresponding voxel centers to nearest beta carbon atoms of the corresponding reference amino acids.

10. The computer-implemented method of clause 5, wherein the reference amino acids have backbone atoms and wherein the distances are nearest-backbone atom distances from the corresponding voxel centers to nearest backbone atoms of the corresponding reference amino acids.

11. The computer-implemented method of clause 5, wherein the amino acids have sidechain atoms and wherein the distances are nearest-sidechain atom distances from the corresponding voxel centers to nearest sidechain atoms of the corresponding reference amino acids.

12. The computer-implemented method of clause 3, further comprising encoding, in the tensor, a nearest atom channel that specifies a distance from each voxel to a nearest atom, wherein the nearest atom is selected irrespective of the amino acids and atomic elements of the amino acids.

13. The computer-implemented method of clause 12, wherein the distance is a Euclidean distance.

14. The computer-implemented method of clause 13, wherein the distance is normalized by dividing the Euclidean distance with a maximum distance.

15. The computer-implemented method of clause 12, wherein the amino acids include non-standard amino acids.

16. The computer-implemented method of clause 1, wherein the tensor further includes an absentee atom channel that specifies atoms not found within a predefined radius of a voxel center.

17. The computer-implemented method of clause 16, wherein the absentee atom channel is one-hot encoded.

18. The computer-implemented method of clause 1, further comprising voxel-wise encoding a reference allele channel to each voxel in the three-dimensional grid of voxels.

19. The computer-implemented method of clause 18, the reference allele amino acid is a three-dimensional representation of a one-hot encoding of a reference amino acid that experiences the variant amino acid.

20. The computer-implemented method of clause 1, wherein the amino acid-specific conservation frequencies specify conservation levels of respective amino acids across the plurality of species.

21. The computer-implemented method of clause 20, further comprising:
    selecting a nearest atom to the corresponding voxel across the reference amino acids and the atom categories,
    selecting pan-amino acid conservation frequencies for a residue of a reference amino acid that includes the nearest atom, and
    using a three-dimensional representation of the pan-amino acid conservation frequencies as the evolutionary conservation channel.

22. The computer-implemented method of clause 21, wherein the pan-amino acid conservation frequencies are configured for a particular position of the residue as observed in the plurality of species.

23. The computer-implemented method of clause 21, wherein the pan-amino acid conservation frequencies specify whether there is a missing conservation frequency for a particular reference amino acid.

24. The computer-implemented method of clause 21, further comprising:
    selecting respective nearest atoms to the corresponding voxel in respective ones of the reference amino acids,
    selecting respective per-amino acid conservation frequencies for respective residues of the reference amino acids that include the nearest atoms, and
    using a three-dimensional representation of the per-amino acid conservation frequencies as the evolutionary conservation channel.

25. The computer-implemented method of clause 24, wherein the per-amino acid conservation frequencies are configured for a particular position of the residues as observed in the plurality of species.

26. The computer-implemented method of clause 24, wherein the per-amino acid conservation frequencies specify whether there is a missing conservation frequency for a particular reference amino acid.

27. The computer-implemented method of clause 1, further comprising voxel-wise encoding one or more annotation channels to each voxel in the three-dimensional grid of voxels, wherein the annotation channels are three-dimensional representations of a one-hot encoding of residue annotations.

28. The computer-implemented method of clause 27, wherein the annotation channels are molecular processing annotations that include initiator methionine, signal, transit peptide, propeptide, chain, and peptide.

29. The computer-implemented method of clause 27, wherein the annotation channels are regions annotations that include topological domain, transmembrane, intramembrane, domain, repeat, calcium binding, zinc finger, deoxyribonucleic acid (DNA) binding, nucleotide binding, region, coiled coil, motif, and compositional bias.

30. The computer-implemented method of clause 27, wherein the annotation channels are sites annotations that include active site, metal binding, binding site, and site.

31. The computer-implemented method of clause 27, wherein the annotation channels are amino acid modifications annotations that include non-standard residue, modified residue, lipidation, glycosylation, disulfide bond, and cross-link.

32. The computer-implemented method of clause 27, wherein the annotation channels are secondary structure annotations that include helix, turn, and beta strand.

33. The computer-implemented method of clause 27, wherein the annotation channels are experimental information annotations that include mutagenesis, sequence uncertainty, sequence conflict, non-adjacent residues, and non-terminal residue.

34. The computer-implemented method of clause 1, further comprising voxel-wise encoding one or more structure confidence channels to each voxel in the three-dimensional grid of voxels, wherein the structure confidence channels are three-dimensional representations of confidence scores that specify quality of respective residue structures.

35. The computer-implemented method of clause 34, wherein the structure confidence channels are global model quality estimations (GMQEs).

36. The computer-implemented method of clause 34, wherein the structure confidence channels are qualitative model energy analysis (QMEAN) scores.

37. The computer-implemented method of clause 34, wherein the structure confidence channels are temperature factors that specify a degree to which the residues satisfy physical constraints of respective protein structures.

38. The computer-implemented method of clause 34, wherein the structure confidence channels are template structures alignments that specify a degree to which residues of atoms nearest to the voxels have aligned template structures.

39. The computer-implemented method of clause 38, wherein the structure confidence channels are template modeling scores of the aligned template structures.

40. The computer-implemented method of clause 39, wherein the structure confidence channels are a minimum one of the template modeling scores, a mean of the template modeling scores, and a maximum one of the template modeling scores.

41. The computer-implemented method of clause 1, further comprising rotating the atoms before the amino acid-wise distance channels are generated.

42. The computer-implemented method of clause 1, further comprising using 1×1×1 convolutions, 3×3×3 convolutions, rectified linear unit activation layers, batch normalization layers, a fully-connected layer, a dropout regularization layer, and a softmax classification layer in a convolutional neural network.

43. The computer-implemented method of clause 42, wherein the 1×1×1 convolutions and the 3×3×3 convolutions are the three-dimensional convolutions.

44. The computer-implemented method of clause 42, wherein a layer of the 1×1×1 convolutions processes the tensor and produces an intermediate output that is a convolved representation of the tensor, wherein a sequence of layers of the 3×3×3 convolutions processes the intermediate output and produces a flattened output, wherein the fully-connected layer processes the flattened output and produces unnormalized outputs, and wherein the softmax classification layer processes the unnormalized outputs and produces exponentially normalized outputs that identify likelihoods of the variant nucleotide being pathogenic and benign.

45. The computer-implemented method of clause 44, wherein a sigmoid layer processes the unnormalized outputs and produces a normalized output that identifies a likelihood of the variant nucleotide being pathogenic.

46. The computer-implemented method of clause 1, wherein the convolutional neural network is an attention-based neural network.

47. The computer-implemented method of clause 1, wherein the tensor includes the amino acid-wise distance channels further encoded with the reference allele channel.

48. The computer-implemented method of clause 1, wherein the tensor includes the amino acid-wise distance channels further encoded with the annotation channels.

49. The computer-implemented method of clause 1, wherein the tensor includes the amino acid-wise distance channels further encoded with the structure confidence channels.

50. A computer-implemented method, comprising:
   accessing a three-dimensional structure of a reference amino acid sequence of a protein, and fitting a three-dimensional grid of voxels on atoms in the three-dimensional structure on an amino acid-basis to generate atom category-wise distance channels,
      wherein the atoms span a plurality of atom categories,
      wherein atom categories in the plurality of atom categories specify atomic elements of the amino acids,
      wherein each of the atom category-wise distance channels has a three-dimensional distance value for each voxel in the three-dimensional grid of voxels, and
      wherein the three-dimensional distance value specifies a distance from a corresponding voxel in the three-dimensional grid of voxels to atoms of corresponding atom categories in the plurality of atom categories;
   encoding an alternative allele channel to each voxel in the three-dimensional grid of voxels,
      wherein the alternative allele channel is a three-dimensional representation of a one-hot encoding of a variant amino acid expressed by a variant nucleotide;
   encoding an evolutionary conservation channel to each sequence of three-dimensional distance values across the atom category-wise distance channels on a voxel position-basis,
      wherein the evolutionary conservation channel is a three-dimensional representation of amino acid-specific conservation frequencies across a plurality of species, and
      wherein the amino acid-specific conservation frequencies are selected in dependence upon amino acid proximity to the corresponding voxel;
   applying three-dimensional convolutions to a tensor that includes the atom category-wise distance channels encoded with the alternative allele channel and respective evolutionary conservation channels; and
   determining a pathogenicity of the variant nucleotide based at least in part on the tensor.

51. A computer-implemented method, comprising:
   accessing a three-dimensional structure of a reference amino acid sequence of a protein, and fitting a three-dimensional grid of voxels on atoms in the three-dimensional structure on an amino acid-basis to generate amino acid-wise distance channels,
      wherein each of the amino acid-wise distance channels has a three-dimensional distance value for each voxel in the three-dimensional grid of voxels, and
      wherein the three-dimensional distance value specifies a distance from a corresponding voxel in the three-dimensional grid of voxels to atoms of a corresponding reference amino acid in the reference amino acid sequence;
   encoding an alternative allele channel to each voxel in the three-dimensional grid of voxels,
      wherein the alternative allele channel is a three-dimensional representation of a one-hot encoding of a variant amino acid expressed by a variant nucleotide;
   encoding an evolutionary conservation channel to each sequence of three-dimensional distance values across the amino acid-wise distance channels on a voxel position-basis,
      wherein the evolutionary conservation channel is a three-dimensional representation of amino acid-specific conservation frequencies across a plurality of species, and
      wherein the amino acid-specific conservation frequencies are selected in dependence upon amino acid proximity to the corresponding voxel; and
   generating a tensor that includes the amino acid-wise distance channels encoded with the alternative allele channel and respective evolutionary conservation channels.

52. A computer-implemented method, comprising:
   accessing a three-dimensional structure of a reference amino acid sequence of a protein, and fitting a three-dimensional grid of voxels on atoms in the three-dimensional structure on an amino acid-basis to generate atom category-wise distance channels,
      wherein the atoms span a plurality of atom categories,
      wherein atom categories in the plurality of atom categories specify atomic elements of the amino acids, wherein each of the atom category-wise distance channels has a three-dimensional distance value for each voxel in the three-dimensional grid of voxels, and wherein the three-dimensional distance value specifies a distance from a corresponding voxel in the three-dimensional grid of voxels to atoms of corresponding atom categories in the plurality of atom categories;

encoding an alternative allele channel to each voxel in the three-dimensional grid of voxels, wherein the alternative allele channel is a three-dimensional representation of a one-hot encoding of a variant amino acid expressed by a variant nucleotide;

encoding an evolutionary conservation channel to each sequence of three-dimensional distance values across the atom category-wise distance channels on a voxel position-basis, wherein the evolutionary conservation channel is a three-dimensional representation of amino acid-specific conservation frequencies across a plurality of species, and wherein the amino acid-specific conservation frequencies are selected in dependence upon amino acid proximity to the corresponding voxel; and generating a tensor that includes the atom category-wise distance channels encoded with the alternative allele channel and respective evolutionary conservation channels.

1. One or more computer-readable media storing computer-executable instructions that, when executed on one or more processors, configure a computer to perform operations comprising:

accessing a three-dimensional structure of a reference amino acid sequence of a protein, and fitting a three-dimensional grid of voxels on atoms in the three-dimensional structure on an amino acid-basis to generate amino acid-wise distance channels, wherein each of the amino acid-wise distance channels has a three-dimensional distance value for each voxel in the three-dimensional grid of voxels, and wherein the three-dimensional distance value specifies a distance from a corresponding voxel in the three-dimensional grid of voxels to atoms of a corresponding reference amino acid in the reference amino acid sequence;

encoding an alternative allele channel to each voxel in the three-dimensional grid of voxels, wherein the alternative allele channel is a three-dimensional representation of a one-hot encoding of a variant amino acid expressed by a variant nucleotide;

encoding an evolutionary conservation channel to each sequence of three-dimensional distance values across the amino acid-wise distance channels on a voxel position-basis, wherein the evolutionary conservation channel is a three-dimensional representation of amino acid-specific conservation frequencies across a plurality of species, and wherein the amino acid-specific conservation frequencies are selected in dependence upon amino acid proximity to the corresponding voxel;

applying three-dimensional convolutions to a tensor that includes the amino acid-wise distance channels encoded with the alternative allele channel and respective evolutionary conservation channels; and determining a pathogenicity of the variant nucleotide based at least in part on the tensor.

2. The computer-readable media of clause 1, the operations further comprising centering the three-dimensional grid of voxels on an alpha carbon atom of respective residues of reference amino acids in the reference amino acid sequence.

3. The computer-readable media of clause 2, the operations further comprising centering the three-dimensional grid of voxels on an alpha carbon atom of a residue of a particular reference amino acid that corresponds to the variant amino acid.

4. The computer-readable media of clause 3, the operations further comprising encoding, in the tensor, a directionality of the reference amino acids in the reference amino acid sequence and a position of the particular reference amino acid by multiplying, with a directionality parameter, three-dimensional distance values for those reference amino acids that precede the particular reference amino acid.

5. The computer-readable media of clause 4, wherein the distances are nearest-atom distances from corresponding voxel centers in the three-dimensional grid of voxels to nearest atoms of the corresponding reference amino acids.

6. The computer-readable media of clause 5, wherein the nearest-atom distances are Euclidean distances.

7. The computer-readable media of clause 6, wherein the nearest-atom distances are normalized by dividing the Euclidean distances with a maximum nearest-atom distance.

8. The computer-readable media of clause 5, wherein the reference amino acids have alpha carbon atoms and wherein the distances are nearest-alpha carbon atom distances from the corresponding voxel centers to nearest alpha carbon atoms of the corresponding reference amino acids.

9. The computer-readable media of clause 5, wherein the reference amino acids have beta carbon atoms and wherein the distances are nearest-beta carbon atom distances from the corresponding voxel centers to nearest beta carbon atoms of the corresponding reference amino acids.

10. The computer-readable media of clause 5, wherein the reference amino acids have backbone atoms and wherein the distances are nearest-backbone atom distances from the corresponding voxel centers to nearest backbone atoms of the corresponding reference amino acids.

11. The computer-readable media of clause 5, wherein the amino acids have sidechain atoms and wherein the distances are nearest-sidechain atom distances from the corresponding voxel centers to nearest sidechain atoms of the corresponding reference amino acids.

12. The computer-readable media of clause 3, the operations further comprising encoding, in the tensor, a nearest atom channel that specifies a distance from each voxel to a nearest atom, wherein the nearest atom is selected irrespective of the amino acids and atomic elements of the amino acids.

13. The computer-readable media of clause 12, wherein the distance is a Euclidean distance.

14. The computer-readable media of clause 13, wherein the distance is normalized by dividing the Euclidean distance with a maximum distance.

15. The computer-readable media of clause 12, wherein the amino acids include non-standard amino acids.

16. The computer-readable media of clause 1, wherein the tensor further includes an absentee atom channel that specifies atoms not found within a predefined radius of a voxel center.

17. The computer-readable media of clause 16, wherein the absentee atom channel is one-hot encoded.

18. The computer-readable media of clause 1, the operations further comprising voxel-wise encoding a reference allele channel to each voxel in the three-dimensional grid of voxels.

19. The computer-readable media of clause 18, the reference allele amino acid is a three-dimensional representation of a one-hot encoding of a reference amino acid that experiences the variant amino acid.

20. The computer-readable media of clause 1, wherein the amino acid-specific conservation frequencies specify conservation levels of respective amino acids across the plurality of species.

21. The computer-readable media of clause 20, the operations further comprising:
  selecting a nearest atom to the corresponding voxel across the reference amino acids and the atom categories,
  selecting pan-amino acid conservation frequencies for a residue of a reference amino acid that includes the nearest atom, and
  using a three-dimensional representation of the pan-amino acid conservation frequencies as the evolutionary conservation channel.

22. The computer-readable media of clause 21, wherein the pan-amino acid conservation frequencies are configured for a particular position of the residue as observed in the plurality of species.

23. The computer-readable media of clause 21, wherein the pan-amino acid conservation frequencies specify whether there is a missing conservation frequency for a particular reference amino acid.

24. The computer-readable media of clause 21, the operations further comprising:
  selecting respective nearest atoms to the corresponding voxel in respective ones of the reference amino acids,
  selecting respective per-amino acid conservation frequencies for respective residues of the reference amino acids that include the nearest atoms, and
  using a three-dimensional representation of the per-amino acid conservation frequencies as the evolutionary conservation channel.

25. The computer-readable media of clause 24, wherein the per-amino acid conservation frequencies are configured for a particular position of the residues as observed in the plurality of species.

26. The computer-readable media of clause 24, wherein the per-amino acid conservation frequencies specify whether there is a missing conservation frequency for a particular reference amino acid.

27. The computer-readable media of clause 1, the operations further comprising voxel-wise encoding one or more annotation channels to each voxel in the three-dimensional grid of voxels, wherein the annotation channels are three-dimensional representations of a one-hot encoding of residue annotations.

28. The computer-readable media of clause 27, wherein the annotation channels are molecular processing annotations that include initiator methionine, signal, transit peptide, propeptide, chain, and peptide.

29. The computer-readable media of clause 27, wherein the annotation channels are regions annotations that include topological domain, transmembrane, intramembrane, domain, repeat, calcium binding, zinc finger, deoxyribonucleic acid (DNA) binding, nucleotide binding, region, coiled coil, motif, and compositional bias.

30. The computer-readable media of clause 27, wherein the annotation channels are sites annotations that include active site, metal binding, binding site, and site.

31. The computer-readable media of clause 27, wherein the annotation channels are amino acid modifications annotations that include non-standard residue, modified residue, lipidation, glycosylation, disulfide bond, and cross-link.

32. The computer-readable media of clause 27, wherein the annotation channels are secondary structure annotations that include helix, turn, and beta strand.

33. The computer-readable media of clause 27, wherein the annotation channels are experimental information annotations that include mutagenesis, sequence uncertainty, sequence conflict, non-adjacent residues, and non-terminal residue.

34. The computer-readable media of clause 1, the operations further comprising voxel-wise encoding one or more structure confidence channels to each voxel in the three-dimensional grid of voxels, wherein the structure confidence channels are three-dimensional representations of confidence scores that specify quality of respective residue structures.

35. The computer-readable media of clause 34, wherein the structure confidence channels are global model quality estimations (GMQEs).

36. The computer-readable media of clause 34, wherein the structure confidence channels are qualitative model energy analysis (QMEAN) scores.

37. The computer-readable media of clause 34, wherein the structure confidence channels are temperature factors that specify a degree to which the residues satisfy physical constraints of respective protein structures.

38. The computer-readable media of clause 34, wherein the structure confidence channels are template structures alignments that specify a degree to which residues of atoms nearest to the voxels have aligned template structures.

39. The computer-readable media of clause 38, wherein the structure confidence channels are template modeling scores of the aligned template structures.

40. The computer-readable media of clause 39, wherein the structure confidence channels are a minimum one of the template modeling scores, a mean of the template modeling scores, and a maximum one of the template modeling scores.

41. The computer-readable media of clause 1, the operations further comprising rotating the atoms before the amino acid-wise distance channels are generated.

42. The computer-readable media of clause 1, the operations further comprising using 1×1×1 convolutions, 3×3×3 convolutions, rectified linear unit activation layers, batch normalization layers, a fully-connected layer, a dropout regularization layer, and a softmax classification layer in a convolutional neural network.

43. The computer-readable media of clause 42, wherein the 1×1×1 convolutions and the 3×3×3 convolutions are three-dimensional convolutions.

44. The computer-readable media of clause 42, wherein a layer of the 1×1×1 convolutions processes the tensor and produces an intermediate output that is a convolved representation of the tensor, wherein a sequence of layers of the 3×3×3 convolutions processes the intermediate output and produces a flattened output, wherein the fully-connected layer processes the flattened output and produces unnormalized outputs, and wherein the softmax classification layer processes the unnormalized outputs and produces exponentially normalized outputs that identify likelihoods of the variant nucleotide being pathogenic and benign.

45. The computer-readable media of clause 44, wherein a sigmoid layer processes the unnormalized outputs and produces a normalized output that identifies a likelihood of the variant nucleotide being pathogenic.

46. The computer-readable media of clause 1, wherein the convolutional neural network is an attention-based neural network.

47. The computer-readable media of clause 1, wherein the tensor includes the amino acid-wise distance channels further encoded with the reference allele channel.

48. The computer-readable media of clause 1, wherein the tensor includes the amino acid-wise distance channels further encoded with the annotation channels.

49. The computer-readable media of clause 1, wherein the tensor includes the amino acid-wise distance channels further encoded with the structure confidence channels.

50. One or more computer-readable media storing computer-executable instructions that, when executed on one or more processors, configure a computer to perform operations comprising:

accessing a three-dimensional structure of a reference amino acid sequence of a protein, and fitting a three-dimensional grid of voxels on atoms in the three-dimensional structure on an amino acid-basis to generate atom category-wise distance channels, wherein the atoms span a plurality of atom categories, wherein atom categories in the plurality of atom categories specify atomic elements of the amino acids, wherein each of the atom category-wise distance channels has a three-dimensional distance value for each voxel in the three-dimensional grid of voxels, and wherein the three-dimensional distance value specifies a distance from a corresponding voxel in the three-dimensional grid of voxels to atoms of corresponding atom categories in the plurality of atom categories;

encoding an alternative allele channel to each voxel in the three-dimensional grid of voxels, wherein the alternative allele channel is a three-dimensional representation of a one-hot encoding of a variant amino acid expressed by a variant nucleotide;

encoding an evolutionary conservation channel to each sequence of three-dimensional distance values across the atom category-wise distance channels on a voxel position-basis, wherein the evolutionary conservation channel is a three-dimensional representation of amino acid-specific conservation frequencies across a plurality of species, and wherein the amino acid-specific conservation frequencies are selected in dependence upon amino acid proximity to the corresponding voxel;

applying three-dimensional convolutions to a tensor that includes the atom category-wise distance channels encoded with the alternative allele channel and respective evolutionary conservation channels; and determining a pathogenicity of the variant nucleotide based at least in part on the tensor.

51. One or more computer-readable media storing computer-executable instructions that, when executed on one or more processors, configure a computer to perform operations comprising:

accessing a three-dimensional structure of a reference amino acid sequence of a protein, and fitting a three-dimensional grid of voxels on atoms in the three-dimensional structure on an amino acid-basis to generate amino acid-wise distance channels, wherein each of the amino acid-wise distance channels has a three-dimensional distance value for each voxel in the three-dimensional grid of voxels, and wherein the three-dimensional distance value specifies a distance from a corresponding voxel in the three-dimensional grid of voxels to atoms of a corresponding reference amino acid in the reference amino acid sequence;

encoding an alternative allele channel to each three-dimensional distance value in each of the amino acid-wise distance channels on an amino acid position-basis, wherein the alternative allele channel is a three-dimensional representation of a one-hot encoding of a variant amino acid expressed by a variant nucleotide;

encoding an evolutionary conservation channel to each sequence of three-dimensional distance values across the amino acid-wise distance channels on a voxel position-basis, wherein the evolutionary conservation channel is a three-dimensional representation of amino acid-specific conservation frequencies across a plurality of species, and wherein the amino acid-specific conservation frequencies are selected in dependence upon amino acid proximity to the corresponding voxel; and generating a tensor that includes the amino acid-wise distance channels encoded with the alternative allele channel and respective evolutionary conservation channels.

52. One or more computer-readable media storing computer-executable instructions that, when executed on one or more processors, configure a computer to perform operations comprising:

accessing a three-dimensional structure of a reference amino acid sequence of a protein, and fitting a three-dimensional grid of voxels on atoms in the three-dimensional structure on an amino acid-basis to generate atom category-wise distance channels, wherein the atoms span a plurality of atom categories, wherein atom categories in the plurality of atom categories specify atomic elements of the amino acids, wherein each of the atom category-wise distance channels has a three-dimensional distance value for each voxel in the three-dimensional grid of voxels, and wherein the three-dimensional distance value specifies a distance from a corresponding voxel in the three-dimensional grid of voxels to atoms of corresponding atom categories in the plurality of atom categories;

encoding an alternative allele channel to each voxel in the three-dimensional grid of voxels, wherein the alternative allele channel is a three-dimensional representation of a one-hot encoding of a variant amino acid expressed by a variant nucleotide;

encoding an evolutionary conservation channel to each sequence of three-dimensional distance values across the atom category-wise distance channels on a voxel position-basis, wherein the evolutionary conservation channel is a three-dimensional representation of amino acid-specific conservation frequencies across a plurality of species, and wherein the amino acid-specific conservation frequencies are selected in dependence upon amino acid proximity to the corresponding voxel; and generating a tensor that includes the atom category-wise distance channels encoded with the alternative allele channel and respective evolutionary conservation channels.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Particular Implementations 3

1. A computer-implemented method of efficiently determining which elements of a sequence are nearest to uniformly spaced cells in a grid, wherein the elements have element coordinates, and the cells have dimension-wise cell indices and cell coordinates, including:
generating an element-to-cells mapping that maps, to each of the elements, a subset of the cells,
wherein the subset of the cells mapped to a particular element in the sequence includes a nearest cell in the grid and one or more neighborhood cells in the grid,
wherein the nearest cell is selected based on matching element coordinates of the particular element to the cell coordinates, and
wherein the neighborhood cells are contiguously adjacent to the nearest cell and selected based on being within a distance proximity range from the particular element;
generating a cell-to-elements mapping that maps, to each of the cells, a subset of the elements,
wherein the subset of the elements mapped to a particular cell in the grid includes those elements in the sequence that are mapped to the particular cell by the element-to-cells mapping; and using the cell-to-elements mapping to determine, for each of the cells, a nearest element in the sequence,
wherein the nearest element to the particular cell is determined based on distances between the particular cell and the elements in the subset of the elements.

2. The computer-implemented method of clause 1, wherein the matching the element coordinates of the particular element to the cell coordinates further includes truncating a decimal portion of the element coordinates to generate truncated element coordinates.

3. The computer-implemented method of clause 2, wherein the matching the element coordinates of the particular element to the cell coordinates further includes:
for a first dimension, matching a first truncated element coordinate in the truncated element coordinates to a first cell coordinate of a first cell in the grid, and selecting a first dimension index of the first cell;
for a second dimension, matching a second truncated element coordinate in the truncated element coordinates to a second cell coordinate of a second cell in the grid, and selecting a second dimension index of the second cell;
for a third dimension, matching a third truncated element coordinate in the truncated element coordinates to a third cell coordinate of a third cell in the grid, and selecting a third dimension index of the third cell;
using the selected first, second, and third dimension indices to generate an accumulated sum based on position-wise weighting the selected first, second, and third dimension indices by powers of a radix; and
using the accumulated sum as a cell index for selection of the nearest cell.

4. The computer-implemented method of clause 1, wherein the distances are calculated between cell coordinates of the particular cell and element coordinates of the elements in the subset of the elements.

5. The computer-implemented method of clause 1, wherein the sequence is a protein sequence of amino acids.

6. The computer-implemented method of clause 5, wherein the elements are atoms of the amino acids.

7. The computer-implemented method of clause 6, wherein the steps of generating the element-to-cells mapping, generating the cell-to-elements mapping, and using the cell-to-elements mapping to determine, for each of the cells, the nearest element have a runtime complexity of $O(a*f+v)$, wherein
a is a number of the atoms,
f is a number of the amino acids,
v is a number of the cells, and
* is a multiplication operation.

8. The computer-implemented method of clause 7, wherein the atoms include alpha carbon atoms.

9. The computer-implemented method of clause 7, wherein the atoms include beta carbon atoms.

10. The computer-implemented method of clause 7, wherein the atoms include non-carbon atoms.

11. The computer-implemented method of clause 1, wherein the cells are three-dimensional voxels.

12. The computer-implemented method of clause 11, wherein the cell coordinates are three-dimensional coordinates.

13. The computer-implemented method of clause 12, wherein the element coordinates are three-dimensional coordinates.

14. The computer-implemented method of clause 1, wherein the neighborhood cells are selected based on being within an index adjacency range from the nearest cell.

15. The computer-implemented method of clause 1, wherein the neighborhood cells are selected based on being within a cell neighborhood in the grid that includes the nearest cell.

16. The computer-implemented method of clause 1, wherein the sequence includes M elements, wherein the subset of the elements includes N elements, and wherein M>>N.

17. A computer-implemented method of efficiently determining which atoms in a protein are nearest to voxels in a grid, wherein the atoms have three-dimensional (3D) atom coordinates, and the voxels have 3D voxel coordinates, including:
generating an atom-to-voxels mapping that maps, to each of the atoms, a containing voxel selected based on matching 3D atom coordinates of a particular atom of the protein to the 3D voxel coordinates in the grid;
generating a voxel-to-atoms mapping that maps, to each of the voxels, a subset of the atoms, wherein the subset of the atoms mapped to a particular voxel in the grid includes those atoms in the protein that are mapped to the particular voxel by the atom-to-voxels mapping; and
using the voxel-to-atoms mapping to determine, for each of the voxels, a nearest atom in the protein.

18. The computer-implemented method of clause 17, wherein the steps of clause 17 have a runtime complexity of O(number of atoms).

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

While the present invention is disclosed by reference to the preferred implementations and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A computer-implemented method, comprising:
accessing a three-dimensional structure of a reference amino acid sequence of a protein;
mapping atoms of the three-dimensional structure to respective voxels of a three-dimensional voxel grid by associating each atom with an individual voxel of the three-dimensional voxel grid;
defining, for each voxel in the three-dimensional voxel grid on an amino acid basis, amino acid-wise distance channels comprising three-dimensional distance values specifying distances from each respective voxel to corresponding atoms mapped to each respective voxel;
encoding an alternative allele channel to each voxel in the three-dimensional voxel grid, wherein the alternative allele channel is a three-dimensional representation of a one-hot encoding of a variant amino acid expressed by a variant nucleotide;
encoding an evolutionary conservation channel to each sequence of three-dimensional distance values across the amino acid-wise distance channels on a voxel position basis, wherein the evolutionary conservation channel is a three-dimensional representation of amino acid-specific conservation frequencies across a plurality of species, and wherein the amino acid-specific conservation frequencies are selected in dependence upon amino acid proximity to a corresponding voxel;
applying three-dimensional convolutions to a tensor that includes the amino acid-wise distance channels encoded with the alternative allele channel and respective evolutionary conservation channels; and
determining a pathogenicity of the variant nucleotide based at least in part on the tensor.

2. The computer-implemented method of claim 1, further comprising centering the three-dimensional voxel grid on an alpha carbon atom of respective residues of reference amino acids in the reference amino acid sequence.

3. The computer-implemented method of claim 2, further comprising centering the three-dimensional voxel grid on an alpha carbon atom of a residue of a particular reference amino acid that corresponds to the variant amino acid.

4. The computer-implemented method of claim 3, further comprising encoding, in the tensor, a directionality of the reference amino acids in the reference amino acid sequence and a position of the particular reference amino acid by multiplying, with a directionality parameter, three-dimensional distance values for those reference amino acids that precede the particular reference amino acid.

5. The computer-implemented method of claim 4, wherein distances specified by three-dimensional distance values are nearest-atom distances from corresponding voxel centers in the three-dimensional voxel grid to nearest atoms of corresponding reference amino acids.

6. The computer-implemented method of claim 5, wherein the nearest-atom distances are Euclidean distances.

7. The computer-implemented method of claim 6, wherein the nearest-atom distances are normalized by dividing the Euclidean distances with a maximum nearest-atom distance.

8. The computer-implemented method of claim 5, wherein the reference amino acids have alpha carbon atoms and wherein the distances specified by the three-dimensional distance values are nearest-alpha carbon atom distances from the corresponding voxel centers to nearest alpha carbon atoms of the corresponding reference amino acids.

9. The computer-implemented method of claim 5, wherein the reference amino acids have beta carbon atoms and wherein the distances specified by the three-dimensional distance values are nearest-beta carbon atom distances from the corresponding voxel centers to nearest beta carbon atoms of the corresponding reference amino acids.

10. The computer-implemented method of claim 5, wherein the reference amino acids have backbone atoms and wherein the distances specified by the three-dimensional distance values are nearest-backbone atom distances from the corresponding voxel centers to nearest backbone atoms of the corresponding reference amino acids.

11. The computer-implemented method of claim 5, wherein the reference amino acids have sidechain atoms and wherein the distances specified by the three-dimensional distance values are nearest-sidechain atom distances from the corresponding voxel centers to nearest sidechain atoms of the corresponding reference amino acids.

12. The computer-implemented method of claim 3, further comprising encoding, in the tensor, a nearest atom channel that specifies a distance from each voxel to a nearest atom, wherein the nearest atom is selected irrespective of the reference amino acids and atomic elements of the reference amino acids.

13. The computer-implemented method of claim 12, wherein the distance is a Euclidean distance.

14. The computer-implemented method of claim 13, wherein the distance is normalized by dividing the Euclidean distance with a maximum distance.

15. The computer-implemented method of claim 12, wherein the reference amino acids include non-standard amino acids.

16. The computer-implemented method of claim 1, wherein the tensor further includes an absentee atom channel that specifies atoms not found within a predefined radius of a voxel center.

17. The computer-implemented method of claim 16, wherein the absentee atom channel is one-hot encoded.

18. The computer-implemented method of claim 1, further comprising voxel-wise encoding a reference allele channel to each voxel in the three-dimensional voxel grid.

19. The computer-implemented method of claim 18, wherein a reference allele amino acid for the reference allele channel is a three-dimensional representation of a one-hot encoding of a reference amino acid that experiences the variant amino acid.

20. The computer-implemented method of claim 1, wherein the amino acid-specific conservation frequencies specify conservation levels of respective amino acids across the plurality of species.

21. The computer-implemented method of claim 20, further comprising encoding the evolutionary conservation channel to each sequence of three-dimensional distance values by:
selecting a nearest atom to the corresponding voxel across reference amino acids from the reference amino acid sequence and atom categories, selecting pan-amino acid conservation frequencies for a residue of a reference amino acid that includes the nearest atom, and using a three-dimensional representation of the pan-amino acid conservation frequencies as the evolutionary conservation channel.

22. The computer-implemented method of claim 21, wherein the pan-amino acid conservation frequencies are configured for a particular position of the residue as observed in the plurality of species.

23. The computer-implemented method of claim 21, wherein the pan-amino acid conservation frequencies specify whether there is a missing conservation frequency for a particular reference amino acid.

24. The computer-implemented method of claim 21, further comprising:

selecting respective nearest atoms to the corresponding voxel in respective ones of the reference amino acids, selecting respective per-amino acid conservation frequencies for respective residues of the reference amino acids that include nearest atoms, and using a three-dimensional representation of the respective per-amino acid conservation frequencies as the evolutionary conservation channel.

25. The computer-implemented method of claim 24, wherein the respective per-amino acid conservation frequencies are configured for a particular position of the respective residues as observed in the plurality of species.

26. The computer-implemented method of claim 24, wherein the respective per-amino acid conservation frequencies specify whether there is a missing conservation frequency for a particular reference amino acid.

27. The computer-implemented method of claim 1, further comprising voxel-wise encoding one or more annotation channels to each voxel in the three-dimensional voxel grid, wherein the one or more annotation channels are three-dimensional representations of a one-hot encoding of residue annotations.

28. The computer-implemented method of claim 27, wherein the one or more annotation channels are molecular processing annotations that include initiator methionine, signal, transit peptide, propeptide, chain, and peptide.

29. The computer-implemented method of claim 27, wherein the one or more annotation channels are regions annotations that include topological domain, transmembrane, intramembrane, domain, repeat, calcium binding, zinc finger, deoxyribonucleic acid (DNA) binding, nucleotide binding, region, coiled coil, motif, and compositional bias.

30. The computer-implemented method of claim 27, wherein the one or more annotation channels are sites annotations that include active site, metal binding, binding site, and site.

\* \* \* \* \*